United States Patent
Quinn et al.

(10) Patent No.: US 9,579,366 B2
(45) Date of Patent: Feb. 28, 2017

(54) RECOMBINANT HUMAN NAGLU PROTEIN AND USES THEREOF

(71) Applicant: SYNAGEVA BIOPHARMA CORP., Lexington, MA (US)

(72) Inventors: Anthony Quinn, Chestnut Hill, MA (US); Markley C. Leavitt, Watkinsville, GA (US); Zhinan Xia, Wellesley, MA (US)

(73) Assignee: ALEXION PHARMACEUTICALS, INC., New Haven, CT (US)

( * ) Notice: Subject to any disclaimer, the term of this patent is extended or adjusted under 35 U.S.C. 154(b) by 776 days.

(21) Appl. No.: 13/649,595

(22) Filed: Oct. 11, 2012

(65) Prior Publication Data

US 2013/0095092 A1   Apr. 18, 2013

Related U.S. Application Data

(60) Provisional application No. 61/546,248, filed on Oct. 12, 2011.

(51) Int. Cl.

| | | |
|---|---|---|
| *A61K 38/00* | (2006.01) | |
| *A61K 38/47* | (2006.01) | |
| *A61K 45/06* | (2006.01) | |
| *C12N 9/24* | (2006.01) | |
| *A61K 31/7024* | (2006.01) | |
| *C07K 7/06* | (2006.01) | |
| *C07K 7/08* | (2006.01) | |
| *C12N 9/26* | (2006.01) | |

(52) U.S. Cl.
CPC .......... *A61K 38/47* (2013.01); *A61K 31/7024* (2013.01); *A61K 45/06* (2013.01); *C07K 7/06* (2013.01); *C07K 7/08* (2013.01); *C12N 9/2402* (2013.01); *C12N 9/2474* (2013.01); *C12Y 302/0105* (2013.01)

(58) Field of Classification Search
None
See application file for complete search history.

(56) References Cited

U.S. PATENT DOCUMENTS

| | | | |
|---|---|---|---|
| 6,670,165 B2 | 12/2003 | Canfield | |
| 6,861,242 B2 | 3/2005 | Canfield | |
| 7,001,994 B2 | 2/2006 | Zhu | |
| 7,138,262 B1 | 11/2006 | Daniel | |
| 9,044,473 B2* | 6/2015 | Kakkis | A61K 38/47 |
| 2004/0248262 A1 | 12/2004 | Koeberl et al. | |
| 2005/0142141 A1 | 6/2005 | Pardridge | |
| 2009/0022702 A1 | 1/2009 | Zhu | |
| 2009/0166224 A1* | 7/2009 | Yang | C07K 1/22 205/792 |
| 2010/0183577 A1 | 7/2010 | Stern et al. | |
| 2011/0318327 A1 | 12/2011 | Concino et al. | |
| 2012/0003202 A1* | 1/2012 | Calias | A61K 9/0085 424/94.3 |
| 2012/0021436 A1 | 1/2012 | Meiyappan et al. | |
| 2012/0064055 A1 | 3/2012 | Quinn et al. | |
| 2014/0255383 A1* | 9/2014 | Quinn | A61K 38/47 424/94.61 |

FOREIGN PATENT DOCUMENTS

| | | |
|---|---|---|
| CN | 101410408 | 4/2009 |
| WO | WO-2009/088998 A2 | 7/2009 |
| WO | WO-2009/131698 A2 | 10/2009 |
| WO | WO-2011/000958 A1 | 1/2011 |
| WO | WO2011/163652 | 12/2011 |

OTHER PUBLICATIONS

Natale et al., "Treatment of the Mouse Model of Mucopolysaccharidosis Type IIIB with Lentiviral-NAGLU Vector," Biochem., 388:639-646 (2005).
Weber et al., "Expression and Characterization of Human Recombinant and α-N-Actylglucosaminidase." Protein Expresion and Purification, 21:251-259 (2001).
Zhao et al., "The Molecular Basis of Sanfilippo Syndrome Type B," Proc. Natl. Acad. Sci, USA, 93:6101-6105 (1995).
Bones et al. "Identification of N-Glycans Displaying Mannose-6-Phosphate and their Site of Attachment on Therapeutic Enzymes for Lysosomal Storage Disorder Treatment." *Anal. Chem.* Jul. 2011, 83(13): 5344-52.
Braulke, et al. "Sorting of Lysosomal Proteins" *Biochim. Biophys Acta.* 2009, 1793(4):605-14.
Chen, et al. "Glycoproteomics Analysis of Human Liver Tissue by Combination of Multiple Enzyme Digestion and Hydrazide Chemistry." *J. Proteome Res.* 2009, 8(2): 651-61.
Ellinwood et al. "Safe, Efficient and Reproducible Gene Therapy of the Brain in the Dog Models of Sanfilippo and Hurler Syndromes." *Mol. Ther.* Feb. 2011, 19(2): 251-259.
International Search Report and Written Opinion for PCT/US2012/59708. Mailed Apr. 8, 2013.
Kim, et al. "Carbohydrate Recognition by the Mannose-6-Phosphate Receptors." *Curr. Opin. Struct. Biol.* 2009, 19(5): 534-42, p. 10.
Liu, et al. "Chemical Synthesis of N-linked Glycans Carrying Both Mannose-6-Phosphate and GlcNAc-Mannose-6-Phosphate Motifs." *J. Org. Chem.* Epub Oct. 6, 2011, 76(21): 8682-8689.
Mizutani, et al. "Genetic Modification of a Chicken Expression System for the Galactosylation of Therapeutic Proteins Produced in Egg White". *Transgenic Res.* Epub Apr. 13, 2011, 21(1):63-75.
Pohl, et al. "Glycosylation-and Phosphorylation-Dependent Intracellular Transport of Lysosomal Hydrolases" *Biol. Chem.* 2009, 390(7): 521-7.
UniProtKB/Swiss-Prot Direct Submission P54802. ANAG_HUMAN (Sep. 21, 2011). [Retrieved from Internet Feb. 21, 2013: //www.unipro.org/uniprot/P54802.txt?version=111>]; p. 5.
U.S. Appl. No. 13/642,790, Synageva BioPharma Corp.
U.S. Appl. No. 13/583,973, Synageva BioPharma Corp.

* cited by examiner

*Primary Examiner* — Anand Desai
(74) *Attorney, Agent, or Firm* — McDermott Will & Emery LLP

(57) ABSTRACT

The present invention provides compositions comprising an isolated mixture of recombinant human NaGlu proteins in which a substantial amount of the NaGlu proteins in the mixture has increased levels of phosphorylated mannose that confer the proteins to be efficiently internalized into human cells. The present invention also provides methods of producing such mixture of NaGlu proteins, vectors used in transgenesis and expression, host cells harboring such vectors, and methods of isolating and purifying the mixture of NaGlu proteins. The invention further provides methods of treating NaGlu associated diseases.

18 Claims, 19 Drawing Sheets

Human NaGlu Amino Acid Sequence (signal peptide: 1-23, underlined)

```
MEAVAVAAAV GVLLLAGAGG AAGDEAREAA AVRALVARLL GPGPAADFSV SVERALAAKP    60
GLDTYSLGGG GAARVRVRGS TGVAAAAGLH RYLRDFCGCH VAWSGSQLRL PRPLPAVPGE   120
LTEATPNRYR YYQNVCTQSY SFVWWDWARW EREIDWMALN GINLALAWSG QEAIWQRVYL   180
ALGLTQAEIN EFFTGPAFLA WGRMGNLHTW DGPLPPSWHI KQLYLQHRVL DQMRSFGMTP   240
VLPAFAGHVP EAVTRVFPQV NVTKMGSWGH FNCSYSCSFL LAPEDPIFPI IGSLFLRELI   300
KEFGTDHIYG ADTFNEMQPP SSEPSYLAAA TTAVYEAMTA VDTEAVWLLQ GWLFQHQPQF   360
WGPAQIRAVL GAVPRGRLLV LDLFAESQPV YTRTASFQGQ PFIWCMLHNF GGNHGLFGAL   420
EAVNGGPEAA RLFPNSTMVG TGMAPEGISQ NEVVYSLMAE LGWRKDPVPD LAAWVTSFAA   480
RRYGVSHPDA GAAWRLLLRS VYNCSGEACR GHNRSPLVRR PSLQMNTSIW YNRSDVFEAW   540
RLLLTSAPSL ATSPAFRYDL LDLTRQAVQE LVSLYYEEAR SAYLSKELAS LLRAGGVLAY   600
ELLPALDEVL ASDSRFLLGS WLEQARAAAV SEAEADFYEQ NSRYQLTLWG PEGNILDYAN   660
KQLAGLVANY YTPRWRLFLE ALVDSVAQGI PFQQHQFDKN VFQLEQAFVL SKQRYPSQPR   720
GDTVDLAKKI FLKYYPRWVA GSW                                          743
```

(SEQ ID NO:1)

Fig. 1

Human NaGlu Coding Sequence (cDNA)

```
atggaggcgg tggcggtggc cgcggcggtg ggggtccttc tcctggccgg ggccgggggc      60
gcggcaggcg acgaggcccg ggaggcggcg gccgtgcggg cgctcgtggc ccggctgctg     120
gggccaggcc ccgcggccga cttctccgtg tcggtggagc gcgctctggc tgccaagccg     180
ggcttggaca cctacagcct gggcggcggc ggcgcggcgc gcgtgcgggt gcgcggctcc     240
acgggcgtgg cagccgccgc ggggctgcac cgctacctgc gcgacttctg tggctgccac     300
gtggcctggt ccggctctca gctgcgcctg ccgcggccac tgccagccgt gccggggag      360
ctgaccgagg ccacgcccaa caggtaccgc tattaccaga atgtgtgcac gcaaagctac     420
tctttcgtgt ggtgggactg ggcccggtgg gagcgagaga tagactggat ggcgctgaat     480
ggcatcaacc tggcactggc atggagcggc caggaggcca tctggcagcg ggtgtacctg     540
gccttgggcc tgacccaggc agagatcaat gagttcttta ctggtcctgc cttcttggca     600
tggggcgaa tgggcaacct gcacacctgg gatggccccc tgccccctc ctggcacatc      660
aagcagcttt atctgcagca ccgggtcctg accagatgc gctccttcgg catgaccca      720
gtgctgcctg cattcgcggg gcatgttccc gaggctgtca ccagggtgtt ccctcaggtc     780
aatgtcacga agatgggcag ttggggccac tttaactgtt cctactcctg ctccttcctt     840
ctggctccgg aagaccccat attccccatc atcgggagcc tcttcttgcg agagctgatc     900
aaagagtttg gcacagacca catctatggg gccgacactt tcaatgagat gcagccacct    960
tcctcagagc cctcctatct gccgcagcc accactgccg tctatgaggc catgactgca     1020
gtggatactg aggctgtgtg gctgctccaa ggctggctct ccagcacca gccgcagttc    1080
tgggggcccg cccagatcag ggctgtgctg ggagctgtgc ccgtggccg cctcctggtt    1140
ctggacctgt tgctgagag ccagcctgtg tatacccgca ctgcctcctt ccaaggccag    1200
cccttcatct ggtgcatgct gcacaacttt ggggaaatc atggtctttt tggagccttg     1260
gaggccgtga acggaggccc agaagctgcc cgcctcttcc ccaactccac aatggtaggc    1320
acgggcatgg cccccgaggg catcagccag aacgaagtgg tctattccct catggctgag    1380
ctgggctggc gaaaggaccc agtgccagat tggcagcct gggtgaccag ctttgccgcc    1440
cggcggtatg gggtctccca cccggacgca ggggcagcgt ggaggctact gctccggagt    1500
gtgtacaact gctccgggga ggcatgcagg ggccacaatc gtagcccgct ggtcaggcgg    1560
ccgtccctac agatgaatac cagcatctgg tacaaccgat ctgatgtgtt tgaggcctgg    1620
cggctgctgc tcacatctgc tccctccctg gccaccagcc ccgccttccg ctacgacctg    1680
ctggacctca ctcggcaggc agtgcaggag ctggtcagct tgtattatga ggaggcaaga    1740
agcgcctatc tgagcaagga gctggcctcc ttgttgaggg ctggaggcgt cctggcctat    1800
gagctgctgc cggcactgga cgaggtgctg gctagtgaca ccgcttctt gctgggcagc    1860
tggctagagc aggcccgagc agcggcagtc agtgaggccg aggccgattt ctacgagcag    1920
aacagccgct accagctgac cttgtggggg ccagaaggca acatcctgga ctatgccaac    1980
aagcagctgg cggggttggt ggccaactac tacacccctc gctggcggct tttcctggag    2040
gcgctggttg acagtgtggc ccagggcatc cctttccaac agcaccagtt tgacaaaaat    2100
gtcttccaac tggagcaggc cttcgttctc agcaagcaga ggtaccccag ccagccgcga    2160
ggagacactg tggacctggc caagaagatc ttcctcaaat attaccccg ctgggtggcc    2220
ggctcttggt gatt                                                      2234
```

(SEQ ID NO:2)

Fig. 2

1.1kb OV promoter

```
gttaagtcct cagacttggc aaggagaatg tagatttcca cagtatatat gttttcacaa    60
aaggaaggag agaaacaaaa gaaaatggca ctgactaaac ttcagctagt ggtataggaa   120
agtaattctg cttaacagag attgcagtga tctctatgta tgtcctgaag aattatgttg   180
tacttttttc ccccattttt aaatcaaaca gtgctttaca gaggtcagaa tggtttcttt   240
actgtttgtc aattctatta tttcaataca gaacaatagc ttctataact gaaatatatt   300
tgctattgta tattatgatt gtccctcgaa ccatgaacac tcctccagct gaatttcaca   360
attcctctgt catctgccag gccattaagt tattcatgga agatctttga ggaacactgc   420
aagttcatat cataaacaca tttgaaattg agtattgttt tgcattgtat ggagctatgt   480
tttgctgtat cctcagaata aaagtttgtt ataaagcatt cacacccata aaaagataga   540
tttaaatatt ccaactatag gaagaaagt gtgtctgctc ttcactctag tctcagttgg    600
ctccttcaca tgcacgcttc tttatttctc ctattttgtc aagaaaataa taggtcaagt   660
cttgttctca tttatgtcct gtctagcgtg gctcagatgc acattgtaca tacaagaagg   720
atcaaatgaa acagacttct ggtctgttac tacaaccata gtaataagca cactaactaa   780
taattgctaa ttatgttttc catctccaag gttcccacat ttttctgttt tcttaaagat   840
cccattatct ggttgtaact gaagctcaat ggaacatgag caatatttcc cagtcttctc   900
tcccatccaa cagtcctgat ggattagcag aacaggcaga aaacacattg ttacccagaa   960
ttaaaaacta atatttgctc tccattcaat ccaaaatgga cctattgaaa ctaaaatcta  1020
acccaatccc attaaatgat ttctatggtg tcaaaggtca aacttctgaa gggaacctgt  1080
gggtgggtca caattcagac tatatattcc ccagggctca gccagtgtct gt          1132
```

(SEQ ID NO:3)

Fig. 3 pSIN-OV-1.1-I-rhNaGlu

```
ggccgcaaga agaaagctga aaaactctgt cccttccaac aagacccaga gcactgtagt    60
atcaggggta aaatgaaaag tatgttatct gctgcatcca gacttcataa aagctggagc   120
ttaattcaga aaaaaaatca gaaagaaatt acactgtgag aacaggtgca attcactttt   180
cctttacaca gagtaatact ggtaactcat ggatgaaggc ttaagggaat gaaattggac   240
tcacagtact gagtcatcac actgaaaaat gcaacctgat acatcagcag aaggtttatg   300
ggggaaaaat gcagccttcc aattaagcca gatatctgta tgaccaagct gctccagaat   360
tagtcactca aaatctctca gattaaatta tcaactgtca ccaaccattc ctatgctgac   420
aaggcaattg cttgttctct gtgttcctga tactacaagg ctcttcctga cttcctaaag   480
atgcattata aaaatcttat aattcacatt tctccctaaa ctttgactca atcatggtat   540
gttggcaaat atggtatatt actattcaaa ttgttttcct tgtacccata tgtaatgggt   600
cttgtgaatg tgctcttttg ttcctttaat cataataaaa acatgtttaa gcaaacactt   660
ttcacttgta gtatttgaag gtaccggatc tcgagccgcc ttcaatgccc caaaaccaa    720
tccccaggtt tttaactctc ccgatttccc aagtaccata gcccgctgag agagcgccgc   780
ggtaatggga tcccaggacc ccggggaata taagtctgag ggggacgtaa gcaacccttc   840
cttttgtaac agggacaaca tagcccctat ttccttctta gaaggagagg ttttcccgca   900
ataggtctta cacgcggacg aaatcacctt tatgacggct tccatgcttg atccaccggg   960
cgaccggaat cacgcagagc aaccggaatc acgcctgggg tggaccgctc agtcgtcggg  1020
cttccttccc gtcttccaac gactctctga gttctcggta gggtatgttg ccccctgca   1080
gtagggctcc ctccgacgcc actcagcttc tgccctccta agccgcagcc cctctacta   1140
gggtcatcgt ccgctccccg aataagcgag acggatgagg acaggatcgc cacgccgcct  1200
gtggccgacc actattccct aacgatcacg tcgggtcac caaatgaagc cttctgcttc   1260
atgcatgtgc tcgtagtcgt cagggaatca acggtccggc catcaaccca ggtgcacacc  1320
aatgtggtga atggtcaaat ggcgttatt gtatcgagct aggcacttaa atacaatatc   1380
tctgcaatgc ggaattcagt ggttcgtcca atccgtgtta gacccgtctg ttgccttcct  1440
aacaaggcac gatcatacca cgatcatacc accttactcc caccaatcgg catgcacggt  1500
gctttttctc tccttataag gcatgttgct aactcatcgt tacataagca tgttgcaaga  1560
ctacaagagt attgcataag actacatttc cccctcccta tgcaaaagcg aaactactat  1620
atcctgaggg gactcctaac cgcgtacaac cgaagccccg cttttcgcct aaacatgcta  1680
ttgtccctc agtcaagcct tgcccgttac aacccgattc gcaagccttg ccctccccac  1740
attatccgta gcattatttc ctagcagtca tcagagctac agaagatact ctatgctgta  1800
gccaagtcta caagtttact attcagcgac ctcctatatt ccgcgtgcca gccgatcaat  1860
taccaatgcg cgcttggcgt aatcatggtc atagctgttt cctgtgtgaa attgttatcc  1920
gctcacaatt ccacacaaca tacgagccgg aagcataaag tgtaaagcct ggggtgccta  1980
atgagtgagc taactcacat taattgcgtt gcgctcactg cccgctttcc agtcgggaaa  2040
cctgtcgtgc cagctgcatt aatgaatcgg ccaacgcgcg gggagaggcg gtttgcgtat  2100
tgggcgctct tccgcttcct cgctcactga ctcgctgcgc tcggtcgttc ggctgcggcg  2160
```

Fig. 4A

```
agcggtatca gctcactcaa aggcggtaat acggttatcc acagaatcag gggataacgc    2220
aggaaagaac atgtgagcaa aaggccagca aaaggccagg aaccgtaaaa aggccgcgtt    2280
gctggcgttt ttccataggc tccgcccccc tgacgagcat cacaaaaatc gacgctcaag    2340
tcagaggtgg cgaaacccga caggactata agataccag gcgtttcccc ctggaagctc     2400
cctcgtgcgc tctcctgttc cgaccctgcc gcttaccgga tacctgtccg cctttctccc    2460
ttcgggaagc gtggcgcttt ctcatagctc acgctgtagg tatctcagtt cggtgtaggt    2520
cgttcgctcc aagctgggct gtgtgcacga accccccgtt cagcccgacc gctgcgcctt    2580
atccggtaac tatcgtcttg agtccaaccc ggtaagacac gacttatcgc cactggcagc    2640
agccactggt aacaggatta gcagagcgag gtatgtaggc ggtgctacag agttcttgaa    2700
gtggtggcct aactacggct acactagaag gacagtattt ggtatctgcg ctctgctgaa    2760
gccagttacc ttcggaaaaa gagttggtag ctcttgatcc ggcaaacaaa ccaccgctgg    2820
tagcggtggt ttttttgttt gcaagcagca gattacgcgc agaaaaaaag gatctcaaga    2880
agatcctttg atcttttcta cggggtctga cgctcagtgg aacgaaaact cacgttaagg    2940
gattttggtc atgagattat caaaaaggat cttcacctag atccttttaa attaaaaatg    3000
aagttttaaa tcaatctaaa gtatatatga gtaaacttgg tctgacagtt accaatgctt    3060
aatcagtgag gcacctatct cagcgatctg tctatttcgt tcatccatag ttgcctgact    3120
ccccgtcgtg tagataacta cgatacggga gggcttacca tctggcccca gtgctgcaat    3180
gataccgcga gacccacgct caccggctcc agatttatca gcaataaacc agccagccgg    3240
aagggccgag cgcagaagtg gtcctgcaac tttatccgcc tccatccagt ctattaattg    3300
ttgccgggaa gctagagtaa gtagttcgcc agttaatagt ttgcgcaacg ttgttgccat    3360
tgctacaggc atcgtggtgt cacgctcgtc gtttggtatg gcttcattca gctccggttc    3420
ccaacgatca aggcgagtta catgatcccc catgttgtgc aaaaaagcgg ttagctcctt    3480
cggtcctccg atcgttgtca gaagtaagtt ggccgcagtg ttatcactca tggttatggc    3540
agcactgcat aattctctta ctgtcatgcc atccgtaaga tgcttttctg tgactggtga    3600
gtactcaacc aagtcattct gagaatagtg tatgcggcga ccgagttgct cttgcccggc    3660
gtcaatacgg gataataccg cgccacatag cagaacttta aaagtgctca tcattggaaa    3720
acgttcttcg gggcgaaaac tctcaaggat cttaccgctg ttgagatcca gttcgatgta    3780
acccactcgt gcacccaact gatcttcagc atcttttact ttcaccagcg tttctgggtg    3840
agcaaaaaca ggaaggcaaa atgccgcaaa aaagggaata agggcgacac ggaaatgttg    3900
aatactcata ctcttccttt ttcaatatta ttgaagcatt tatcagggtt attgtctcat    3960
gagcggatac atatttgaat gtatttagaa aaataaacaa ataggggttc cgcgcacatt    4020
tccccgaaaa gtgccacctg acgcgccctg tagcggcgca ttaagcgcgg cgggtgtggt    4080
ggttacgcgc agcgtgaccg ctacacttgc cagcgcccta gcgcccgctc ctttcgcttt    4140
cttcccttcc tttctcgcca cgttcgccgg ctttccccgt caagctctaa atcgggggct    4200
ccctttaggg ttccgattta gtgctttacg gcacctcgac cccaaaaaac ttgattaggg    4260
tgatggttca cgtagtgggc catcgccctg atagacggtt tttcgccctt gacgttgga    4320
gtccacgttc tttaatagtg gactcttgtt ccaaactgga acaacactca accctatctc    4380
ggtctattct tttgatttat aagggatttt gccgatttcg gcctattggt taaaaaatga    4440
gctgatttaa caaaaattta acgcgaattt taacaaaata ttaacgctta caatttccat    4500
tcgccattca ggctgcgcaa ctgttgggaa gggcgatcgg tgcgggcctc ttcgctatta    4560
cgccagctgg cgaaagggggg atgtgctgca aggcgattaa gttgggtaac gccagggttt    4620
tcccagtcac gacgttgtaa aacgacggcc agtgagcgcg tattccctaa cgatcacgtc    4680
ggggtcacca aatgaagcct tctgcttcat gcatgtgctc gtagtcgtca gggaatcaac    4740
ggtccggcca tcaacccagg tgcacaccaa tgtggtgaat ggtcaaatgg cgtttattgt    4800
atcgagctag gcacttaaat acaatatctc tgcaatgcgg aattcagtgg ttcgtccaat    4860
ccgtcccct cctatgcaa agcgaaact actatatcct gagggactc ctaaccgcgt        4920
acaaccgaag ccccgctttt cgcctaaaca tgctattgtc ccctcagtca gccttgccc      4980
gttacaaccc gattcgcaag ccttgccctc cccacattat ccgtagcatt atttcctagc    5040
agtcatcaga gctacagaag atactctatg ctgtagccaa gtctacaagt ttactattca    5100
```

Fig. 4B

```
gcgacctcct atattccgcg tgccagccga tcaattacca atccaaccag ctatcacacg   5160
gaatacaaga actcgcctac gctcttcttt cgggctgctt ataagcctcc tgtaattttt   5220
ttatattcct cgttaagtcc tcagacttgg caaggagaat gtagatttcc acagtatata   5280
tgttttcaca aaaggaagga gagaaacaaa agaaaatggc actgactaaa cttcagctag   5340
tggtatagga aagtaattct gcttaacaga gattgcagtg atctctatgt atgtcctgaa   5400
gaattatgtt gtactttttt cccccatttt taaatcaaac agtgctttac agaggtcaga   5460
atggtttctt tactgtttgt caattctatt atttcaatac agaacaatag cttctataac   5520
tgaaatatat ttgctattgt atattatgat tgtccctcga accatgaaca ctcctccagc   5580
tgaatttcac aattcctctg tcatctgcca ggccattaag ttattcatgg aagatctttg   5640
aggaacactg caagttcata tcataaacac atttgaaatt gagtattgtt ttgcattgta   5700
tggagctatg ttttgctgta tcctcagaat aaaagtttgt tataaagcat tcacacccat   5760
aaaagatag atttaaatat tccaactata ggaagaaag tgtgtctgct cttcactcta    5820
gtctcagttg gctccttcac atgcacgctt ctttatttct cctattttgt caagaaaata   5880
ataggtcaag tcttgttctc atttatgtcc tgtctagcgt ggctcagatg cacattgtac   5940
atacaagaag gatcaaatga aacagacttc tggtctgtta ctacaaccat agtaataagc   6000
acactaacta ataattgcta attatgtttt ccatctccaa ggttcccaca ttttctgtt    6060
ttcttaaaga tcccattatc tggttgtaac tgaagctcaa tggaacatga gcaatatttc   6120
ccagtcttct ctcccatcca acagtcctga tggattagca gaacaggcag aaaacacatt   6180
gttacccaga attaaaaact aatatttgct ctccattcaa tccaaaatgg acctattgaa   6240
actaaaatct aacccaatcc cattaaatga tttctatggt gtcaaaggtc aaacttctga   6300
agggaacctg tgggtgggtc acaattcaga ctatatattc cccagggctc agccagtgtc   6360
tgtacataca gctagaaagc tgtattgcct ttagcagtca agctcgaaag gtaagcaact   6420
ctctggaatt accttctctc tatattagct cttacttgca cctaaacttt aaaaaattaa   6480
caattattgt gctatgtgtt gtatctttaa gggtgaagta cctgcgtgat ccccctata    6540
aaaacttctc acctgtgtat gcattctgca ctattttatt atgtgtaaaa gctttgtgtt   6600
tgttttcagg aggcttattc tttgtgctta aaatatgttt ttaatttcag aacatcttat   6660
cctgtcgttc actatctgat atgctttgca gtttgcttga ttaacttcta gccctacaga   6720
gtgcacagag agcaaaatca tggtgttcag tgaattctgg ggagttattt taatgtgaaa   6780
attctctaga agtttaattc ctgcaaagtg cagctgctga tcactacaca agataaaaat   6840
gtgggggtg cataaacgta tattcttaca ataatagata catgtgaact tatatacaga    6900
aaagaaaatg agaaaaatgt gtgtgtgtat actcacacac gtggtcagta aaaacttttg   6960
aggggtttaa tacagaaaat ccaatcctga ggccccagca ctcagtacgc atataaaggg   7020
ctgggctctg aaggacttct gactttcaca gattatataa atctcaggaa agcaactaga   7080
ttcatgctgg ctccaaaagc tgtgctttat ataagcacac tggctataca atagttgtac   7140
agttcagctc tttataatag aaacagacag aacaagtata atcttctat tggtctatgt    7200
catgaacaag aattcattca gtggctctgt tttatagtaa acattgctat tttatcatgt   7260
ctgcatttct cttctgtctg aatgtcacca ctaaaattta actccacaga aagtttatac   7320
tacagtacac atgcatatct ttgagcaaag caaaccatac ctgaaagtgc aatagagcag   7380
aatatgaatt acatgcgtgt ctttctccta gactacatga ccccatataa attacattcc   7440
ttatctattc tgccatcacc aaaacaaagg taaaaatact tttgaagatc tactcatagc   7500
aagtagtgtg caacaaacag atatttctct acatttattt ttagggaata aaaataagaa   7560
ataaaatagt cagcaagcct ctgctttctc atatatctgt ccaaacctaa agttactga    7620
aatttgctct tgaatttcc agttttgcaa gcctatcaga ttgtgtttta atcagaggta    7680
ctgaaaagta tcaatgaatt ctagctttca ctgaacaaaa atatgtagag caactggct    7740
tctgggacag tttgctaccc aaaagacaac tgaatgcaaa tacataaata gatttatgaa   7800
tatggttttg aacatgcaca tgagaggtgg atatagcaac agacacatta ccacagaatt   7860
actttaaaac tacttgttaa catttaattg cctaaaaact gctcgtaatt tactgttgta   7920
gcctaccata gagtaccctg catggtacta tgtacagcat tccatcctta cattttcact   7980
```

Fig. 4C

```
gttctgctgt ttgctctaga caactcagag ttcaccatgg aggcggtggc ggtggccgcg    8040
gcggtggggg tccttctcct ggccggggcc gggggcgcgg caggcgacga ggcccgggag    8100
gcggcggccg tgcgggcgct cgtggcccgg ctgctgggcg caggccccgc ggccgacttc    8160
tccgtgtcgg tggagcgcgc tctggctgcc aagccgggct tggacaccta cagcctgggc    8220
ggcggcggcg cggcgcgcgt gcgggtgcgc ggctccacgg gcgtggcagc cgccgcgggg    8280
ctgcaccgct acctgcgcga cttctgtggc tgccacgtgg cctggtccgg ctctcagctg    8340
cgcctgccgc ggccactgcc agccgtgccg ggggagctga ccgaggccac gcccaacagg    8400
taccgctatt accagaatgt gtgcacgcaa agctactctt tcgtgtggtg ggactgggcc    8460
cggtgggagc gagagataga ctggatggcg ctgaatggca tcaacctggc actggcatgg    8520
agcggccagg aggccatctg gcagcgggtg tacctggcct tgggcctgac ccaggcagag    8580
atcaatgagt tctttactgg tcctgccttc ttggcatggg ggcgaatggg caacctgcac    8640
acctgggatg gcccctgcc cccctcctgg cacatcaagc agctttatct gcagcaccgg    8700
gtcctggacc agatgcgctc cttcggcatg accccagtgc tgcctgcatt cgcggggcat    8760
gttcccgagg ctgtcaccag ggtgttccct caggtcaatg tcacgaagat gggcagttgg    8820
ggccacttta actgttccta ctcctgctcc ttccttctgg ctccggaaga ccccatattc    8880
cccatcatcg ggagcctctt cttgcgagag ctgatcaaag agtttggcac agaccacatc    8940
tatggggccg acactttcaa tgagatgcag ccaccttcct cagagccctc ctatcttgcc    9000
gcagccacca ctgccgtcta tgaggccatg actgcagtgg atactgaggc tgtgtggctg    9060
ctccaaggct ggctcttcca gcaccagccg cagttctggg ggcccgccca gatcagggct    9120
gtgctgggag ctgtgccccg tggccgcctc ctggttctgg acctgtttgc tgagagccag    9180
cctgtgtata cccgcactgc ctccttccaa ggccagccct tcatctggtg catgctgcac    9240
aactttgggg gaaatcatgg tcttttgga gccttggagg ccgtgaacgg aggcccagaa    9300
gctgcccgcc tcttccccaa ctccacaatg gtaggcacgg gcatggcccc cgagggcatc    9360
agccagaacg aagtggtcta ttccctcatg gctgagctgg gctggcgaaa ggacccagtg    9420
ccagatttgg cagcctgggt gaccagcttt gccgcccggc ggtatggggt ctcccacccg    9480
gacgcagggg cagcgtggag gctactgctc cggagtgtgt acaactgctc cggggaggca    9540
tgcaggggcc acaatcgtag cccgctggtc aggcggccgt ccctacagat gaataccagc    9600
atctggtaca accgatctga tgtgtttgag gcctggcggc tgctgctcac atctgctccc    9660
tccctggcca ccagccccgc cttccgctac gacctgctgg acctcactcg gcaggcagtg    9720
caggagctgg tcagcttgta ttatgaggag gcaagaagcg cctatctgag caaggagctg    9780
gcctccttgt tgagggctgg aggcgtcctg gcctatgagc tgctgccggc actggacgag    9840
gtgctggcta gtgacagccg cttcttgctg ggcagctggc tagagcaggc ccgagcagcg    9900
gcagtcagtg aggccgaggc cgatttctac gagcagaaca gccgctacca gctgaccttg    9960
tgggggccag aaggcaacat cctggactat gccaacaagc agctggcggg gttggtggcc   10020
aactactaca cccctcgctg gcggcttttc ctggaggcgc tggttgacag tgtggcccag   10080
ggcatcccttt ccaacagca ccagtttgac aaaaatgtct ccaactgga gcaggccttc   10140
gttctcagca agcagaggta ccccagccag ccgcgaggag acactgtgga cctggccaag   10200
aagatcttcc tcaaatatta ccccgctgg gtggccggct cttggtgatt cgaagc        10256
```

(SEQ ID NO:4)

Fig. 4D

SEQUENCE LISTING

```
<160> NUMBER OF SEQ ID NOS: 5

<210> SEQ ID NO 1
<211> LENGTH: 743
<212> TYPE: PRT
<213> ORGANISM: Human

<400> SEQUENCE: 1

Met Glu Ala Val Ala Val Ala Ala Val Gly Val Leu Leu Leu Ala
1               5                   10                  15

Gly Ala Gly Gly Ala Ala Gly Asp Glu Ala Arg Glu Ala Ala Ala Val
            20                  25                  30

Arg Ala Leu Val Ala Arg Leu Leu Gly Pro Gly Pro Ala Ala Asp Phe
            35                  40                  45

Ser Val Ser Val Glu Arg Ala Leu Ala Ala Lys Pro Gly Leu Asp Thr
50                  55                  60

Tyr Ser Leu Gly Gly Gly Ala Ala Arg Val Arg Val Arg Gly Ser
65                  70                  75                  80

Thr Gly Val Ala Ala Ala Gly Leu His Arg Tyr Leu Arg Asp Phe
            85                  90                  95

Cys Gly Cys His Val Ala Trp Ser Gly Ser Gln Leu Arg Leu Pro Arg
            100                 105                 110

Pro Leu Pro Ala Val Pro Gly Glu Leu Thr Glu Ala Thr Pro Asn Arg
            115                 120                 125

Tyr Arg Tyr Tyr Gln Asn Val Cys Thr Gln Ser Tyr Ser Phe Val Trp
            130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
            165                 170                 175

Arg Val Tyr Leu Ala Leu Gly Leu Thr Gln Ala Glu Ile Asn Glu Phe
            180                 185                 190

Phe Thr Gly Pro Ala Phe Leu Ala Trp Gly Arg Met Gly Asn Leu His
            195                 200                 205

Thr Trp Asp Gly Pro Leu Pro Pro Ser Trp His Ile Lys Gln Leu Tyr
210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
            245                 250                 255

Phe Pro Gln Val Asn Val Thr Lys Met Gly Ser Trp Gly His Phe Asn
            260                 265                 270

Cys Ser Tyr Ser Cys Ser Phe Leu Leu Ala Pro Glu Asp Pro Ile Phe
            275                 280                 285
```

-continued

```
Pro Ile Ile Gly Ser Leu Phe Leu Arg Glu Leu Ile Lys Glu Phe Gly
290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Thr Thr Ala Val Tyr Glu
            325                 330                 335

Ala Met Thr Ala Val Asp Thr Glu Ala Val Trp Leu Leu Gln Gly Trp
            340                 345                 350

Leu Phe Gln His Gln Pro Gln Phe Trp Gly Pro Ala Gln Ile Arg Ala
            355                 360                 365

Val Leu Gly Ala Val Pro Arg Gly Arg Leu Leu Val Leu Asp Leu Phe
370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
            405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
            435                 440                 445

Ser Gln Asn Glu Val Val Tyr Ser Leu Met Ala Glu Leu Gly Trp Arg
450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
            485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
            515                 520                 525

Ile Trp Tyr Asn Arg Ser Asp Val Phe Glu Ala Trp Arg Leu Leu Leu
530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
            565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
            595                 600                 605

Val Leu Ala Ser Asp Ser Arg Phe Leu Leu Gly Ser Trp Leu Glu Gln
            610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
            645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
            675                 680                 685

Gly Ile Pro Phe Gln Gln His Gln Phe Asp Lys Asn Val Phe Gln Leu
            690                 695                 700
```

```
Glu Gln Ala Phe Val Leu Ser Lys Gln Arg Tyr Pro Ser Gln Pro Arg
705                 710                 715                 720
Gly Asp Thr Val Asp Leu Ala Lys Lys Ile Phe Leu Lys Tyr Tyr Pro
                725                 730                 735
Arg Trp Val Ala Gly Ser Trp
            740

<210> SEQ ID NO 2
<211> LENGTH: 2234
<212> TYPE: DNA
<213> ORGANISM: Human

<400> SEQUENCE: 2
```

| | | | | | |
|---|---|---|---|---|---|
| atggaggcgg | tggcggtggc | cgcggcggtg | ggggtccttc | tcctggccgg | ggccgggggc | 60 |
| gcggcaggcg | acgaggcccg | ggaggcggcg | gccgtgcggg | cgctcgtggc | ccggctgctg | 120 |
| gggccaggcc | ccgcggccga | cttctccgtg | tcggtggagc | gcgctctggc | tgccaagccg | 180 |
| ggcttggaca | cctacagcct | gggcggcggc | ggcgcggcgc | cgtgcgggt | gcgcggctcc | 240 |
| acgggcgtgg | cagccgccgc | ggggctgcac | cgctacctgc | gcgacttctg | tggctgccac | 300 |
| gtggcctggt | ccggctctca | gctgcgcctg | ccgcggccac | tgccagccgt | gccggggag | 360 |
| ctgaccgagg | ccacgcccaa | caggtaccgc | tattaccaga | atgtgtgcac | gcaaagctac | 420 |
| tctttcgtgt | ggtgggactg | ggcccggtgg | gagcgagaga | tagactggat | ggcgctgaat | 480 |
| ggcatcaacc | tggcactggc | atggagcggc | caggaggcca | tctggcagcg | ggtgtacctg | 540 |
| gccttgggcc | tgacccaggc | agagatcaat | gagttcttta | ctggtcctgc | cttcttggca | 600 |
| tggggggcgaa | tgggcaacct | gcacacctgg | gatgcccccc | tgccccctc | ctggcacatc | 660 |
| aagcagcttt | atctgcagca | ccgggtcctg | gaccagatgc | gctccttcgg | catgaccca | 720 |
| gtgctgcctg | cattcgcggg | gcatgttccc | gaggctgtca | ccagggtgtt | ccctcaggtc | 780 |
| aatgtcacga | gatgggcag | ttggggccac | tttaactgtt | cctactcctg | ctccttcctt | 840 |
| ctggctccgg | aagaccccat | attccccatc | atcggagcc | tcttcttgcg | agagctgatc | 900 |
| aaagagtttg | gcacagacca | catctatggg | gccgacactt | tcaatgagat | gcagccacct | 960 |
| tcctcagagc | cctcctatct | tgccgcagcc | accactgccg | tctatgaggc | catgactgca | 1020 |
| gtggatactg | aggctgtgtg | gctgctccaa | ggctggctct | ccagcacca | gccgcagttc | 1080 |
| tgggggcccg | cccagatcag | ggctgtgctg | gagctgtgc | ccgtggccg | cctcctggtt | 1140 |
| ctggacctgt | ttgctgagag | ccagcctgtg | tatacccgca | ctgcctcctt | ccaaggccag | 1200 |
| cccttcatct | ggtgcatgct | gcacaacttt | gggggaaatc | atggtctttt | tggagccttg | 1260 |
| gaggccgtga | acgaggccc | agaagctgcc | cgcctcttcc | ccaactccac | aatggtaggc | 1320 |
| acgggcatgg | ccccccgaggg | catcagccag | aacgaagtgg | tctattccct | catggctgag | 1380 |
| ctgggctggc | gaaaggaccc | agtgccagat | ttggcagcct | gggtgaccag | ctttgccgcc | 1440 |
| cggcggtatg | gggtctccca | cccggacgca | ggggcagcgt | ggaggctact | gctccggagt | 1500 |
| gtgtacaact | gctccgggga | ggcatgcagg | ggccacaatc | gtagcccgct | ggtcaggcgg | 1560 |
| ccgtccctac | agatgaatac | cagcatctgg | tacaaccgat | ctgatgtgtt | tgaggctgg | 1620 |
| cggctgctgc | tcacatctgc | tccctccctg | gccaccagcc | ccgccttccg | ctacgacctg | 1680 |
| ctggacctca | ctcggcaggc | agtgcaggag | ctggtcagct | tgtattatga | ggaggcaaga | 1740 |
| agcgcctatc | tgagcaagga | gctggcctcc | ttgttgaggg | ctggaggcgt | cctgccctat | 1800 |
| gagctgctgc | cggcactgga | cgaggtgctg | gctagtgaca | gccgcttctt | gctgggcagc | 1860 |

```
tggctagagc aggcccgagc agcggcagtc agtgaggccg aggccgattt ctacgagcag    1920
aacagccgct accagctgac cttgtggggg ccagaaggca acatcctgga ctatgccaac    1980
aagcagctgg cggggttggt ggccaactac tacacccctc gctggcggct tttcctggag    2040
gcgctggttg acagtgtggc ccagggcatc ccttttccaa cgcaccagtt tgacaaaaat    2100
gtcttccaac tggagcaggc cttcgttctc agcaagcaga ggtaccccag ccagccgcga    2160
ggagacactg tggacctggc caagaagatc ttcctcaaat attaccccg ctgggtggcc    2220 ggctcttggt gatt                                                     2234

<210> SEQ ID NO 3
<211> LENGTH: 1132
<212> TYPE: DNA
<213> ORGANISM: Chicken

<400> SEQUENCE: 3
gttaagtcct cagacttggc aaggagaatg tagatttcca cagtatatat gttttcacaa      60
aaggaaggag agaaacaaaa gaaaatggca ctgactaaac ttcagctagt ggtataggaa     120
agtaattctg cttaacagag attgcagtga tctctatgta tgtcctgaag aattatgttg     180 tactttttc ccccattttt aaatcaaaca gtgcttaca gaggtcagaa tggtttcttt       240
actgtttgtc aattctatta tttcaataca gaacaatagc ttctataact gaaatatatt     300
tgctattgta tattatgatt gtccctcgaa ccatgaacac tcctccagct gaatttcaca     360
attcctctgt catctgccag gccattaagt tattcatgga agatctttga ggaacactgc     420
aagttcatat cataaacaca tttgaaattg agtattgttt tgcattgtat ggagctatgt     480
tttgctgtat cctcagaata aaagtttgtt ataaagcatt cacacccata aaaagataga     540
tttaaatatt ccaactatag gaaagaaagt gtgtctgctc ttcactctag tctcagttgg     600
ctccttcaca tgcacgcttc tttatttctc ctattttgtc aagaaaataa taggtcaagt     660
cttgttctca tttatgtcct gtctagcgtg gctcagatgc acattgtaca tacaagaagg     720
atcaaatgaa acagacttct ggtctgttac tacaaccata gtaataagca cactaactaa     780
taattgctaa ttatgttttc catctccaag gttcccacat ttttctgttt tcttaaagat     840
cccattatct ggttgtaact gaagctcaat ggaacatgag caatatttcc cagtcttctc     900
tcccatccaa cagtcctgat ggattagcag aacaggcaga aaacacattg ttacccagaa     960
ttaaaaacta atatttgctc tccattcaat ccaaaatgga cctattgaaa ctaaaatcta    1020
acccaatccc attaaatgat ttctatggtg tcaaaggtca aacttctgaa gggaacctgt    1080
gggtgggtca caattcagac tatatattcc ccagggctca gccagtgtct gt            1132

<210> SEQ ID NO 4
<211> LENGTH: 10256
<212> TYPE: DNA
<213> ORGANISM: Artificial Sequence
<220> FEATURE:
<223> OTHER INFORMATION: pSIN-OV-1.1-I-rhNaGlu

<400> SEQUENCE: 4
ggccgcaaga agaaagctga aaaactctgt cccttccaac aagacccaga gcactgtagt      60
atcaggggta aaatgaaaag tatgttatct gctgcatcca gacttcataa aagctggagc     120
ttaattcaga aaaaaaatca gaaagaaatt acactgtgag aacaggtgca attcactttt     180
cctttacaca gagtaatact ggtaactcat ggatgaaggc ttaagggaat gaaattggac     240
tcacagtact gagtcatcac actgaaaaat gcaacctgat acatcagcag aaggtttatg     300
```

-continued

| | | | | | |
|---|---|---|---|---|---|
| ggggaaaaat | gcagccttcc | aattaagcca | gatatctgta | tgaccaagct | gctccagaat | 360 |
| tagtcactca | aaatctctca | gattaaatta | tcaactgtca | ccaaccattc | ctatgctgac | 420 |
| aaggcaattg | cttgttctct | gtgttcctga | tactacaagg | ctcttcctga | cttcctaaag | 480 |
| atgcattata | aaaatcttat | aattcacatt | tctccctaaa | ctttgactca | atcatggtat | 540 |
| gttggcaaat | atggtatatt | actattcaaa | ttgttttcct | tgtacccata | tgtaatgggt | 600 |
| cttgtgaatg | tgctcttttg | ttcctttaat | cataataaaa | acatgtttaa | gcaaacactt | 660 |
| ttcacttgta | gtatttgaag | gtaccggatc | tcgagccgcc | ttcaatgccc | ccaaaaccaa | 720 |
| tccccaggtt | tttaactctc | ccgatttttcc | aagtaccata | gcccgctgag | agagcgccgc | 780 |
| ggtaatggga | tcccaggacc | ccgggaata | taagtctgag | ggggacgtaa | gcaacccttc | 840 |
| cttttgtaac | agggacaaca | tagcccctat | ttccttctta | gaaggagagg | ttttcccgca | 900 |
| ataggtctta | cacgcggacg | aaatcacctt | tatgacggct | tccatgcttg | atccaccggg | 960 |
| cgaccggaat | cacgcagagc | aaccggaatc | acgcctgggg | tggaccgctc | agtcgtcggg | 1020 |
| cttccttccc | gtcttccaac | gactctctga | gttctcggta | gggtatgttg | gcccctgca | 1080 |
| gtagggctcc | ctccgacgcc | actcagcttc | tgccctccta | agccgcagcc | ccctctacta | 1140 |
| gggtcatcgt | ccgctccccg | aataagcgag | acggatgagg | acaggatcgc | cacgccgcct | 1200 |
| gtggccgacc | actattccct | aacgatcacg | tcggggtcac | caaatgaagc | cttctgcttc | 1260 |
| atgcatgtgc | tcgtagtcgt | cagggaatca | acggtccggc | catcaaccca | ggtgcacacc | 1320 |
| aatgtggtga | atggtcaaat | ggcgtttatt | gtatcgagct | aggcacttaa | atacaatatc | 1380 |
| tctgcaatgc | ggaattcagt | ggttcgtcca | atccgtgtta | gacccgtctg | ttgccttcct | 1440 |
| aacaaggcac | gatcatacca | cgatcatacc | accttactcc | caccaatcgg | catgcacggt | 1500 |
| gcttttctc | tccttataag | gcatgttgct | aactcatcgt | tacataagca | tgttgcaaga | 1560 |
| ctacaagagt | attgcataag | actacatttc | ccctccta | tgcaaaagcg | aaactactat | 1620 |
| atcctgaggg | gactcctaac | cgcgtacaac | cgaagcccg | cttttcgcct | aaacatgcta | 1680 |
| ttgtcccctc | agtcaagcct | tgcccgttac | aacccgattc | gcaagccttg | ccctccccac | 1740 |
| attatccgta | gcattatttc | ctagcagtca | tcagagctac | agaagatact | ctatgctgta | 1800 |
| gccaagtcta | caagtttact | attcagcgac | ctcctatatt | ccgcgtgcca | gccgatcaat | 1860 |
| taccaatgcg | cgcttggcgt | aatcatggtc | atagctgttt | cctgtgtgaa | attgttatcc | 1920 |
| gctcacaatt | ccacacaaca | tacgagccgg | aagcataaag | tgtaaagcct | ggggtgccta | 1980 |
| atgagtgagc | taactcacat | taattgcgtt | gcgctcactg | cccgctttcc | agtcgggaaa | 2040 |
| cctgtcgtgc | cagctgcatt | aatgaatcgg | ccaacgcgcg | gggagaggcg | gtttgcgtat | 2100 |
| tgggcgctct | tccgcttcct | cgctcactga | ctcgctgcgc | tcggtcgttc | ggctgcggcg | 2160 |
| agcggtatca | gctcactcaa | aggcggtaat | acggttatcc | acagaatcag | gggataacgc | 2220 |
| aggaaagaac | atgtgagcaa | aaggccagca | aaaggccagg | aaccgtaaaa | aggccgcgtt | 2280 |
| gctggcgttt | ttccataggc | tccgcccccc | tgacgagcat | cacaaaaatc | gacgctcaag | 2340 |
| tcagaggtgg | cgaaacccga | caggactata | aagataccag | gcgtttcccc | ctggaagctc | 2400 |
| cctcgtgcgc | tctcctgttc | cgaccctgcc | gcttaccgga | tacctgtccg | cctttctccc | 2460 |
| ttcgggaagc | gtggcgcttt | ctcatagctc | acgctgtagg | tatctcagtt | cggtgtaggt | 2520 |
| cgttcgctcc | aagctgggct | gtgtgcacga | accccccgtt | cagcccgacc | gctgcgcctt | 2580 |
| atccggtaac | tatcgtcttg | agtccaaccc | ggtaagacac | gacttatcgc | cactggcagc | 2640 |
| agccactggt | aacaggatta | gcagagcgag | gtatgtaggc | ggtgctacag | agttcttgaa | 2700 |

```
gtggtggcct aactacggct acactagaag gacagtattt ggtatctgcg ctctgctgaa      2760
gccagttacc ttcggaaaaa gagttggtag ctcttgatcc ggcaaacaaa ccaccgctgg      2820
tagcggtggt ttttttgttt gcaagcagca gattacgcgc agaaaaaaag gatctcaaga      2880
agatcctttg atcttttcta cggggtctga cgctcagtgg aacgaaaact cacgttaagg      2940
gattttggtc atgagattat caaaaaggat cttcacctag atccttttaa attaaaaatg      3000
aagttttaaa tcaatctaaa gtatatatga gtaaacttgg tctgacagtt accaatgctt      3060
aatcagtgag gcacctatct cagcgatctg tctatttcgt tcatccatag ttgcctgact      3120
ccccgtcgtg tagataacta cgatacggga gggcttacca tctggcccca gtgctgcaat      3180
gataccgcga gacccacgct caccggctcc agatttatca gcaataaacc agccagccgg      3240
aagggccgag cgcagaagtg gtcctgcaac tttatccgcc tccatccagt ctattaattg      3300
ttgccgggaa gctagagtaa gtagttcgcc agttaatagt ttgcgcaacg ttgttgccat      3360
tgctacaggc atcgtggtgt cacgctcgtc gtttggtatg gcttcattca gctccggttc      3420
ccaacgatca aggcgagtta catgatcccc catgttgtgc aaaaaagcgg ttagctcctt      3480
cggtcctccg atcgttgtca gaagtaagtt ggccgcagtg ttatcactca tggttatggc      3540
agcactgcat aattctctta ctgtcatgcc atccgtaaga tgcttttctg tgactggtga      3600
gtactcaacc aagtcattct gagaatagtg tatgcggcga ccgagttgct cttgcccggc      3660
gtcaatacgg gataataccg cgccacatag cagaacttta aaagtgctca tcattggaaa      3720
acgttcttcg gggcgaaaac tctcaaggat cttaccgctg ttgagatcca gttcgatgta      3780
acccactcgt gcacccaact gatcttcagc atcttttact ttcaccagcg tttctgggtg      3840
agcaaaaaca ggaaggcaaa atgccgcaaa aaagggaata agggcgacac ggaaatgttg      3900
aatactcata ctcttccttt ttcaatatta ttgaagcatt tatcagggtt attgtctcat      3960
gagcggatac atatttgaat gtatttagaa aaataaacaa ataggggttc cgcgcacatt      4020
tccccgaaaa gtgccacctg acgcgcccta gcggcgcatt aagcgcggcg ggtgtggt       4080 ggttacgcgc agcgtgaccg ctacacttgc cagcgcccta gcgcccgctc ctttcgcttt      4140
cttcccttcc tttctcgcca cgttcgccgg ctttccccgt caagctctaa atcgggggct      4200
ccctttaggg ttccgattta gtgctttacg gcacctcgac cccaaaaaac ttgattaggg      4260
tgatggttca cgtagtgggc catcgccctg atagacggtt tttcgccctt tgacgttgga      4320
gtccacgttc tttaatagtg gactcttgtt ccaaactgga acaacactca accctatctc      4380
ggtctattct tttgatttat aagggatttt gccgatttcg gcctattggt taaaaaatga      4440
gctgatttaa caaaaattta acgcgaattt taacaaaata ttaacgctta caatttccat      4500
tcgccattca ggctgcgcaa ctgttgggaa gggcgatcgg tgcgggcctc ttcgctatta      4560
cgccagctgg cgaaaggggg atgtgctgca aggcgattaa gttgggtaac gccagggttt      4620
tcccagtcac gacgttgtaa aacgacggcc agtgagcgcg tattccctaa cgatcacgtc      4680
ggggtcacca aatgaagcct tctgcttcat gcatgtgctc gtagtcgtca gggaatcaac      4740
ggtccggcca tcaacccagg tgcacaccaa tgtggtgaat ggtcaaatgg cgtttattgt      4800
atcgagctag gcacttaaat acaatatctc tgcaatgcgg aattcagtgg ttcgtccaat      4860
ccgtccccct ccctatgcaa aagcgaaact actatatcct gagggggactc ctaaccgcgt      4920 acaaccgaag ccccgctttt cgcctaaaca tgctattgtc ccctcagtca agccttgccc      4980
gttacaaccc gattcgcaag ccttgccctc cccacattat ccgtagcatt atttcctagc      5040
agtcatcaga gctacagaag atactctatg ctgtagccaa gtctacaagt ttactattca      5100
```

```
gcgacctcct atattccgcg tgccagccga tcaattacca atccaaccag ctatcacacg    5160
gaatacaaga actcgcctac gctcttcttt cgggctgctt ataagcctcc tgtaatttt     5220 ttatattcct cgttaagtcc tcagacttgg caaggagaat gtagatttcc acagtatata    5280
tgttttcaca aaaggaagga gagaaacaaa agaaaatggc actgactaaa cttcagctag    5340
tggtatagga aagtaattct gcttaacaga gattgcagtg atctctatgt atgtcctgaa    5400
gaattatgtt gtacttttt ccccccatttt taaatcaaac agtgctttac agaggtcaga    5460
atggtttctt tactgtttgt caattctatt atttcaatac agaacaatag cttctataac    5520
tgaaatatat ttgctattgt atattatgat tgtccctcga accatgaaca ctcctccagc    5580
tgaatttcac aattcctctg tcatctgcca ggccattaag ttattcatgg aagatctttg    5640
aggaacactg caagttcata tcataaacac atttgaaatt gagtattgtt ttgcattgta    5700
tggagctatg ttttgctgta tcctcagaat aaaagtttgt tataaagcat tcacacccat    5760
aaaaagatag atttaaatat tccaactata ggaaagaaag tgtgtctgct cttcactcta    5820
gtctcagttg gctccttcac atgcacgctt ctttatttct cctatttgt caagaaaata     5880 ataggtcaag tcttgttctc atttatgtcc tgtctagcgt ggctcagatg cacattgtac    5940
atacaagaag atcaaatga aacagacttc tggtctgtta ctacaaccat agtaataagc     6000
acactaacta ataattgcta attatgtttt ccatctccaa ggttcccaca ttttctgtt     6060 ttcttaaaga tcccattatc tggttgtaac tgaagctcaa tggaacatga gcaatatttc    6120
ccagtcttct ctcccatcca acagtcctga tggattagca gaacaggcag aaaacacatt    6180
gttacccaga attaaaaact aatatttgct ctccattcaa tccaaaatgg acctattgaa    6240
actaaaatct aacccaatcc cattaaatga tttctatggt gtcaaaggtc aaacttctga    6300
agggaacctg tgggtgggtc acaattcaga ctatatattc cccagggctc agccagtgtc    6360
tgtacataca gctagaaagc tgtattgcct ttagcagtca agctcgaaag gtaagcaact    6420
ctctggaatt accttctctc tatattagct cttacttgca cctaaacttt aaaaaattaa    6480
caattattgt gctatgtgtt gtatctttaa gggtgaagta cctgcgtgat acccccctata   6540 aaaacttctc acctgtgtat gcattctgca ctattttatt atgtgtaaaa gctttgtgtt    6600
tgttttcagg aggcttattc tttgtgctta aaatatgttt ttaatttcag aacatcttat    6660
cctgtcgttc actatctgat atgctttgca gtttgcttga ttaacttcta gcccacaga    6720 gtgcacagag agcaaaatca tggtgttcag tgaattctgg ggagttattt taatgtgaaa    6780
attctctaga agtttaattc ctgcaaagtg cagctgctga tcactacaca agataaaaat    6840 gtgggggtg cataaacgta tattcttaca ataatagata catgtgaact tatatacaga     6900
aaagaaaatg agaaaaatgt gtgtgtgtat actcacacac gtggtcagta aaaacttttg    6960
aggggtttaa tacagaaaat ccaatcctga ggccccagca ctcagtacgc atataaaggg    7020
ctgggctctg aaggacttct gactttcaca gattatataa atctcaggaa agcaactaga    7080
ttcatgctgg ctccaaaagc tgtgctttat ataagcacac tggctataca atagttgtac    7140
agttcagctc tttataatag aaacagacag aacaagtata aatcttctat tggtctatgt    7200
catgaacaag aattcattca gtggctctgt tttatagtaa acattgctat tttatcatgt    7260
ctgcatttct cttctgtctg aatgtcacca ctaaaattta actccacaga aagtttatac    7320
tacagtacac atgcatatct ttgagcaaag caaaccatac ctgaaagtgc aatagagcag    7380
aatatgaatt acatgcgtgt ctttctccta gactacatga ccccatataa attacattcc    7440
ttatctattc tgccatcacc aaaacaaagg taaaaatact tttgaagatc tactcatagc    7500
```

```
aagtagtgtg caacaaacag atatttctct acatttattt ttagggaata aaaataagaa    7560
ataaaatagt cagcaagcct ctgctttctc atatatctgt ccaaacctaa agtttactga    7620
aatttgctct ttgaatttcc agttttgcaa gcctatcaga ttgtgtttta atcagaggta    7680
ctgaaaagta tcaatgaatt ctagctttca ctgaacaaaa atatgtagag caactggct     7740
tctgggacag tttgctaccc aaaagacaac tgaatgcaaa tacataaata gatttatgaa    7800
tatggttttg aacatgcaca tgagaggtgg atatagcaac agacacatta ccacagaatt    7860
actttaaaac tacttgttaa catttaattg cctaaaaact gctcgtaatt tactgttgta    7920
gcctaccata gagtaccctg catggtacta tgtacagcat tccatcctta cattttcact    7980
gttctgctgt ttgctctaga caactcagag ttcaccatgg aggcggtggc ggtggccgcg    8040
gcggtggggg tccttctcct ggccggggcc ggggcgcgg caggcgacga ggcccgggag     8100
gcggcggccg tgcgggcgct cgtggcccgg ctgctggggc caggccccgc ggccgacttc    8160
tccgtgtcgg tggagcgcgc tctggctgcc aagccgggct ggacaccta cagcctgggc     8220
ggcggcggcg cggcgcgcgt gcgggtgcgc ggctccacgg gcgtggcagc cgccgcgggg    8280
ctgcaccgct acctgcgcga cttctgtggc tgccacgtgg cctggtccgg ctctcagctg    8340
cgcctgccgc ggccactgcc agccgtgccg ggggagctga ccgaggccac gcccaacagg    8400
taccgctatt accagaatgt gtgcacgcaa agctactctt tcgtgtggtg ggactgggcc    8460
cggtgggagc gagagataga ctggatggcg ctgaatggca tcaacctggc actggcatgg    8520
agcggccagg aggccatctg cagcgggtg tacctggcct tgggcctgac ccaggcagag     8580
atcaatgagt tctttactgg tcctgccttc ttggcatggg ggcgaatggg caacctgcac    8640
acctgggatg gccccctgcc ccctcctgg cacatcaagc agctttatct gcagcaccgg     8700
gtcctgacc agatgcgctc cttcggcatg accccagtgc tgcctgcatt cgcggggcat     8760
gttcccgagg ctgtcaccag ggtgttccct caggtcaatg tcacgaagat gggcagttgg    8820
ggccacttta actgttccta ctcctgctcc ttccttctgg ctccggaaga ccccatattc    8880
cccatcatcg ggagcctctt cttgcgagag ctgatcaaag agtttggcac agaccacatc    8940
tatgggccg acactttcaa tgagatgcag ccaccttcct cagagccctc ctatcttgcc     9000
gcagccacca ctgccgtcta tgaggccatg actgcagtgg atactgaggc tgtgtggctg    9060
ctccaaggct ggctcttcca gcaccagccg cagttctggg ggcccgccca gatcagggct    9120
gtgctgggag ctgtgccccg tggccgcctc ctggttctgg acctgtttgc tgagagccag    9180
cctgtgtata cccgcactgc ctccttccaa ggccagccct tcatctggtg catgctgcac    9240
aactttgggg gaaatcatgg tctttttgga gccttggagg ccgtgaacgg aggcccagaa    9300
gctgcccgcc tcttccccaa ctccacaatg gtaggcacgg gcatggcccc cgagggcatc    9360
agccagaacg aagtggtcta ttccctcatg gctgagctgg gctggcgaaa ggacccagtg    9420
ccagatttgg cagcctgggt gaccagcttt gccgcccggc ggtatggggt ctcccacccg    9480
gacgcagggg cagcgtggag gctactgctc cggagtgtgt acaactgctc cggggaggca    9540
tgcagggggcc acaatcgtag cccgctggtc aggcggccgt ccctacagat gaataccagc    9600
atctggtaca accgatctga tgtgtttgag gcctggcggc tgctgctcac atctgctccc    9660
tccctggcca ccagcccgc cttccgctac gacctgctgg acctcactcg gcaggcagtg    9720
caggagctgg tcagcttgta ttatgaggag caagaagcg cctatctgag caaggagctg     9780
gcctccttgt tgagggctgg aggcgtcctg gcctatgagc tgctgccggc actggacgag    9840
gtgctggcta gtgacagccg cttcttgctg ggcagctggc tagagcaggc ccgagcagcg    9900
```

```
gcagtcagtg aggccgaggc cgatttctac gagcagaaca gccgctacca gctgaccttg    9960
tgggggccag aaggcaacat cctggactat gccaacaagc agctggcggg gttggtggcc   10020
aactactaca cccctcgctg gcggcttttc ctggaggcgc tggttgacag tgtggcccag   10080
ggcatccctt tccaacagca ccagtttgac aaaaatgtct tccaactgga gcaggccttc   10140
gttctcagca agcagaggta ccccagccag ccgcgaggag acactgtgga cctggccaag   10200
aagatcttcc tcaaatatta cccccgctgg gtggccggct cttggtgatt cgaagc       10256
```

<210> SEQ ID NO 5
<211> LENGTH: 12
<212> TYPE: PRT
<213> ORGANISM: Artificial Sequence
<220> FEATURE:
<223> OTHER INFORMATION: Transferrin receptor ligand (TfRL)

<400> SEQUENCE: 5

Thr His Arg Pro Pro Met Trp Ser Pro Val Trp Pro
1               5                   10

RECOMBINANT HUMAN NAGLU PROTEIN AND USES THEREOF

CROSS-REFERENCE TO RELATED APPLICATIONS

This application is related and claims priority to U.S. Provisional Application Ser. No. 61/546,248, filed Oct. 12, 2011, the entire contents of which are expressly incorporated herein by this reference.

BACKGROUND OF THE INVENTION

Sanfilippo Syndrome B is an autosomal recessive lysosomal storage disease (LSD) caused by a deficiency in a lysosomal enzyme known as N-acetyl-alpha-D-glucosaminidase (NaGlu). NaGlu is required for the degradation of heparan sulfate as part of the stepwise breakdown of glycosaminoglycans (GAG) in the lysosome. The deficiency or absence of NaGlu leads to accumulation and urinary excretion of heparan sulfate. With over 70 different mutations identified to date, Sanfilippo Syndrome B exhibits extensive molecular and genetic heterogeneity.

Approximately 1 out of 200,000 births is affected by Sanfilippo Syndrome B and the deficiency mainly manifests in young children. After initial symptom-free interval, patients suffering from Sanfilippo Syndrome B usually present with a slowing of mental development and behavioral problems, followed by progressive intellectual decline resulting in severe mental retardation, dementia and motor disease. Acquisition of speech is slow and incomplete. Profoundly affected patients may present delayed psychomotor and speech development as early as 2 years of age. The disease usually progresses to increasing behavioral disturbance and sleep disturbance. Although the clinical features are mainly neurological, patients often develop diarrhea, carious teeth, an enlarged liver and spleen, stiff joints, hirsteness and/or coarse hair and may exhibit blood-clotting problems. In the final stage of the illness, patients become immobile and unresponsive and develop swallowing difficulties and seizure. The lifespan of an affected child typically does not extend beyond late teens to early twenties.

Different approaches have been attempted to provide the missing enzyme in patients. To produce NaGlu for enzyme replacement therapy (ERT), human NaGlu has been expressed in various mammalian cell culture systems. However, in contrast to the naturally occurring NaGlu which trafficks to the lysosome intracellularly, recombinant NaGlu proteins produced and secreted from mammalian cells were found to contain no or only a trace amount of mannose 6-phosphate (M6P). The absence or scarcity of M6P moieties in the secreted NaGlu has been known to prevent its efficient internalization into target cells (e.g., human skin fibroblasts), which have M6P receptors on the surface on its plasma membrane (see, Zhao et al., *Protein Expression and Purification*, 19:202-211 (2000); and Weber et al., *Protein Expression and Purification*, 21:251-259 (2001)). The low degree of phosphorylation was seen in secreted mouse NaGlu expressed in CHO cells, secreted human NaGlu expressed in HeLa cells, secreted human NaGlu expressed in human fibroblasts, and secreted human NaGlu expressed in human embryonic kidney (HEK) cell line 293 (see, Zhao et al., *Protein Expression and Purification*, 19:202-211 (2000); Yogalingam et al., *Biochim Biophys. Acta* 1502: 415-425; and Weber et al., *Protein Expression and Purification*, 21:251-259 (2001)). No or weak phosphorylation of N-glycans in the NaGlu proteins secreted from the mammalian cells has posed a major obstacle for the development of a recombinant human NaGlu protein suitable for enzyme replacement therapy as all the aforementioned attempts has failed to produce an enzyme which is efficiently taken up by target cells as the concentration of the internalized proteins, if detectable at all, was nearly a thousand times less than wild-type levels (see, Zhao et al., *Protein Expression and Purification*, 19:202-211 (2000)). To date, no approved product is available for the treatment of Sanfilippo Syndrome B.

Direct administration of mammalian cell-produced recombinant human NaGlu protein (rhNaGlu) having the native amino acid sequence into the central nervous system (CNS) (e.g., intrathecal administration into the cerebrospinal fluid (CSF)) of NaGlu deficient mice has been attempted, but failed to demonstrate successful biodistribution of the enzyme to the brain due to excessive accumulation of the protein on the ependymal ling of the ventricles as well as lack of requisite M6P residues for efficient cellular uptake. Similarly, systemic administration (i.e., intravenous (IV) injection) of mammalian cell-produced rhNaGlu having the native amino acid sequence also failed to demonstrate successful localization of the protein to the brain. In addition to known risks associated with highly invasive intrathecal administration, these obstacles in targeting rhNaGlu to the brain have been too great a challenge to achieve effective therapy for the treatment of Sanfilippo Syndrome B.

Therefore, there is a need to provide a stable NaGlu protein which is enzymatically active and has physical properties that allow for the protein to cross the blood brain barrier (BBB) and for effective internalization of the protein into the lysosomes of target cells. There is also a need for a high expressing and robust protein production platform which can provide a recombinant human NaGlu that effectively crosses the blood brain barrier and is efficiently internalized into human target cells.

SUMMARY OF THE INVENTION

The present invention is drawn to compositions comprising recombinant human NaGlu protein (rhNaGlu) useful for therapy, for example, in the treatment of Sanfilippo Syndrome B. The present invention is based on the surprising and unexpected discovery that the rhNaGlu described herein has one or more glycosylation patterns that allow the rhNaGlu to efficiently cross the blood brain barrier (BBB), and be taken up into cells within the central nervous system (CNS) of animals deficient in the enzyme, resulting in a dramatic increase in α-N-acetylglucosaminidase activity in the brain, as well as a reduction of substrate levels. Moreover, the rhNaGlu described herein is efficiently taken up into a mammalian cell (e.g., human cell), resulting in an increased enzymatic activity as compared to NaGlu proteins produced and secreted from unmodified mammalian cells that are not designed to produce specific glycosylation. The increased cellular uptake of the NaGlu protein also provides benefits for the use in enzyme replacement therapy for a human patient suffering from Sanfilippo Syndrome B by minimizing the need for an increased amount and frequency of dose, and thereby greatly reducing the potential risk of immunogenicity.

The rhNaGlu protein described herein contains sufficient amount of oligosaccharides (e.g., mannose and phosphorylated mannose (i.e., M6P)) to allow efficient cellular uptake via mannose and/or M6P receptor-mediated endocytosis and be correctly targeted into human cells. In one embodiment, the rhNaGlu contains at least one mole of protein, for example, 1, 2, 3, 4, 5 or 6 moles of M6P per mole of protein. In one embodiment, rhNaGlu can be internalized into a NaGlu deficient human cell such that the internalized protein fully (100% or more) restores normal levels (i.e., wild-type levels) of NaGlu activity in the NaGlu deficient cell.

Also disclosed herein are methods for producing a transgenic avian that expresses rhNaGlu which benefits from phosphorylation of mannose. In particular, a transgenic avian that expresses rhNaGlu protein in oviduct cells, secretes into the lumen of the oviduct and deposits the protein into egg white. Avian eggs that contain such rhNaGlu are also included in the present invention.

The present invention also contemplates vectors and host cells that contain a transgene encoding rhNaGlu as well as pharmaceutical compositions comprising rhNaGlu to be used in the application of such rhNaGlu for the treatment of Sanfilippo Syndrome B.

In one aspect, the invention provides a composition comprising an isolated mixture of recombinant human N-acetyl-alpha-D-glucosaminidase (rhNaGlu) comprising the amino acid sequence 24-743 of SEQ ID NO:1, wherein at least 10% of the rhNaGlu in the mixture comprises at least one glycan structure having mannose-6-phosphate (M6P). In one embodiment, the rhNaGlu having M6P is capable of being taken up into a mammalian cell deficient in NaGlu such that internalized rhNaGlu restores at least 50%, 60%, 70%, 80%, 90% or 100% of normal NaGlu activity observed in a wild-type mammalian cell of the same type. In another embodiment, the glycan structure is an N-linked glycan.

In one embodiment, the rhNaGlu contains at least 1 mole of M6P per mole of protein. In another embodiment, the rhNaGlu contains between about 1 and about 6 moles of M6P per mole of protein. In another embodiment, the rhNaGlu contains about 2 moles of M6P per mole of protein. In yet another embodiment, the rhNaGlu contains about 3 moles of M6P per mole of protein. In another embodiment, the rhNaGlu contains about 4 moles of M6P per mole of protein. In another embodiment, the rhNaGlu contains about 5 moles of M6P per mole of protein. In yet another embodiment, the rhNaGlu contains about 6 moles of M6P per mole of protein.

In one embodiment, the mammalian cell deficient in NaGlu is a human cell. In another embodiment, the human cell deficient in NaGlu is a skin fibroblast, a hepatocyte or a macrophage. In one embodiment, the human cell deficient in NaGlu is a neuronal cell.

In one embodiment, the rhNaGlu is effectively delivered to the brain of a mammal having NaGlu deficiency when systemically administered. In one particular embodiment, the rhNaGlu is effectively delivered to the brain of a mammal having NaGlu deficiency when intravenously administered. In one embodiment, the rhNaGlu is effectively delivered to the brain of a mammal having NaGlu deficiency when administered intrathecally.

In one embodiment, the rhNaGlu having M6P is internalized by a NaGlu deficient cell and restores at least 100% of normal NaGlu activity in vivo. In one embodiment, the rhNaGlu having M6P contains at least 25 moles of mannose per mole of protein.

In one embodiment, at least 20%, 30%, 40%, 50%, 60%, 70%, 80%, 90% or 95% of the rhNaGlu in the mixture contains M6P. In another embodiment, at least 20% of the rhNaGlu in the mixture contains at least one M6P. In another embodiment, at least 30% of the rhNaGlu in the mixture contains at least one M6P. In another embodiment, at least 40% of the rhNaGlu in the mixture contains at least one M6P. In another embodiment, at least 50% of the rhNaGlu in the mixture contains at least one M6P. In another embodiment, at least 60% of the rhNaGlu in the mixture contains at least one M6P.

In another aspect, the invention provides a composition comprising an isolated mixture of recombinant human N-acetyl-alpha-D-glucosaminidase (rhNaGlu) comprising the amino acid sequence 24-743 of SEQ ID NO:1, wherein the mixture comprises a sufficient amount of rhNaGlu containing one or more glycan structures comprising mannose-6-phosphate (M6P) such that the rhNaGlu containing M6P is internalized into a mammalian cell having NaGlu deficiency via M6P receptor-mediated endocytosis and restores at least 50% of NaGlu activity observed in a wild-type cell of the same type expressing endogenous NaGlu. In one embodiment, the rhNaGlu is N-linked glycosylated. In another embodiment, the rhNaGlu is O-linked glycosylated.

In one embodiment, the rhNaGlu comprises at least 1 moles of M6P per mole of rhNaGlu. In another embodiment, the rhNaGlu comprises about 1, 2, 3, 4, 5 or 6 moles of M6P per mole of rhNaGlu. In another embodiment, the rhNaGlu comprises about 3 moles of M6P per mole of rhNaGlu. In another embodiment, the rhNaGlu comprises about 4 moles of M6P per mole of rhNaGlu.

In one embodiment, the rhNaGlu comprises mannose. In another embodiment, the rhNaGlu comprises N-acetylglucosamine (GlcNAc). In another embodiment, the rhNaGlu comprises galactose. In another embodiment, the rhNaGlu comprises N-acetylgalactosamine (GalNAc). In another embodiment, the rhNaGlu contains no fucose. In another embodiment, the rhNaGlu contains no glucose. In one embodiment, the rhNaGlu restores at least 60, 70, 80, 90, 95 or 100% of normal NaGlu enzymatic activity.

In another embodiment, the rhNaGlu is effectively delivered to the brain of a mammal having NaGlu deficiency when administered systemically. In one embodiment, the rhNaGlu is effectively delivered to the brain of a mammal having NaGlu deficiency when administered intravenously. In another embodiment, the rhNaGlu is effectively delivered to the brain of a mammal having NaGlu deficiency when administered intrathecally.

In one embodiment, the mammalian cell deficient in NaGlu is a human cell. In another embodiment, the human cell is a skin fibroblast, a hepatocyte or a macrophage. In one embodiment, the human cell deficient in NaGlu is a neuronal cell.

In one embodiment, the rhNaGlu is a fusion protein comprising a second moiety. In one embodiment, the second moiety is a polypeptide. In another embodiment, the polypeptide is selected from the group consisting of transferrin receptor ligand (TfRL), insulin-like growth factor receptor (IGF2R) ligand, low density lipoprotein (LDL) receptor ligand and acidic amino acid (AAA) residues.

In one embodiment, the rhNaGlu is produced from a transgenic avian. In one embodiment, the transgenic avian is a chicken, a turkey, a duck or a quail. In one embodiment, the transgenic avian is a chicken. In one embodiment, the rhNaGlu is produced from an oviduct cell.

In another aspect, the invention provides a composition comprising an isolated recombinant human N-acetyl-alpha-D-glucosaminidase (rhNaGlu) comprising one or more glycan structures having sufficient amount of mannose-6-phosphate (M6P) that allows for internalization of the rhNaGlu into a mammalian cell having NaGlu deficiency via M6P receptor-mediated endocytosis, such that when internalized in vivo, the rhNaGlu restores at least 50% of NaGlu activity observed in a wild-type cell of the same type expressing endogenous NaGlu.

In one embodiment, the rhNaGlu protein is N-linked glycosylated. In another embodiment, the rhNaGlu protein is O-linked glycosylated. In one embodiment, the rhNaGlu comprises about 2, 3, 4, 5 or 6 moles of M6P per mole of rhNaGlu.

In one embodiment, the rhNaGlu is effectively delivered to the brain of a mammal having NaGlu deficiency when administered systemically. In another embodiment, the rhNaGlu is effectively delivered to the brain of a mammal having NaGlu deficiency when administered intravenously. In another embodiment, the rhNaGlu is effectively delivered to the brain of a mammal having NaGlu deficiency when administered intrathecally.

In another aspect, the invention provides a transgenic avian comprising a transgene containing a promoter operably linked to a nucleic acid sequence encoding a recombinant human NaGlu (rhNaGlu), wherein the transgene is contained in the genome of the transgenic avian and expressed in an oviduct cell such that the rhNaGlu is glycosylated in the oviduct cell of the transgenic avian, secreted into lumen of oviduct and deposited in egg white of an egg of the transgenic avian.

In one embodiment, the rhNaGlu comprises about 2, 3, 4 or 6 moles of M6P per mole of rhNaGlu. In another embodiment, the promoter component is an oviduct-specific promoter. In another embodiment, the oviduct-specific promoter is an ovalbumin promoter. In yet another embodiment, the transgenic avian is selected from the group consisting of a chicken, a turkey, a duck and a quail.

In another aspect, the invention provides an egg produced by the transgenic avian of the invention.

In yet another aspect, the invention provides a method of producing a recombinant human NaGlu (rhNaGlu) comprising: a) producing a transgenic avian comprising a transgene having a promoter component operably linked to a nucleic acid sequence encoding the rhNaGlu set forth in 24-743 of SEQ ID NO:1, wherein the transgene is contained in the genome of the transgenic avian and expressed in an oviduct cell, such that the rhNaGlu is glycosylated in the oviduct cell of the transgenic avian, secreted into lumen of oviduct and deposited in egg white of an egg laid by the transgenic avian; and b) isolating the rhNaGlu from the egg white.

In one embodiment, the promoter component is an oviduct-specific promoter. In another embodiment, the oviduct-specific promoter is an ovalbumin promoter. In one embodiment, the avian is selected from the group consisting of a chicken, a turkey, a duck and a quail. In one embodiment, the avian is chicken.

In another aspect, the invention provides a vector comprising a nucleotide sequence encoding a human NaGlu operably linked to an ovalbumin promoter. In another aspect, the invention provides a host cell comprising the vector of the invention. In another aspect, the invention provides an isolated nucleic acid comprising the nucleic acid sequence of 5232-10248 of SEQ ID NO:4.

In one aspect, the invention provides a pharmaceutical formulation comprising a composition of the invention in combination with a pharmaceutically acceptable carrier, diluent or excipient.

In another aspect, the invention provides a composition comprising recombinant human NaGlu protein that crosses the blood brain barrier of a mammal having NaGlu deficiency when administered intravenously.

In yet another aspect, the invention provides a method of treating a subject suffering from NaGlu deficiency, the method comprising administering to the subject a therapeutically effective amount of the composition of the invention.

In yet another aspect, the invention provides a method of delivering recombinant human NaGlu protein to the brain of a subject suffering from NaGlu deficiency, the method comprising intravenously administering recombinant human NaGlu protein to the subject.

In another aspect, the invention provides a method of transporting a recombinant human NaGlu protein from the circulation across the blood brain barrier in a therapeutically effective amount, the method comprising intravenously administering a recombinant human NaGlu protein to a subject having NaGlu deficiency.

In one embodiment, the NaGlu deficiency is Sanfilippo Syndrome B. In another embodiment, the subject is a human.

In another embodiment, the recombinant human NaGlu protein is administered intravenously to the subject at a dosage of about 0.5 to about 50 mg/kg body weight. In another embodiment, the recombinant human NaGlu protein is administered intravenously to the subject at a dosage of about 1 to about 30 mg/kg body weight. In another embodiment, the recombinant human NaGlu protein is administered intravenously to the subject at a dosage of about 6 to about 27 mg/kg body weight.

In yet another embodiment, the recombinant human NaGlu protein is intrathecally administered to the subject. In one embodiment, the recombinant human NaGlu protein is intrathecally administered at a dosage of at least about 0.3, 0.4, 0.5, 0.6, 0.7, 0.8, or 0.9 mg/kg body weight. In another embodiment, the recombinant human NaGlu protein is intrathecally administered at a dosage of about 1, 2, 3, 4, 5, 6, 7, 8, 9, or 10 mg/kg body weight. In another embodiment, the recombinant human NaGlu protein is administered intrathecally at a dosage of about 10 to about 30 mg/kg body weight.

In another embodiment, the therapeutically effective amount is an amount effective to reduce heparan sulfate levels in the brain, the kidney, or the liver of the subject. In another embodiment, the therapeutically effective amount is an amount effective to increase NaGlu activity in the brain or the liver of the subject.

In another embodiment, the method further comprises administering a second therapeutic agent. In one embodiment, the second therapeutic is an immunosuppressant.

BRIEF DESCRIPTION OF THE FIGURES

FIG. 1 depicts the amino acid sequence of human recombinant NaGlu (amino acid residues 1-23, signal peptide).

FIG. 2 depicts the nucleic acid sequence (cDNA) of human recombinant NaGlu, including the nucleic acid sequence encoding the signal peptide.

FIG. 3 depicts the nucleic acid sequence of 1.1 kb ovalbumin promoter.

FIGS. 4A-D depict the nucleic acid sequence of pSIN-OV-1.1-1-rhNaGlu vector used in transgenesis of an avian.

DETAILED DESCRIPTION OF THE INVENTION

Figure 5:
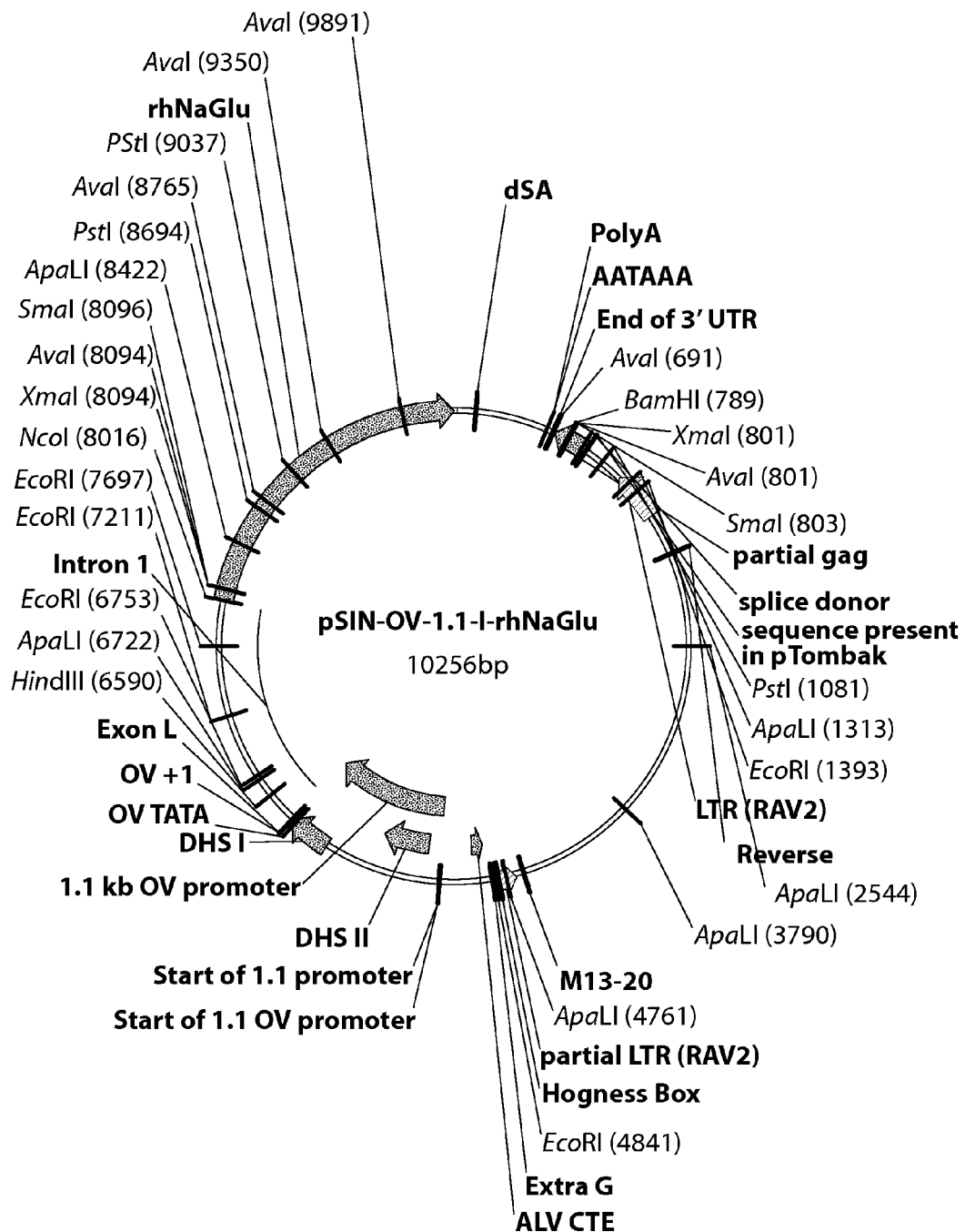
FIG. 5 is a schematic representation of pSIN-OV-1.1-1-rhNaGlu vector.

The present invention provides compositions comprising recombinant human NaGlu protein (rhNaGlu) useful for therapy, for example, in the treatment of NaGlu associated diseases, e.g., Sanfilippo Syndrome B. The present invention is based on a discovery that the rhNaGlu protein described herein contains sufficient amount of oligosaccharides (e.g., mannose and phosphorylated mannose (i.e., M6P)) to allow efficient cellular uptake via mannose and/or M6P receptor-mediated endocytosis and be correctly targeted into human cells. Since the rhNaGlu of the invention is more efficiently taken up into a human cell, the rhNaGlu of the invention exhibits increased enzymatic activity as compared to NaGlu proteins produced and secreted from unmodified mammalian cells that are not designed to produce specific glycosylation. Additionally, the rhNaGlu described herein has one or more glycosylation patterns that allow the rhNaGlu to efficiently cross the blood brain barrier (BBB) when administered intravenously. The increased cellular uptake of the rhNaGlu protein of the invention minimizes the need for large and frequent dosing, thereby greatly reducing the potential risk of immunogenicity.

Some of the definitions and abbreviations used herein include the following: aa, amino acid(s); bp, base pair(s); CDS, coding sequence cDNA, DNA complementary to an RNA; GalNac, N-acetylgalactosamine; Gal, galactose; GlcNac, N-acetylglucosamine; nt, nucleotide(s); kb, 1,000 base pairs; μg, microgram; mL, milliliter; ng, nanogram; and nt, nucleotide.

Certain definitions are set forth herein to illustrate and define the meaning and scope of the various terms used to describe the invention herein.

The term "avian" as used herein refers to any species, subspecies or strain of organism of the taxonomic class ava, such as, but not limited to, chicken, turkey, duck, goose, quail, pheasants, parrots, finches, hawks, crows and ratites including ostrich, emu and cassowary. The term includes the various known strains of *Gallus gallus*, or chickens, (for example, White Leghorn, Brown Leghorn, Barred-Rock, Sussex, N.H., Rhode Island, Ausstralorp, Minorca, Amrox, Calif. Gray, Italian Partridge-colored), as well as strains of turkeys, pheasants, quails, duck, ostriches and other poultry commonly bred in commercial quantities.

The phrases "based on" and "derived from" typically mean obtained from, in whole or in part. For example, a retroviral vector being based on or derived from a particular retrovirus or based on a nucleotide sequence of a particular retrovirus mean that the genome of the retroviral vector contains a substantial portion of the nucleotide sequence of the genome of the particular retrovirus. The substantial portion can be a particular gene or nucleotide sequence such as the nucleotide sequence encoding the gag, pol and/or env proteins or other structural or functional nucleotide sequence of the virus genome such as sequences encoding the long terminal repeats (LTRs) or can be substantially the complete retrovirus genome, for example, most (e.g., more than 60% or more than 70% or more than 80% or more than 90%) or all of the retrovirus genome, as will be apparent from the context in the specification as the knowledge of one skilled in the art. Examples of retroviral vectors that are based on or derived from a retrovirus are the NL retroviral vectors (e.g., NLB) which are derived from the avian leukosis retrovirus ("ALV") as disclosed in Cosset et al., Journal of Virology (1991) vol. 65, p 3388-3394.

The term "coding sequence" and "coding region" as used herein refer to nucleotide sequences and nucleic acid sequences, including both RNA and DNA, that encode genetic information for the synthesis of an RNA, a protein, or any portion of an RNA or protein.

Nucleotide sequences that are not naturally part of a particular organism's genome or are introduced at a non-native site in the organism's genome are referred to as "foreign" nucleotide sequences, "heterologous" nucleotide sequences, "recombinant" nucleotide sequences or "exogenous" nucleotide sequences. In addition, a nucleotide sequence that has been isolated and then reintroduced into the same type (e.g., same species) of organism is not considered to be a naturally occurring part of a particular organism's genome and is therefore considered exogenous or heterologous. "Heterologous proteins" or "exogenous proteins" can be proteins encoded by foreign, heterologous or exogenous nucleotide sequences and therefore are often not naturally expressed in a cell of the host organism.

As used herein, the terms "exogenous," "heterologous" and "foreign" with reference to nucleic acids, such as DNA and RNA, are used interchangeably and refer to nucleic acid that does not occur naturally as part of a chromosome, a genome or cell in which it is present or which is found in a location(s) and/or in amounts that differ from the location(s) and/or amounts in which it occurs in nature. It can be nucleic acid that is not endogenous to the genome, chromosome or cell and has been exogenously introduced into the genome, chromosome or cell. Examples of heterologous DNA include, but are not limited to, DNA that encodes a gene product or gene product(s) of interest, for example, for production of an encoded protein. Examples of heterologous DNA include, but are not limited to, DNA that encodes traceable marker proteins, DNA that encodes therapeutic proteins. The terms "heterologous" and "exogenous" can refer to a biomolecule such as a nucleic acid or a protein which is not normally found in a certain cell, tissue or substance produced by an organism or is not normally found in a certain cell, tissue or substance produced by an organism in an amount or location the same as that found to occur naturally. For example, a protein that is heterologous or exogenous to an egg is a protein that is not normally found in the egg.

The term "construct" as used herein refers to a linear or circular nucleotide sequence such as DNA that has been assembled from more than one segments of nucleotide sequence which have been isolated from a natural source or have been chemically synthesized, or combinations thereof.

The term "complementary" as used herein refers to two nucleic acid molecules that can form specific interactions with one another. In the specific interactions, an adenine base within one strand of a nucleic acid can form two hydrogen bonds with thymine within a second nucleic acid strand when the two nucleic acid strands are in opposing polarities. Also in the specific interactions, a guanine base within one strand of a nucleic acid can form three hydrogen bonds with cytosine within a second nucleic acid strand when the two nucleic acid strands are in opposing polarities. Complementary nucleic acids as referred to herein, can further comprise modified bases wherein a modified adenine may form hydrogen bonds with a thymine or modified thymine, and a modified cytosine may form hydrogen bonds with a guanine or a modified guanine.

The term "expressed" or "expression" as used herein refers to the transcription of a coding sequence to yield an RNA molecule at least complementary in part to a region of one of the two nucleic acid strands of the coding sequence. The term "expressed" or "expression" as used herein can also refer to the translation of an mRNA to produce a protein or peptide.

The term "expression vector" as used herein refers to a nucleic acid vector that comprises a gene expression controlling region, such as a promoter or promoter component, operably linked to a nucleotide sequence encoding at least one polypeptide.

The term "fragment" as used herein can refer to, for example, an at least about 10, 20, 50, 75, 100, 150, 200, 250, 300, 500, 1000, 2000, 5000, 6,000, 8,000, 10,000, 20,000, 30,000, 40,000, 50,000 or 60,000 nucleotide long portion of a nucleic acid that has been constructed artificially (e.g., by chemical synthesis) or by cleaving a natural product into multiple pieces, using restriction endonucleases or mechanical shearing, or enzymatically, for example, by PCR or any other polymerizing technique known in the art, or expressed in a host cell by recombinant nucleic acid technology known to one of skill in the art. The term "fragment" as used herein can also refer to, for example, an at least about 5, 10, 15, 20, 25, 30, 40, or 50 amino acid residues less than a full length amino acid sequence for NaGlu (i.e., amino acid sequence 24-743 of SEQ ID NO:1), which portion is cleaved from a naturally occurring amino acid sequence by proteolytic cleavage by at least one protease, or is a portion of the naturally occurring amino acid sequence synthesized by chemical methods or using recombinant DNA technology (e.g., expressed from a portion of the nucleotide sequence encoding the naturally occurring amino acid sequence) known to one of skill in the art. "Fragment" may also refer to a portion, for example, of about 50%, about 60%, about 70%, about 80%, about 90%, about 95% or about 99% of a particular nucleotide sequence or amino acid sequence.

"Functional portion" and "functional fragment" can be used interchangeably and as used herein mean a portion or fragment of a whole capable of performing, in whole or in part, a function of the whole. For example, a biologically functional portion of a molecule means a portion of the molecule that performs a biological function of the whole or intact molecule. Functional portions may be of any useful size. For example, a functional fragment may range in size from about 20 bases in length to a length equal to the entire length of the specified sequence minus one nucleotide. In another example, a functional fragment may range in size from about 50 bases in length to a length equal to the entire length of the specified sequence minus one nucleotide. In another example, a functional fragment may range in size from about 50 bases in length to about 20 kb in length. In another example, a functional fragment may range in size from about 500 bases in length to about 20 kb in length. In another example, a functional fragment may range in size from about 1 kb in length to about 20 kb in length. In another example, a functional fragment may range in size from about 0.1 kb in length to about 10 kb in length. In another example, a functional fragment may range in size from about 20 bases kb in length to about 10 kb in length.

The term "fully transgenic" or "germline transgenic" refers to an animal such as an avian that contains at least one copy of a transgene in essentially all of its cells.

The term "gene expression controlling region" as used herein refers to nucleotide sequences that are associated with a coding sequence and which regulate, in whole or in part, expression of the coding sequence, for example, regulate, in whole or in part, the transcription of the coding sequence. Gene expression controlling regions may be isolated from a naturally occurring source or may be chemically synthesized and can be incorporated into a nucleic acid vector to enable regulated transcription in appropriate cells. The "gene expression controlling regions" may precede, but is not limited to preceding, the region of a nucleic acid sequence that is in the region 5' of the end of a coding sequence that may be transcribed into mRNA.

As used herein, "host cells" refers to cells that harbor vectors constructed using recombinant DNA techniques and encoding at least one heterologous gene.

The term "isolated nucleic acid" as used herein covers, for example, (a) a DNA which has the sequence of part of a naturally occurring genomic molecule but is not flanked by at least one of the sequences that flank that part of the molecule in the genome of the species in which it naturally occurs; (b) a nucleic acid which has been incorporated into a vector or into the genomic DNA of a prokaryote or eukaryote in a manner such that the resulting vector or genomic DNA is not identical to naturally occurring DNA from which the nucleic acid was obtained; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, i.e., a gene encoding a fusion protein, and (e) a recombinant nucleotide sequence that is part of a hybrid sequence that is not naturally occurring. Isolated nucleic acid molecules of the present invention can include, for example, natural allelic variants as well as nucleic acid molecules modified by nucleotide deletions, insertions, inversions, or substitutions.

The term "nucleic acid" as used herein refers to any linear or sequential array of nucleotides and nucleosides, for example cDNA, genomic DNA, mRNA, tRNA, oligonucleotides, oligonucleosides and derivatives thereof. For ease of discussion, non-naturally occurring nucleic acids may be referred to herein as constructs. Nucleic acids can include bacterial plasmid vectors including expression, cloning, cosmid and transformation vectors such as, animal viral vectors such as, but not limited to, modified adenovirus, influenza virus, polio virus, pox virus, retroviruses such as avian leukosis virus (ALV) retroviral vector, a murine leukemia virus (MLV) retroviral vector, and a lentivirus vector, and the like and fragments thereof. In addition, the nucleic acid can be an LTR of an avian leukosis virus (ALV) retroviral vector, a murine leukemia virus (MLV) retroviral vector, or a lentivirus vector and fragments thereof. Nucleic acids can also include NL vectors such as NLB, NLD and NLA and fragments thereof and synthetic oligonucleotides such as chemically synthesized DNA or RNA. Nucleic acids can include modified or derivatized nucleotides and nucleosides such as, but not limited to, halogenated nucleotides such as, but not only, 5-bromouracil, and derivatized nucleotides such as biotin-labeled nucleotides.

As used herein, the terms "glycan," "glycan structure," "glycan moiety," "oligosaccharide," "oligosaccharide structure," "glycosylation pattern," "glycosylation profile," and "glycosylation structure" have essentially the same meaning and each refers to one or more structures which are formed from sugar residues and are attached to glycosylated protein such as human NaGlu. For example, "N-glycan" or "N-linked glycan" refers to a glycan structure attached to a nitrogen of asparagine or arginine side-chain of the glycosylated protein. "O-glycan" or "O-linked glycan" refers to a glycan structure attached to the hydroxyl oxygen of serine, threonine, tyrosine, hydroxylysine, or hydroxyproline side chain of the glycosylate protein.

The term "vector" and "nucleic acid vector" as used herein refers to a natural or synthetic single or double stranded plasmid or viral nucleic acid molecule that can be transfected or transformed into cells and replicate independently of, or within, the host cell genome. A circular double stranded vector can be linearized by treatment with an appropriate restriction enzyme based on the nucleotide sequence of the vector. A nucleic acid can be inserted into a vector by cutting the vector with restriction enzymes and ligating the desired pieces together, as is understood in the art. A typical vector can be comprised of the following elements operatively linked at appropriate distances for allowing functional gene expression: replication origin, promoter, enhancer, 5' mRNA leader sequence, ribosomal binding site, nucleic acid cassette, termination and polyadenylation sites, and selectable marker sequences. One or more of these elements can be omitted in specific applications. The nucleic acid cassette can include a restriction site for insertion of the nucleic acid sequence to be expressed. In a functional vector the nucleic acid cassette contains the nucleic acid sequence to be expressed including translation initiation and termination sites. An intron optionally can be included in the construct, for example, 5' to the coding sequence. A vector is constructed so that the particular coding sequence is located in the vector with the appropriate regulatory sequences, the positioning and orientation of the coding sequence with respect to the control sequences being such that the coding sequence is transcribed under the "control" of the control or regulatory sequences. Modification of the sequences encoding the particular protein of interest can be desirable to achieve this end. For example, in some cases it can be necessary to modify the sequence so that it can be attached to the control sequences with the appropriate orientation, or to maintain the reading frame. The control sequences and other regulatory sequences can be ligated to the coding sequence prior to insertion into a vector. Alternatively, the coding sequence can be cloned directly into an expression vector which already contains the control sequences and an appropriate restriction site which is in reading frame with and under regulatory control of the control sequences.

The term "operably linked" refers to an arrangement of elements wherein the components so described are configured so as to perform their usual function. Gene expression controlling regions or promoter(s) (e.g., promoter components) operably linked to a coding sequence are capable of effecting the expression of the coding sequence. The controlling sequence(s) or promoter need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

"Overexpression", as used herein, refers to the production of a gene product in transgenic organisms that exceeds levels of production in normal or non-transformed organisms.

The term "oviduct" or "oviduct tissue" refers to a tissue of an avian oviduct, such as the magnum, e.g., tubular gland cells, where proteins are produced with N-linked oligosaccharides that contain increased amounts of mannose and mammose-6-phosphate (M6P) and substantially reduced amounts of galactose and/or sialic acid relative to that of proteins produced in other tissue of the avian such as liver or kidney tissue.

The term "oviduct-specific promoter" as used herein refers to promoters and promoter components which are functional, i.e., provide for transcription of a coding sequence, to a large extent, for example, primarily (i.e., more than 50% of the transcription product produced in the animal by a particular promoter type being produced in oviduct cells) or exclusively in oviduct cells of a bird. Examples of oviduct specific promoters include, but are not limited to, ovalbumin promoter, ovomucoid promoter, ovoinhibitor promoter, lysozyme promoter and ovotransferrin promoter and functional portions of these promoters, e.g., promoter components. By limiting the expression of NaGlu protein to the magnum using oviduct specific promoters, deleterious physiological effects to the bird as result of expression of these enzymes in other tissues of the bird can be minimized.

The terms "percent sequence identity," "percent identity," "% identity," "percent sequence homology," "percent homology," "% homology" and "percent sequence similarity" can each refer to the degree of sequence matching between two nucleic acid sequences or two amino acid sequences. Such sequence matching can be determined using the algorithm of Karlin & Altschul (1990) Proc. Natl. Acad. Sci. 87: 2264-2268, modified as in Karlin & Altschul (1993) Proc. Natl. Acad. Sci. 90: 5873-5877. Such an algorithm is incorporated into the NBLAST and XBLAST programs of Altschul et al. (1990) T. Mol. Biol. Q15: 403-410. BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference amino acid sequence. To obtain gapped alignments for comparison purposes, Gapped BLAST is utilized as described in Altschul et al. (1997) Nucl. Acids Res. 25: 3389-3402. When utilizing BLAST and Gapped BLAST programs, the default parameters of the respective programs (e.g., XBLAST and NBLAST) are used. Other algorithms, programs and default settings may also be suitable such as, but not only, the GCG-Sequence Analysis Package of the U.K. Human Genome Mapping Project Resource Centre that includes programs for nucleotide or amino acid sequence comparisons. A sequence may be at least 50%, 60%, 70%, 75%, 80%, 85%, 90%, 91%, 92%, 93%, 94%, 95%, 96%, 97%, 98%, 99% or more identical to another sequence, e.g., the NaGlu protein sequence identified herein.

The term "avian derived" refers to a composition or substance produced by or obtained from a bird, poultry or avian. "Avian" refers to birds that can be kept as livestock, including but not limited to, chickens, duck, turkey, quail and ratites. For example, "avian derived" can refer to chicken derived, turkey derived and/or quail derived.

The terms "polynucleotide," "oligonucleotide", "nucleotide sequence" and "nucleic acid sequence" can be used interchangeably herein and include, but are not limited to, coding sequences, i.e., polynucleotide(s) or nucleic acid sequence(s) which are transcribed and translated into polypeptide in vitro or in vivo when placed under the control of appropriate regulatory or control sequences; controlling sequences, e.g., translational start and stop codons, promoter sequences, ribosome binding sites, polyadenylation signals, transcription factor binding sites, transcription termination sequences, upstream and downstream regulatory domains, enhancers, silencers, DNA sequences to which a transcription factor(s) binds and alters the activity of a gene's promoter either positively (induction) or negatively (repression) and the like. No limitations as to length or to synthetic origin are suggested by the terms described herein.

As used herein the terms "polypeptide" and "protein" refer to a polymer of amino acids, for example, three or more amino acids, in a serial array, linked through peptide bonds. The term "polypeptide" includes proteins, protein fragments, protein analogues, oligopeptides and the like. The term "polypeptides" includes polypeptides as defined above that are encoded by nucleic acids, produced through recombinant technology (e.g., isolated from a transgenic bird), or synthesized. The term "polypeptides" further contemplates polypeptides as defined above that include chemically modified amino acids or amino acids covalently or noncovalently linked to labeling ligands.

The term "promoter" as used herein refers to a DNA sequence useful to initiate transcription by an RNA polymerase in an avian cell. A "promoter component" is a DNA sequence that can, by itself or in combination with other DNA sequences, effect or facilitate transcription. Promoter components can be functional fragments of promoters.

The terms "recombinant nucleic acid" and "recombinant DNA" as used herein refer to combinations of at least two nucleic acid sequences that are not naturally found in a eukaryotic or prokaryotic cell. The nucleic acid sequences may include, but are not limited to, nucleic acid vectors, gene expression regulatory elements, origins of replication, suitable gene sequences that when expressed confer antibiotic resistance, protein-encoding sequences and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

As used herein, the term "regulatory" sequences or elements include promoters, enhancers, terminators, stop codons, and other elements that can control gene expression.

A "retrovirus", "retroviral particle," "transducing particle," or "transduction particle" refers to a replication-defective or replication-competent virus capable of transducing non-viral DNA or RNA into a cell.

A "SIN vector" refers to a self-inactivating vector. In particular, a SIN vector is a retroviral vector having an altered genome such that upon integration into genomic DNA of the target cell (e.g., avian embryo cells), the 5' LTR of the integrated retroviral vector will not function as a promoter. For example, a portion or all of the nucleotide sequence of the retroviral vector that results in the U3 region of the 5' LTR of the retroviral vector once integrated can be deleted or altered in order to reduce or eliminate promoter activity of the 5' LTR. In certain examples, deletion of the CAAT box and/or the TAATA box from U3 of the 5' LTR can result in a SIN vector, as is understood in the art.

The term "sense strand" as used herein refers to a single stranded DNA molecule from a genomic DNA that can be transcribed into RNA and translated into the natural polypeptide product of the gene. The term "antisense strand" as used herein refers to the single strand DNA molecule of a genomic DNA that is complementary with the sense strand of the gene.

A "therapeutic protein" or "pharmaceutical protein" is a substance that, in whole or in part, makes up a drug. In particular, "therapeutic proteins" and "pharmaceutical proteins" include an amino acid sequence which in whole or in part makes up a drug.

The terms "promoter," "transcription regulatory sequence" and "promoter component" as used herein refer to nucleotide which regulates the transcriptional expression of a coding sequence. Exemplary transcription regulatory sequences include enhancer elements, hormone response elements, steroid response elements, negative regulatory elements, and the like. The "transcription regulatory sequence" can be isolated and incorporated into a vector to enable regulated transcription in appropriate cells of portions of the vector DNA. The "transcription regulatory sequence" can precede, but is not limited to, the region of a nucleic acid sequence that is in the region 5' of the end of a protein coding sequence that is transcribed into mRNA. Transcriptional regulatory sequence can also be located within a protein coding region, for example, in regions of a gene that are identified as "intron" regions.

The terms "transformation" and "transfection" as used herein refer to the process of inserting a nucleic acid into a host. Many techniques are well known to those skilled in the art to facilitate transformation or transfection of a nucleic acid into a prokaryotic or eukaryotic organism. These methods involve a variety of techniques, such as treating the cells with certain concentrations of salt, for example, but without limitation, a calcium or magnesium salt, or exposing the cells to an electric field, detergent, or liposome material, to render the host cell competent for the uptake of the nucleic acid molecules.

As used herein, a "transgenic animal" is any non-human animal, such as an avian species, including the chicken, in which one or more of the cells of the animal contain heterologous nucleic acid introduced by way of human intervention, such as by transgenic techniques known in the art (see, for example, U.S. patent publication No. 2007/0243165, published Oct. 18, 2007, the disclosure of which is incorporated in its entirety herein by reference) including those disclosed herein. The nucleic acid is introduced into an animal, directly or indirectly by introduction into a cell (e.g., egg or embryo cell) by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule can be integrated within a chromosome, or it may be extrachromosomally replicating DNA. In the typical transgenic animal, the transgene can cause cells to express a recombinant form of the target protein or polypeptide. The terms "chimeric animal" or "mosaic animal" are used herein to refer to animals in which a transgene is found, or in which the recombinant nucleotide sequence is expressed, in some but not all cells of the animal. A germ-line chimeric animal contains a transgene in its germ cells and can give rise to an offspring transgenic animal in which most or all cells of the offspring will contain the transgene.

As used herein, the term "transgene" means a nucleic acid sequence (encoding, for example, a human NaGlu protein) that is partly or entirely heterologous, i.e., foreign, to the animal or cell into which it is introduced, or, is partly or entirely homologous to an endogenous gene of the transgenic animal or cell into which it is introduced, but which is designed to be inserted, or is inserted, into the animal or cell genome in such a way as to alter the genome of the organism into which it is inserted (e.g., it is inserted at a location which differs from that of the natural gene or its insertion results in a knockout).

As used herein, the term "enzyme replacement therapy (ERT)" refers to a therapeutic strategy for correcting an enzyme deficiency in a subject by administering the missing enzyme to a subject. For lysosomal enzyme replacement therapy to be effective, the therapeutic enzyme must be delivered to lysosomes in the appropriate cells in tissues where the storage defect is manifested. In one embodiment, the enzyme may be administered to the subject intravenously, intrathecally, intracerebrally, intraventricularly, or intraparenchymaly. In one embodiment, the enzyme is able to cross the blood brain barrier (BBB). Without intending to be limited by mechanism, it is believed that as the blood perfuses patient tissues, enzyme is taken up by cells and transported to the lysosome, where the enzyme acts to eliminate material that has accumulated in the lysosomes due to the enzyme deficiency.

I. Composition of NaGlu

The present invention provides novel compositions of recombinant human NaGlu (rhNaGlu or NaGlu) (amino acid sequence 24-743 set forth in SEQ ID NO:1) having patterns of glycosylation that confer an increased cellular uptake and an increased subcellular activity which are particularly useful for therapy, for example, in the treatment of Sanfilippo Syndrome B (mucopolysaccharidosis (MPS) IIIB).

In some aspects, the composition can be an isolated mixture of rhNaGlu comprising the amino acid sequence 24-743 of SEQ ID NO:1. In one embodiment, the mixture contains a sufficient amount of rhNaGlu having at least one glycan structure that contains phosphorylated mannose (e.g., M6P) or mannose such that the rhNaGlu containing M6P or mannose is internalized into a human cell deficient in NaGlu and restores at least 50% of NaGlu activity observed in a wild-type human cell of the same type that actively expresses endogenous NaGlu. In one aspect, at least 10%, 20%, 30%, 40%, 50%, 60%, 70%, 80%, 90%, 91%, 92%, 93% 94%, 95%, 96%, 97%, 98% or 99% of rhNaGlu in the mixture contains at least one glycan structure having phosphorylated mannose and/or mannose. In one embodiment, at least 10% of rhNaGlu in the mixture contains at least one glycan structure having phosphorylated mannose and/or mannose. In one embodiment, at least 20% of rhNaGlu in the mixture contains at least one glycan structure having phosphorylated mannose and/or mannose. In one embodiment, at least 30% of rhNaGlu in the mixture contains at least one glycan structure having phosphorylated mannose and/or mannose. In one embodiment, at least 30% of rhNaGlu in the mixture contains at least one glycan structure having phosphorylated mannose and/or mannose. In one embodiment, at least 40% of rhNaGlu in the mixture contains at least one glycan structure having phosphorylated mannose and/or mannose. In one embodiment, at least 50% of rhNaGlu in the mixture contains at least one glycan structure having phosphorylated mannose and/or mannose. In one embodiment, at least 60% of rhNaGlu in the mixture contains at least one glycan structure having phosphorylated mannose and/or mannose.

In some aspects, the NaGlu contains one or more N-linked glycan structure. The NaGlu contains at least one phosphorylated mannose (e.g., M6P or bis-M6P) which allows the protein to be recognized by the Mannose 6-phosphate receptor (M6P receptor), and subsequently taken up into a human cell, including but not limited to, a skin fibroblast, an endothelial, a neuronal cell, a hepatocyte, a macrophage or any cell that expresses M6P receptor on the cell surface via M6P receptor-mediated endocytosis. In one embodiment, the NaGlu contains at least one mannose (Man). In another embodiment, the NaGlu contains at least one N-acetylglucosamine (GlcNAc).

In some aspects, the NaGlu contains a glycan structure comprising a phosphorylated mannose (M6P). As used herein, M6P can encompass any phosphorylated mannose residue and includes mono- and bis-phosphorylated mannose. In one embodiment, the M6P is present at a concentration that is about 1, about 2, about 3, about 4, about 5 or about 6 mole(s) per mole of protein. In one embodiment, the NaGlu contains M6P at a concentration that is about 2, about 3, about 4, or about 5 moles per mole of protein. In one embodiment, the NaGlu contains M6P at a concentration that is about 2 moles per mole of protein. In one embodiment, the NaGlu contains M6P at a concentration that is about 3 moles per mole of protein. In one embodiment, the NaGlu contains M6P at a concentration that is about 4 moles per mole of protein. In one embodiment, the NaGlu contains M6P at a concentration that is about 5 moles per mole of protein. In one embodiment, the NaGlu contains M6P at a concentration that is about 6 moles per mole of protein.

In some aspects, the rhNaGlu contains a sufficient amount of M6P for cellular uptake into a human cell having a M6P receptor on the cell surface via M6P receptor-mediated endocytosis. In one embodiment, a sufficient amount of M6P for uptake into a human cell is about 1, 2, 3, 4, 5 or 6 moles per mole of protein. The rhNaGlu can be internalized into a human cell deficient in NaGlu such that the internalized protein fully (100% or more) restores a normal level of NaGlu activity in the human cell deficient in NaGlu. In one embodiment, the internalized rhNaGlu protein fully restores a normal level of NaGlu activity in the human cell at a concentration that is at least 0.5, 0.6, 0.7, 0.8, 0.9 or 1.0 µg/mL. In one embodiment, the internalized protein fully restores a normal level of NaGlu activity in the human cell deficient in NaGlu at a concentration that is at least 2, 3, 4, 5, 6, 7, 8, 9 or 10 µg/mL. In one embodiment, the internalized protein fully restores a normal level of NaGlu activity in the human cell at a concentration that is at least 20, 30, 40, 50, 60, 70, 80, 90 or 100 µg/mL. As used herein, the normal level of NaGlu activity is a level of NaGlu activity measured in a wild-type human cell of the same type that actively expresses a normal NaGlu enzyme.

In some aspects, the rhNaGlu can be internalized into a human cell deficient in NaGlu such that the protein restores at least about 50%, about 60%, about 70%, about 80%, about 90% or about 95% of NaGlu activity of a normal human cell of the same type. In some embodiments, the rhNaGlu can be internalized into a human cell deficient in NaGlu such that the internalized rhNaGlu provides a higher enzymatic activity than that observed in a normal human cell of the same type. In one embodiment, the rhNaGlu is internalized into a human cell deficient in NaGlu such that the internalized rhNaGlu provides about 2, about 3, about 4, about 5, about 6, about 7, about 8, about 9 and about 10-fold higher activity than that observed in a normal human cell of the same type. In one embodiment, the rhNaGlu is internalized into a human cell deficient in NaGlu such that the internalized rhNaGlu provides about 15, about 20, about 25, about 30, about 40, about 50, about 60, about 70, about 80, about 90 or about 100-fold higher activity than that observed in a normal human cell.

In one embodiment, the human cell deficient in NaGlu is any human cell deficient in NaGlu that expresses one or more M6P receptors on the cell surface. In one embodiment, the human cell deficient in NaGlu is a human mucopolysaccharidosis (MPS) IIIB fibroblast that accumulates heparan sulfate. In one embodiment, the human cell deficient in NaGlu is a hepatocyte. In one embodiment, the human cell deficient in NaGlu is a neuronal cell. In one embodiment, the human cell deficient in NaGlu is an endothelial cell. In one embodiment, the human cell deficient in NaGlu is a macrophage.

In some aspects, uptake of rhNaGlu into a human cell is inhibited by the presence of about 1, about 2, about 3, about 4, about 5, about 6, about 7, about 8, about 9 or about 10 mM of competing M6P monosaccharide. In some aspects, the cellular uptake of rhNaGlu is inhibited by the presence of about 0.1, about 0.2, about 0.3, about 0.4, about 0.5, about 0.6, about 0.7, about 0.8, about 0.9 or about 1.0 mM of M6P monosaccharide. In one embodiment, the cellular uptake of rhNaGlu is inhibited by the presence of about 0.01, about 0.02, about 0.03, about 0.04, about 0.05, about 0.06, about 0.07, about 0.08, or about 0.09 mM of M6P monosaccharide.

In some aspects, the rhNaGlu contains mannose in its glycan structures at a concentration that is about 17, 18, 19, 20, 21, 22, 23, 24, 25, 26, 27, 28, 29, 30, 31, 32, 33, 34 or 35 moles per mole of protein. In one embodiment, the rhNaGlu has mannose at a concentration that is about 20, 21, 22, 23, 24, 25, 26, 27, 28, 29 or 30 moles per mole of protein. The rhNaGlu contains mannose at a concentration that is about 22, 23, 24, 25, 26, 27 or 28 moles per mole of protein. The rhNaGlu contains mannose at a concentration that is about 24 moles per mole of protein. The rhNaGlu protein contains mannose at a concentration that is about 25 moles per mole of protein. The rhNaGlu contains mannose at a concentration that is about 26 moles per mole of protein. The rhNaGlu contains mannose at a concentration that is about 27 moles per mole of protein. In one embodiment, the rhNaGlu has mannose at a concentration that is between about 20 and about 30 moles per mole of protein.

In some aspects, the rhNaGlu comprises N-acetylglucosamine (GlcNAc). In one embodiment, the rhNaGlu contains GlcNAc at a concentration that is between about 28 and about 42 moles per mole of protein. In one embodiment, the NaGlu protein has GlcNAc at a concentration that is between about 30 and about 40 moles per mole of protein. In one embodiment, the NaGlu protein comprises GlcNAc at a concentration that is between about 32 and about 38 moles per mole of protein. In one embodiment, the NaGlu protein comprises GlcNAc at a concentration that is between about 34 and about 36 moles per mole of protein. In one embodiment, the NaGlu protein has GlcNAc at a concentration that is about 35 moles per mole of protein. In one embodiment, the rhNaGlu protein contains GlcNAc at a concentration that is about 30, 31, 32, 33, 34, 35, 36, 37, 38, 39 or 40 moles per mole of protein.

In some aspects, the rhNaGlu contains N-acetylgalactosamine (GalNAc) and/or galactose (Gal). The presence of the GalNAc and Gal typically indicates that the NaGlu may contain one or more O-linked glycan structures which are added to the protein in the Golgi compartment. Accordingly, the present invention optionally includes a composition comprising a recombinant human NaGlu that contains one or more O-linked glycan structure.

In one embodiment, the rhNaGlu contains galactose at a concentration that is about 1, 2, 3, 4, 5, 6 or 7 moles per mole of protein. In one embodiment, the rhNaGlu has galactose at a concentration that is about 2, 3, 4, 5 or 6 moles per mole of protein.

In one embodiment, the rhNaGlu has galactose at a concentration that is about 3 moles per mole of protein. In one embodiment, the rhNaGlu has galactose at a concentration that is about 4 moles per mole of protein.

In one embodiment, the NaGlu comprises at least one GalNAc molecule per mole of protein. In one embodiment, the NaGlu comprises GalNAc at a concentration that is about 1 or 2 moles per mole of protein.

In one embodiment, the NaGlu contains no fucose. In yet another embodiment, the NaGlu contains no glucose. In yet another embodiment, rhNaGlu contains neither fucose nor glucose.

The present invention also contemplates compositions of modified rhNaGlu proteins produced from modified nucleic sequences of rhNaGlu. The modified nucleic acid sequences include deletions, insertions, or substitutions of different nucleotides resulting in a polynucleotide that encodes a functionally equivalent polynucleotide or polypeptide. The encoded protein may also contain deletions, insertions, or substitutions of amino acid residues that produce a silent change and result in a functionally equivalent protein or polypeptide. Deliberate amino acid substitutions can be made on the basis of similarity in polarity, charge, solubility, hydrophobicity, hydrophilicity, and/or the amphipathic nature of the residues as long as the biological activity of the NaGlu is retained. For example, negatively charged amino acids can include aspartic acid and glutamic acid; positively charged amino acids can include lysine and arginine; and amino acids with uncharged polar head groups having similar hydrophilicity values can include leucine, isoleucine, and valine; glycine and alanine; asparagine and glutamine; serine and threonine; phenylalanine and tyrosine.

In other aspects, the rhNaGlu can be modified such that it contains an additional moiety or second peptide. Although unmodified NaGlu protein may cross the blood brain barrier at a high serum concentration, modifications of the protein can be performed to increase the efficiency of central nervous system (CNS) targeting. In one embodiment, transferrin receptor ligand (TfRL) can be attached to human NaGlu at N- or C-terminus of NaGlu protein. A non-limiting example of TrRL is THRPPMWSPVWP (SEQ ID NO:5). In one embodiment, the transferrin receptor ligand can be attached to human NaGlu C-terminus of the NaGlu protein. In another embodiment, human NaGlu is fused to insulin-like growth factor receptor (IGF2R) ligand at N- or C-terminus of the NaGlu protein. In yet another embodiment, the NaGlu protein is fused to low density lipoprotein (LDL) receptor ligand at N- or C-terminus of the NaGlu protein. In one embodiment, the NaGlu protein is fused to a stretch of five to ten consecutive acidic amino acid residues. The acidic amino acid residues can include aspartic acid (D) or glutamic acid (E).

In one embodiment, the rhNaGlu is produced in a transgenic avian that contains a transgene encoding the NaGlu protein. In one embodiment, the rhNaGlu is produced in an oviduct cell (e.g., a tubular gland cell) of a transgenic avian (e.g., chicken (Gallus)). In one embodiment, the rhNaGlu is glycosylated in the oviduct cell (e.g., tubular gland cell) of the transgenic avian. In one embodiment, the rhNaGlu has a glycosylation pattern resulting from the rhNaGlu being produced in an oviduct cell of a transgenic avian. In one embodiment, the rhNaGlu can be isolated and purified from the content of the hard shell eggs laid by the transgenic avian. In one embodiment, the rhNaGlu can be isolated and purified from egg white of the transgenic avian.

The present invention also includes compositions of an isolated mixture of NaGlu proteins, such as a mixture of one or more fragments and full-length rhNaGlu (e.g., 24-743 set forth in SEQ ID NO:1). In one embodiment, a substantial portion of the mixture contains phosphorylated M6P. In one embodiment, at least 10%, 20%, 30%, 40%, 50%, 60%, 70%, 80%, 85%, 90% 95%, 97%, 98% or 99% of the rhNaGlu in the mixture contains M6P. In yet another embodiment, at least 50% of the isolated rhNaGlu in the mixture contains M6P. In yet another embodiment, at least 60% of the isolated rhNaGlu in the mixture contains M6P. In yet another embodiment, at least 70% of the isolated rhNaGlu in the mixture contains M6P. In yet another embodiment, at least 80% of the isolated rhNaGlu in the mixture contains M6P. In yet another embodiment, at least 90% of the isolated rhNaGlu in the mixture contains M6P. In yet another embodiment, at least 95% of the isolated rhNaGlu in the mixture contains M6P. In yet another embodiment, at least 96% of the isolated rhNaGlu in the mixture contains M6P. In yet another embodiment, at least 97% of the isolated rhNaGlu in the mixture contains M6P. In yet another embodiment, at least 98% of the isolated rhNaGlu in the mixture contains M6P. In yet another embodiment, at least 99% of the isolated rhNaGlu in the mixture contains M6P.

Optionally, the rhNaGlu protein produced from an avian or mammalian expression system (e.g., CHO, HEK293, or human skin fibroblast cell-line) can be further modified to achieve a favorable glycosylation pattern (i.e., an increased amount of M6P) for cellular uptake while retaining the biological activity. Additional terminal M6P can be introduced to the rhNaGlu by the general methods applied to other hydrolases as described in U.S. Pat. No. 6,679,165, U.S. Pat. No. 7,138,262, or U.S. Publication No. 2009/0022702, the entire teachings of each of which are incorporated herein by reference. For example, a highly phosphorylated mannopyranosyl oligosaccharide compound can be derivatized with a chemical compound containing a carbonyl-reactive group, followed by oxidizing the rhNaGlu protein to generate carbonyl (aldehyde) group on one glycan structure of the protein, and reacting the oxidized NaGlu protein with the glycan with the derivatized highly phosphorylated mannopyranosyl oligosaccharide compound to form a new compound having hydrazine bond.

II. Vectors

Methods which are well-known to those skilled in the art can be used to construct expression vectors containing sequences encoding NaGlu and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y., the entire teachings of which are incorporated herein by reference.

Figure 11:
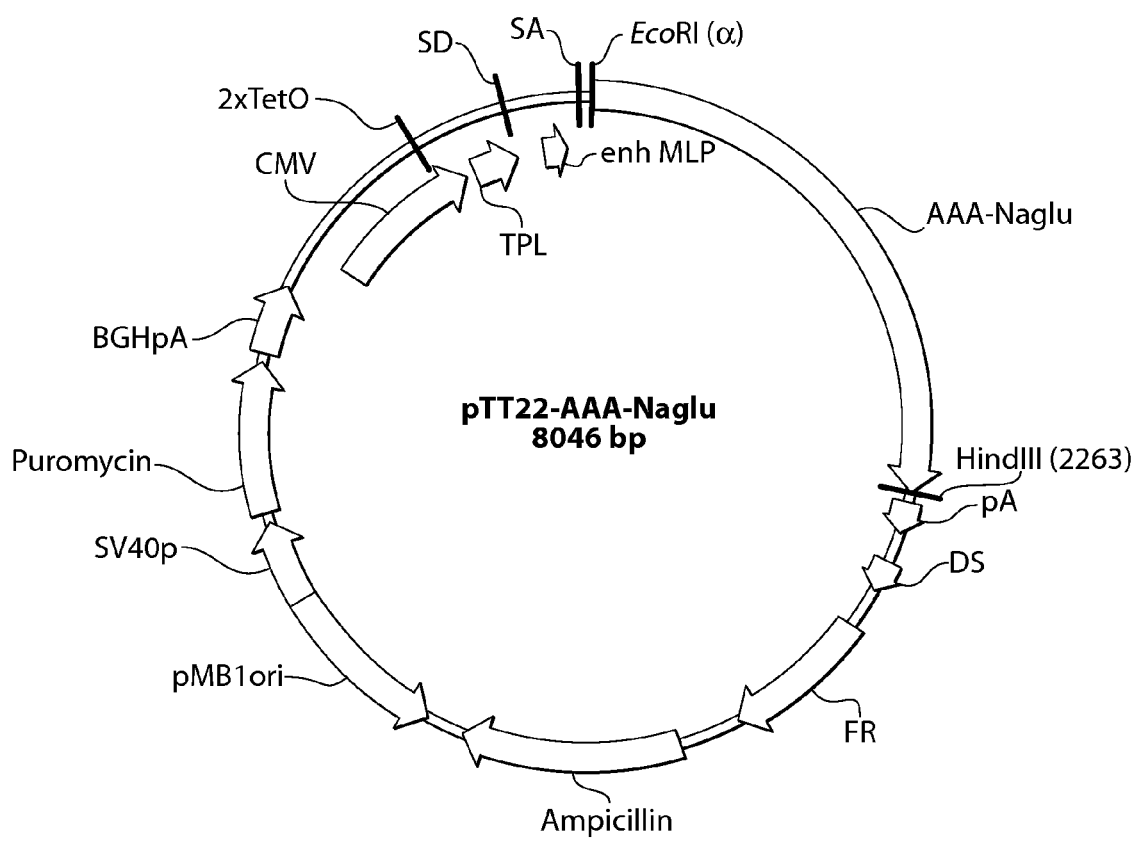
FIG. 11 depicts a schematic representation of pTT22 vector containing a recombinant human NaGlu fusion construct (AAA-NaGlu: acidic amino acid residues fused to N-terminus of the full length NaGlu).
Figure 12:
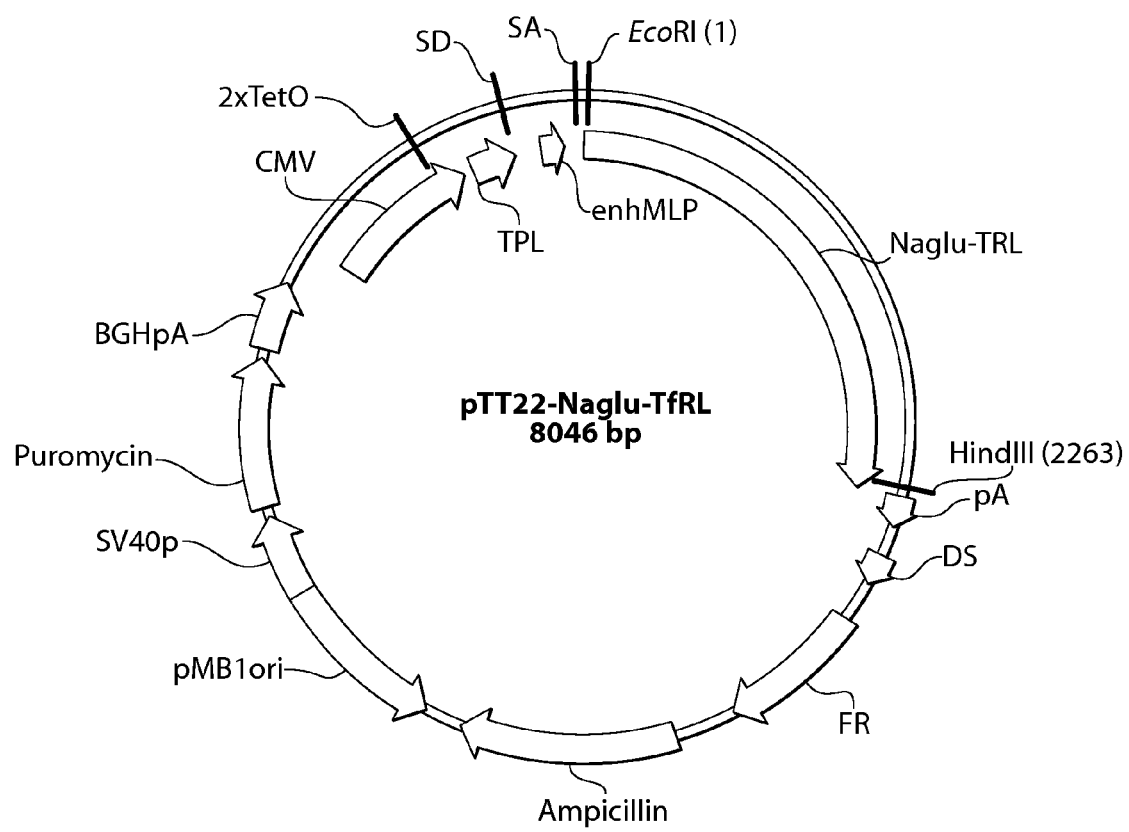
FIG. 12 depicts a schematic representation of pTT22 vector containing a recombinant human NaGlu fusion construct (NaGlu-TfRL: transferrin receptor ligand fused to C-terminus of the full length NaGlu).

A variety of expression vector/host systems can be utilized to express nucleic acid sequences encoding rhNaGlu. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus) or with bacterial expression vectors (e.g., Ti or pBR322 plasmids); or mammalian cell culture systems (e.g., pTT22 vector). Non-limiting examples of the pTT22 vector containing human NaGlu cDNA fused to a nucleic acid sequence encoding acidic amino acid residue and TfRL are shown in FIGS. 11 and 12.

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by vertebrate (e.g., avian or mammalian) cells have a signal peptide or secretory leader sequence which is cleaved from the mature protein once export of the growing protein chain across the rough endoplasmic reticulum (ER) has been initiated. Those of ordinary skill in the art are aware that polypeptides produced in the ER by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., the MEAVA-VAAAVGVLLLAGAGGAAG (1-23 of SEQ ID NO:1) signal peptide of human NaGlu is used, or a functional derivative of that sequence that retains the ability to direct the secretion of the polypeptide that is operably associated with it. Alternatively, a heterologous signal peptide (e.g., a heterologous mammalian or avian signal peptide), or a functional derivative thereof, may be used. For example, the wild-type leader sequence may be substituted with the leader sequence of, for example, human tissue plasminogen activator (tPA) or mouse β-glucuronidase.

The control elements or regulatory sequences can includes those non-translated regions of the vector-enhancers, promoters, 5' and 3' untranslated regions that interact with host cellular proteins to carry out transcription and translation. Such elements can vary in their strength and specificity. Depending on the vector system and host cell utilized, any number of suitable transcription and translation elements can be used. For example, when cloning in bacterial systems, inducible promoters such as the hybrid lac-Z promoter of the Bluescript™ phagemid (Stratagene, LaJolla, Calif.) or pSport1™ plasmid (Gibco BRL) and the like can be used. In mammalian cell systems, promoters from mammalian genes or from mammalian viruses are preferred. If it is necessary to generate a cell line that contains multiple copies of the sequence encoding NaGlu, vectors based on SV40 or EBV can be also used with an appropriate selectable marker such as puromycin and ampicillin (see, e.g., FIGS. 11 and 12).

When the rhNaGlu is produced in a transgenic avian, the present invention contemplates that the rhNaGlu sequence be placed downstream of a promoter such that the sequence encoding the rhNaGlu can be expressed in a tissue-specific manner in a transgenic avian. For example, the promoter can be an oviduct-specific promoter that is largely, but not entirely, specific to the magnum, such as the oviduct-specific promoter, including but not limited to, ovalbumin, lysozyme, conalbumin, ovomucoid, ovomucoid, ovomucin and ovotransferrin promoters. In one embodiment, the promoter is an ovalbumin promoter, a lysozyme promoter, a conalbumin promoter, an ovomucoid promoter, an ovomucin promoter and/or an ovotransferrin promoter or any functional portion thereof.

Alternatively, a constitutive promoter can be used to express the coding sequence of human NaGlu in an avian. In this case, expression is not limited to the magnum; expression also occurs in other tissues within the avian (e.g., blood). The use of such a transgene, which includes a constitutive promoter and the coding sequence of NaGlu, is also suitable for effecting or driving the expression of a protein in the oviduct and the subsequent secretion of the protein into the egg. In one embodiment, the constitutive promoter can be, for example, a cytomegalovirus (CMV) promoter, a rous-sarcoma virus (RSV) promoter, a murine leukemia virus (MLV) promoter, and β-actin promoter. In one embodiment, the promoter is a CMV promoter, a MDOT promoter, a RSV promoter, a MLV promoter, or a mouse mammary tumor virus (MMTV) promoter of any functional portion thereof.

The invention also contemplates any useful fragment or component of the promoters described herein. The promoter can be at least one segment, fragment or component of a promoter region, such as a segment of the ovalbumin, lysozyme, conalbumin, ovomucoid, ovomucin, ovotransferrin, CMV, RSV or MLV promoter region. In a preferred embodiment, the promoter is a segment of the oviduct-specific promoter region which contains essential elements to direct expression of the coding sequence in the tubular gland cells. For example, included in the scope of the present invention is a segment, portion or fragment of an oviduct-specific promoter and/or condensing the critical regulatory elements of the oviduct-specific promoter so that it retains sequences required for expression in the tubular gland cells of the magnum of the oviduct. In one embodiment, a segment of the ovalbumin promoter region is used. This segment comprises the 5'-flanking region of the ovalbumin gene.

A vector that contains a coding sequence for human NaGlu can be used for transfecting blastodermal cells of an avian or mammalian cell to generate stable integrations into the avian or mammalian genome and to create a germline transgenic avian or mammalian cell line. A non-limiting example of such vector is shown in FIGS. 4A-D and 5. In the avian expression system, the human NaGlu coding sequence is operably linked to a promoter in a positional relationship to express the coding sequence in a transgenic avian, particularly in the tubular gland cell of the magnum of the avian oviduct, such that the recombinant human NaGlu protein is expressed and deposited in egg white of a hard shell egg laid by the transgenic avian. Additional suitable vectors and methods to making vectors for expressing rhNaGlu in an avian system are also disclosed in U.S. Pat. No. 6,730,822; U.S. Pat. No. 6,825,396; U.S. Pat. No. 6,875,588; U.S. Pat. No. 7,294,507; U.S. Pat. No. 7,521,591; U.S. Pat. No. 7,534,929; U.S. Publication No. 2008/0064862A1; and U.S. Patent Publication No. 2006/0185024, the entire teachings of which are incorporated herein by reference. Non-limiting examples of other promoters which can be also useful in the present invention include Pol III promoters (for example, type 1, type 2 and type 3 Pol III promoters) such as H1 promoters, U6 promoters, tRNA promoters, RNase MPR promoters and functional portions of each of these promoters. Typically, functional terminator sequences are selected for use in the present invention in accordance with the promoter that is employed.

In one embodiment, the vector is a retroviral vector, in which the coding sequence and the promoter are both positioned between the 5' and 3' LTRs of the retroviral vector. In one useful embodiment, the LTRs or retroviral vector is derived from an avian leukosis virus (ALV), a murine leukemia virus (MLV) or a lentivirus. One useful retrovirus for randomly introducing a transgene into the avian genome is the replication-deficient ALV, the replication-deficient MLV, or the replication-deficient lentivirus.

The present invention also contemplates the use of self-inactivating (SIN) vectors. SIN vectors can be useful for increasing the quantity of human NaGlu produced in the oviduct of a transgenic avian. This effect can be further enhanced when the SIN vector does not contain any selectable marker cassette with a functional promoter (SIN/SC negative vector). In one embodiment, a SIN vector is a retroviral vector having altered genome so that the 5' LTR of the integrated retroviral vector does not function as a promoter. In one particular embodiment, a portion or all of the nucleotide sequence of the retroviral vector that results in the U3 region of the 5' LTR of the retroviral vector once integrated can be deleted or altered in order to reduce or eliminate promoter activity of the 5' LTR. A non-limiting example of SIN vector which contains an ovalbumin promoter region fused to the coding sequence of human rhNaGlu is shown in FIGS. 4A-D and 5. Functional components of the vector are also tabulated in Table 1.

TABLE 1

Functional components in pSIN-OV-1.1kb-I-rhNaGlu

| Functional components | Nucleotide Sequence in SEQ ID NO: 4 |
| --- | --- |
| poly A site | 634-639 |
| Partial gag | 692-945 |
| LTR (RAV2) | 1243-1588 |
| Partial LTR (RAV2) | 4691-4863 |
| ALV CTE | 4899-4986 |
| 1.1 kb Ovalbumin promoter | 5232-6363 |
| DHS II | 5334-5714 |
| DHS I | 6064-6364 |
| Exon L | 6364-6410 |
| Intron 1 | 6411-7999 |
| NaGlu | 8017-10248 |

Any of the vectors described herein can include a sequence encoding a signal peptide that directs secretion of the protein expressed by the vector's coding sequence from, for example, the tubular gland cells of the oviduct of an avian. Where a recombinant human NaGlu protein would not otherwise be secreted, the vector containing the coding sequence is modified to comprise a DNA sequence comprising about 60 bp encoding a signal peptide from, for example, the lysozyme gene. The DNA sequence encoding the signal peptide is inserted in the vector such that it is located at the N-terminus of the rhNaGlu protein encoded by the DNA.

Further, the coding sequences of vectors used in any of the methods of the present invention can be provided with a 3' untranslated region (3' UTR) to confer stability to the RNA produced. When a 3' UTR is added to a retroviral vector, the orientation of the promoter, the coding sequence and the 3' UTR is preferably reversed with respect to the direction of the 3' UTR, so that the addition of the 3' UTR does not interfere with transcription of the full-length genomic RNA. In one embodiment, the 3' UTR may be that of the ovalbumin gene, lysozyme gene or any 3' UTR that is functional in a magnum cell, i.e., the SV40 late region.

III. Transgenic Avians

Transgenes described herein can be introduced into avian embryonic blastodermal cells to produce a transgenic chicken, transgenic turkey, transgenic quail and other avian species that carry the transgene encoding recombinant human NaGlu in the genome of its germ-line tissue. In one aspect of the invention, a transgenic avian that produces rhNaGlu is created by transduction of embryonic blastodermal cells with replication-defective or replication-competent retroviral particles carrying the transgene between the 5' and 3' LTRs of the retroviral vector. For instance, an avian leukosis virus (ALV) retroviral vector or a murine leukemia virus (MLV) retroviral vector can be used. An RNA copy of the modified retroviral vector packaged into viral particles can be used to infect embryonic blastoderms which develop into transgenic avians.

By the methods of the present invention, transgenes can be introduced into embryonic blastodermal cells of various avian species. For example, the methods can be applied to produce a transgenic chicken, transgenic turkey, transgenic quail, transgenic duct, and other avian species, that carry the transgene in the genome of its germ-line tissue in order to produce proteins of the invention. The blastodermal cells are typically stage VII-XII cells as defined by Eyal-Giladi and Kochav (1976), or the equivalent thereof. In a preferred embodiment, the blastoderm cells are at or near stage X.

In one method of transfecting blastodermal cells, a packaged retroviral-based vector can be used to deliver the vector into embryonic blastodermal cells so that the vector is integrated into the avian genome. Such viral particles (i.e., transduction particles) are produced for the vector and titered to determine the appropriate concentration that can be used to inject embryos. In one embodiment, avian eggs are windowed according to the procedure described in U.S. Pat. No. 5,897,998, the disclosure of which is incorporated herein by reference in its entirety, and the eggs are injected with transducing particles at or near stage X.

The transgenic avians of the invention which produce rhNaGlu are developed from the blastodermal cells into which the vector has been introduced. The resulting embryo is allowed to develop and the chick allowed to mature. At this stage, the transgenic avian produced from blastodermal cells is known as a founder and is chimeric with respect to the cells carrying the transgene and is referred to G0. G0 founder avians are typically chimeric for each inserted transgene. That is, only some of the cells of the G0 transgenic bird contain the transgene. Some founders carry the transgene in tubular gland cells in the magnum of their oviducts. These avians express the rhNaGlu protein encoded by the transgene in their oviducts. The NaGlu protein may also be expressed in other tissues (e.g., blood) in addition to the oviduct. Some founders are germ-line founders that carry the transgene in the genome of the germ-line tissues, and may also carry the transgene in oviduct magnum tubular gland cells that express the exogenous protein.

The transgenic avian can carry the transgene in its germline providing transmission of the exogenous transgene to the avian's offspring stably in a Mendelian fashion. The G0 generation is typically hemizygous for the transgene encoding rhNaGlu. The G0 generation can be bred to non-transgenic animals to give rise to G1 transgenic offspring which are also hemizygous for the transgene and contain the transgene in essentially all of the bird's cells. The G1 hemizygous offspring can be bred to non-transgenic animals giving rise to G2 hemizygous offspring or may be bred together to give rise to G2 offspring homozygous for the transgene. Substantially all of the cells of avians which are positive for the transgene that are derived from G1 offspring contain the transgene. In one embodiment, hemizygotic G2 offspring from the same line can be bred to produce G3 offspring homozygous for the transgene. In another embodiment, hemizygous G0 or G1 animals, for example, are bred together to give rise to homozygous G1 offspring containing two copies of the transgene(s) in each cell of the animal. These are merely examples of certain useful breeding methods and the present invention contemplates the employment of any useful breeding method such as those known to individuals of ordinary skill in the art.

IV. Production of rhNaGlu

The rhNaGlu can be produced using a transgenic avian that contains in the genome a transgene encoding rhNaGlu. In one embodiment, the transgenic avian is a germline transgenic chicken, quail, duck or turkey. In one particularly useful embodiment, the invention is drawn to the production of NaGlu which can be produced in the oviduct of a chicken.

Production of rhNaGlu with or without modification in the avian system (e.g., in the avian oviduct) is within the scope of the invention. In one embodiment, the unmodified rhNaGlu comprises the wild-type amino acid sequence (24-743 of SEQ ID NO:1) with a glycosylation structure (i.e., M6P) that enables efficient uptake by human cells. In another embodiment, the modified protein can be an rhNaGlu fusion protein having a glycosylation pattern (i.e., M6P) that enables efficient uptake by human cells.

A suitable avian vector that contains a nucleic acid sequence encoding a NaGlu protein, operably linked to a tissue-specific or constitutive promoter that drives expression of the encoding sequence in the chicken oviduct are introduced into chicken embryonic cells at or near stage X as described herein. The transformed embryonic cells are incubated under conditions conducive to hatching live chicks. Live chicks are nurtured into a mature chimeric chicken which are mated with a non-transgenic chicken naturally or via artificial insemination. A transgenic chicken is identified by screening progeny for germline incorporation of the protein encoding sequence. The transgenic progeny can be mated with another transgenic or a non-transgenic chicken to produce a fully germline transgenic hen that lays eggs.

The rhNaGlu can be produced in a tissue-specific manner. For example, rhNaGlu can be expressed in the oviduct, blood and/or other cells or tissues of the transgenic avian. In one embodiment, the NaGlu is expressed in the tubular gland cells of the magnum of the oviduct of the transgenic avian, secreted into the lumen of the oviduct, and deposited into egg white. In one embodiment, egg white containing rhNaGlu is harvested and stored in bulk at a temperature ranging from 4° C. to −20° C. The NaGlu is then isolated and purified from the contents of the eggs using various methods known in the art.

One aspect of the present invention relates to avian hard shell eggs (e.g., chicken hard shell eggs) which contain the rhNaGlu protein. The rhNaGlu produced and secreted by the transgenic avian is glycosylated in a manner favorable to cellular uptake by a human cell. The protein may be present in any useful amount. In one embodiment, the protein is present in an amount in a range between about 0.01 µg per hard-shell egg and about 1 gram per hard-shell egg. In another embodiment, the protein is present in an amount in a range of between about 1 µg per hard-shell egg and about 1 gram per hard-shell egg. For example, the protein may be present in an amount in a range of between about 10 µg per hard-shell egg and about 1 gram per hard-shell egg (e.g., a range of between about 10 µg per hard-shell egg and about 400 milligrams per hard-shell egg).

In one embodiment, the rhNaGlu is present in the egg white of the egg. In one embodiment, the rhNaGlu is present in an amount in a range of between about 1 ng per milliliter of egg white and about 0.2 gram per milliliter of egg white. For example, the rhNaGlu may be present in an amount in a range of between about 0.1 µg per milliliter of egg white and about 0.2 gram per milliliter of egg white (e.g., the rhNaGlu may be present in an amount in a range of between about 1 µg per milliliter of egg white and about 100 milligrams per milliliter of egg white. In one embodiment, the rhNaGlu is present in an amount in a range of between about 1 µg per milliliter of egg white and about 50 milligrams per milliliter of egg white. For example, the rhNaGlu may be present in an amount in a range of about 1 µg per milliliter of egg white and about 10 milligrams per milliliter of egg white (e.g., the rhNaGlu may be present in an amount in a range of between about 1 µg per milliliter of egg white and about 1 milligrams per milliliter of egg white). In one embodiment, the rhNaGlu is present in an amount of more than 0.1 µg per milliliter of egg white. In one embodiment, the rhNaGlu is present in an amount of more than 0.5 µg per milliliter of egg white. In one embodiment, the rhNaGlu is present in an amount of more than 1 µg per milliliter of egg white. In one embodiment, the protein is present in an amount of more than 1.5 µg per milliliter of egg white. In one embodiment, the rhNaGlu is present in an amount of more than 0.5 µg per milliliter of egg white. In one embodiment, the protein is present in an amount of more than 0.1 µg per milliliter of egg white.

In one embodiment, the rhNaGlu is present in an amount of 20 mg/L, 30 mg/L, 40 mg/L, 50 mg/L, 60 mg/L, 70 mg/L, 80 mg/L, 90 mg/L, 100 mg/L, 120 mg/L, 130 mg/L, 140 mg/L, 150 mg/L, 160 mg/L, 170 mg/L, 200 mg/L, 300 mg/L, 400 mg/L, 500 mg/L, 600 mg/L, 700 mg/L, 800 mg/L, 900 mg/L, or 1,000 mg/L egg white. In one embodiment, the rhNaGlu is present in an amount of about 100 mg/L of egg white. In one embodiment, the rhNaGlu is present in an amount of about 200 mg/L of egg white.

V. Host Cells

The present invention also contemplates rhNaGlu produced in any useful protein expression system including, without limitation, cell culture (e.g., avian cells, CHO cells, HEK293 cells and COS cells), yeast, bacteria, and plants.

A host cell strain can be chosen for its ability to modulate the expression of the inserted sequences or to process the expressed NaGlu in the desired fashion. Such modifications of the polypeptide of NaGlu include, without limitation, glycosylation, phosphorylation, or lipidation. Different host cells such as CHO, COS, HeLa, MDCK, HEK293 and W138, which have specific cellular machinery and characteristic mechanisms for such post-translational activities, can be chosen to ensure the correct modification and processing of the fusion protein of the present invention. An avian tumor cell line is also contemplated as a host cell for expressing the polypeptide of the present invention. Examples of a useful avian cell line (e.g., an avian oviduct tumor cell line) are described in U.S. Pat. Publication No. 2009/0253176, the entire teachings of which are incorporated herein by reference.

VI. Pharmaceutical Compositions

The present invention also features pharmaceutical compositions comprising isolated and substantially purified rhNaGlu or a pharmaceutically acceptable salt thereof. The recombinant human NaGlu proteins may be administered using one or more carriers, e.g., as part of a pharmaceutical formulation, or without a carrier. The carrier(s) must be "acceptable" in the sense of being compatible with the other ingredients of the formulation and not deleterious to the recipient thereof. Compositions comprising such carriers, including composite molecules, are formulated by well-known conventional methods (see, for example, Remington's Pharmaceutical Sciences, 14th Ed., Mack Publishing Co., Easton, Pa.), the entire teachings of which are incorporated herein by reference. The carrier may comprise a diluent. In one embodiment, the pharmaceutical carrier can be a liquid and the protein may be in the form of a solution. The pharmaceutical carrier can be wax, fat, or alcohol. In another embodiment, the pharmaceutically acceptable carrier may be a solid in the form of a powder, a lyophilized powder, or a tablet. In one embodiment, the carrier may comprise a liposome or a microcapsule.

In some embodiments, a pharmaceutical composition comprising recombinant human NaGlu protein further comprises a buffer. Exemplary buffers include acetate, phosphate, citrate and glutamate buffers. Exemplary buffers also include lithium citrate, sodium citrate, potassium citrate, calcium citrate, lithium lactate, sodium lactate, potassium lactate, calcium lactate, lithium phosphate, sodium phosphate, potassium phosphate, calcium phosphate, lithium maleate, sodium maleate, potassium maleate, calcium maleate, lithium tartarate, sodium tartarate, potassium tartarate, calcium tartarate, lithium succinate, sodium succinate, potassium succinate, calcium succinate, lithium acetate, sodium acetate, potassium acetate, calcium acetate, and mixtures thereof. In some embodiments, the buffer is trisodium citrate dihydrate. In some embodiments, the buffer is citric acid monohydrate. In some embodiments, a pharmaceutical composition comprises trisodium citrate dehydrate and citric acid monohydrate.

In some embodiments, a pharmaceutical composition comprising recombinant human NaGlu protein further comprises a stabilizer. Exemplary stabilizers include albumin, trehalose, sugars, amino acids, polyols, cyclodextrins, salts such as sodium chloride, magnesium chloride, and calcium chloride, lyoprotectants, and mixtures thereof. In some embodiments, a pharmaceutical composition comprises human serum albumin.

In some embodiments, it is desirable to add a surfactant to the pharmaceutical composition. Exemplary surfactants include nonionic surfactants such as Polysorbates (e.g., Polysorbates 20 or 80); poloxamers (e.g., poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; and the MONAQUAT™ series (Mona Industries, Inc., Paterson, N.J.), polyethyl glycol, polypropyl glycol, and copolymers of ethylene and propylene glycol (e.g., Pluronics, PF68, etc). Typically, the amount of surfactant added is such that it reduces aggregation of the protein and minimizes the formation of particulates or effervescences. For example, a surfactant may be present in a formulation at a concentration from about 0.001-0.5% (e.g., about 0.005-0.05%, or 0.005-0.01%). In particular, a surfactant may be present in a formulation at a concentration of approximately 0.005%, 0.01%, 0.02%, 0.1%, 0.2%, 0.3%, 0.4%, or 0.5%, etc. Ranges and values intermediate to the above recited ranges and values are also contemplated to be part of the invention.

In some embodiments, suitable pharmaceutical compositions of the invention may further include one or more bulking agents, in particular, for lyophilized formulations. A "bulking agent" is a compound which adds mass to the lyophilized mixture and contributes to the physical structure of the lyophilized cake. For example, a bulking agent may improve the appearance of lyophilized cake (e.g., essentially uniform lyophilized cake). Suitable bulking agents include, but are not limited to, sodium chloride, lactose, mannitol, glycine, sucrose, trehalose, hydroxyethyl starch. Exemplary concentrations of bulking agents are from about 1% to about 10% (e.g., 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, and 10.0%). Ranges and values intermediate to the above recited ranges and values are also contemplated to be part of the invention. The pharmaceutical compositions can be in the form of a sterile lyophilized powder for injection upon reconstitution with a diluent. The diluent can be water for injection, bacteriostatic water for injection, or sterile saline. The lyophilized powder may be produced by freeze drying a solution of the fusion protein to produce the protein in dry form. As is known in the art, the lyophilized protein generally has increased stability and a longer shelf-life than a liquid solution of the protein.

Pharmaceutical formulations include those suitable for oral, rectal, nasal, topical (including buccal and sub-lingual), vaginal or parenteral administration. Preferably, the pharmaceutical formulations of the invention include those suitable for administration by injection including intrathecal, intraparenchymal, intracerebral, intraventricular, intramuscular, sub-cutaneous and intravenous administration. In one embodiment, the formulations of the invention are suitable for intravenous administration. In another embodiment, the formulations of the invention are suitable for intrathecal administration. The pharmaceutical formulations of the invention also include those suitable for administration by inhalation or insufflation. The formulations can, where appropriate, be conveniently presented in discrete dosage units and can be prepared by any of the methods well known in the art of pharmacy. The methods of producing the pharmaceutical formulations typically include the step of bringing the therapeutic proteins into association with liquid carriers or finely divided solid carriers or both and then, if necessary, shaping the product into the desired formulation.

Recombinant human NaGlu proteins of the invention can also be formulated for parenteral administration (e.g., by injection, for example bolus injection or continuous infusion) and can be presented in unit dose form in ampoules, pre-filled syringes, small volume infusion or in multi-dose containers with an added preservative. The therapeutic proteins can be injected by, for example, subcutaneous injections, intramuscular injections, intrathecal injections, intracerebral injections, intraparenchymal injections, intraventricular injections, and intravenous (IV) infusions or injections.

In one embodiment, the recombinant human NaGlu protein is administered intravenously by IV infusion by any useful method. In one example, the recombinant human NaGlu protein can be administered by intravenous infusion through a peripheral line. In another example, the recombinant human NaGlu protein can be administered by intravenous infusion through a peripherally inserted central catheter. In another example, the recombinant human NaGlu protein can be administered by intravenous infusion facilitated by an ambulatory infusion machine attached to a venous vascular access port. In one embodiment of intravenous infusion, the medication is administered over a period of 1 to 8 hours depending on the amount of medication to be infused and the patient's previous infusion-related reaction history, as determined by a physician skilled in the art. In another embodiment, the recombinant human NaGlu protein is administered intravenously by IV injection. In another embodiment, the recombinant human NaGlu protein can be administered via intraperitoneal or intrathecal injection.

In some embodiments, the therapeutic proteins are administered by infusion, and the infusion can occur over an extended time period, for example, 30 minutes to 10 hours. Thus, the infusion can occur, for example, over a period of about 1 hour, about 2 hours, about 3 hours, about 4 hours, or about 5 hours. The infusion can also occur at various rates. Thus, for example, the infusion rate can be about 1 mL per hour to about 20 mL per hour. In some embodiments, the infusion rate is 5 mL to 10 mL per hour. In one embodiment, the infusion rate is 1, 2, 3, 4, 5, 6, 7, 8, 9, 10, 11, 12, 13, 14, 15, 16, 17, 18, 19 or 20 mL per hour. In one embodiment, the infusion rate is 0.1 to 5 mg/kg/hr. In one embodiment, the infusion rate is about 0.1, about 0.2, about 0.3, about 0.5, about 1.0, about 1.5, about 2.0, or about 3 mg/kg/hr. Ranges and values intermediate to the above recited ranges and values are also contemplated to be part of the invention.

The therapeutic proteins can take such forms as suspensions, solutions, or emulsions in oily or aqueous vehicles, and can contain formulatory agents such as suspending, stabilizing and/or dispersing agents. The recombinant human NaGlu proteins can be in powder form, obtained by aseptic isolation of sterile solid or by lyophilization from solution, for constitution with a suitable vehicle, e.g., sterile, pyrogen-free water, before use.

Formulations in accordance with the present invention can be assessed based on product quality analysis, reconstitution time (if lyophilized), quality of reconstitution (if lyophilized), high molecular weight, moisture, and glass transition temperature. Typically, protein quality and product analysis include product degradation rate analysis using methods including, but not limited to, size exclusion HPLC (SE-HPLC), cation exchange-HPLC (CEX-HPLC), X-ray diffraction (XRD), modulated differential scanning calorimetry (mDSC), reversed phase HPLC (RP-HPLC), multi-angle light scattering (MALS), fluorescence, ultraviolet absorption, nephelometry, capillary electrophoresis (CE), SDS-PAGE, and combinations thereof. In some embodiments, evaluation of product in accordance with the present invention may include a step of evaluating appearance (either liquid or cake appearance).

Generally, formulations (lyophilized or aqueous) can be stored for extended periods of time at room temperature. Storage temperature may typically range from 0° C. to 45° C. (e.g., 4° C., 20° C., 25° C. or 45° C.). Formulations may be stored for a period of months to a period of years. Storage time generally will be 24 months, 12 months, 6 months, 4.5 months, 3 months, 2 months or 1 month. Formulations can be stored directly in the container used for administration, eliminating transfer steps. Ranges and values intermediate to the above recited ranges and values are also contemplated to be part of the invention.

Formulations can be stored directly in the lyophilization container (if lyophilized), which may also function as the reconstitution vessel, eliminating transfer steps. Alternatively, lyophilized product formulations may be measured into smaller increments for storage. Storage should generally avoid circumstances that lead to degradation of the proteins, including but not limited to exposure to sunlight, UV radiation, other forms of electromagnetic radiation, excessive heat or cold, rapid thermal shock, and mechanical shock. The pharmaceutical compositions according to the invention can also contain other active ingredients such as immunosuppressive agents, antimicrobial agents, or preservatives, discussed in more detail below.

VII. Methods of Treatment

The present invention also provides methods of treating NaGlu-associated diseases, e.g., Sanfilippo Syndrome B. Recombinant NaGlu employed in accordance with the invention includes recombinant NaGlu which can be produced in any useful protein expression system including, without limitation, cell culture (e.g., CHO cells, COS cells), bacteria such as *E. coli*, transgenic animals such as mammals and avians (e.g., chickens, duck, and turkey) and in plant systems (e.g., duck weed and tobacco plants). In one embodiment, the recombinant NaGlu is produced in a transgenic animal, such as an avian.

In one embodiment, the method comprises administering to the subject a recombinant human NaGlu protein (rhNaGlu), for instance a recombinant human NaGlu protein containing a sufficient amount of oligosaccharides (e.g., mannose and phosphorylated mannose (i.e., M6P)), in an amount sufficient to treat (e.g., reduce, ameliorate) or prevent one or more symptoms of a NaGlu deficiency or NaGlu associated disease. The recombinant human NaGlu protein can be administered therapeutically or prophylactically, or both. The recombinant human NaGlu protein (rhNaGlu) can be administered to the subject, alone or in combination with other therapeutic modalities as described herein.

The terms "treat," "treating," and "treatment" refer to methods of alleviating, abating, or ameliorating a disease or symptom, preventing an additional symptom, ameliorating or preventing an underlying cause of a symptom, inhibiting a disease or condition, arresting the development of a disease or condition, relieving a disease or condition, causing regression of a disease or condition, relieving a condition caused by the disease or condition, or stopping a symptom of the disease or condition either prophylactically and/or after the symptom has occurred.

"Therapeutically effective dose" as used herein refers to the dose (e.g., amount and/or interval) of drug required to produce an intended therapeutic response (e.g., reduction of heparan sulfate levels and/or increase in NaGlu activity in a target tissue). A therapeutically effective dose refers to a dose that, as compared to a corresponding subject who has not received such a dose, results in improved treatment, healing, prevention, or amelioration of a disease, disorder, or side effect, or a decrease in the rate of the occurrence or advancement of a disease or disorder. The term also includes within its scope, doses effective to enhance physiological functions.

As used herein, the term "subject" or "patient" is intended to include human and non-human animals. Non-human animals include all vertebrates, e.g., mammals and non-mammals, such as non-human primates, sheep, dogs, cats, cows, horses, chickens, amphibians, and reptiles. Preferred subjects include human subjects having a NaGlu deficiency or NaGlu associated disease.

As used herein a "NaGlu associated disease" is a disease or condition which is mediated by NaGlu activity or is associated with aberrant NaGlu expression or activity. An example of an NaGlu associated disease includes, but is not limited to, NaGlu deficiency such as Sanfilippo Syndrome B (also known as mucopolysaccharidosis type IIIB).

The therapeutic methods of the present invention encompass any route of administration which facilitates the uptake or transport of the recombinant human NaGlu protein into the pertinent organs and tissues. In one embodiment, the methods of the invention include delivering the recombinant human NaGlu proteins of the invention to the CNS (central nervous system), the kidney, or the liver of a subject for the treatment of a NaGlu associated disease (e.g., NaGlu deficiency). For example, the recombinant human NaGlu protein may be administered to the patient intravenously (e.g., via intravenous injection or intravenous infusion) and surprisingly crosses the blood brain barrier (BBB) of the subject having NaGlu deficiency. In another embodiment of the invention, the recombinant human NaGlu protein is administered to the patient intrathecally.

A. Device for Intrathecal Delivery

Various devices may be used for intrathecal delivery according to the present invention. In some embodiments, a device for intrathecal administration contains a fluid access port (e.g., injectable port); a hollow body (e.g., catheter) having a first flow orifice in fluid communication with the fluid access port and a second flow orifice configured for insertion into spinal cord; and a securing mechanism for securing the insertion of the hollow body in the spinal cord. As a non-limiting example, a suitable securing mechanism contains one or more nobs mounted on the surface of the hollow body and a sutured ring adjustable over the one or more nobs to prevent the hollow body (e.g., catheter) from slipping out of the spinal cord. In various embodiments, the fluid access port comprises a reservoir. In some embodiments, the fluid access port comprises a mechanical pump (e.g., an infusion pump). In some embodiments, an implanted catheter is connected to either a reservoir (e.g., for bolus delivery), or an infusion pump. The fluid access port may be implanted or external.

In some embodiments, intrathecal administration may be performed by either lumbar puncture (i.e., slow bolus) or via a port-catheter delivery system (i.e., infusion or bolus). In some embodiments, the catheter is inserted between the laminae of the lumbar vertebrae and the tip is threaded up the thecal space to the desired level (generally L3-L4).

Relative to intravenous administration, a single dose volume suitable for intrathecal administration is typically small. Typically, intrathecal delivery according to the present invention maintains the balance of the composition of the CSF as well as the intracranial pressure of the subject. In some embodiments, intrathecal delivery is performed absent the corresponding removal of CSF from a subject. In some embodiments, a suitable single dose volume may be e.g., less than about 10 mL, 8 mL, 6 mL, 5 mL, 4 mL, 3 mL, 2 mL, 1.5 mL, 1 mL, or 0.5 mL. In some embodiments, a suitable single dose volume may be about 0.5-5 mL, 0.5-4 mL, 0.5-3 mL, 0.5-2 mL, 0.5-1 mL, 1-3 mL, 1-5 mL, 1.5-3 mL, 1-4 mL, or 0.5-1.5 mL. In some embodiments, intrathecal delivery according to the present invention involves a step of removing a desired amount of CSF first. In some embodiments, less than about 10 mL (e.g., less than about 9 mL, 8 mL, 7 mL, 6 mL, 5 mL, 4 mL, 3 mL, 2 mL, 1 mL) of CSF is first removed before intrathecal administration. In those cases, a suitable single dose volume may be e.g., more than about 3 mL, 4 mL, 5 mL, 6 mL, 7 mL, 8 mL, 9 mL, 10 mL, 15 mL, or 20 mL. Ranges and values intermediate to the above recited ranges and values are also contemplated to be part of the invention.

Various other devices may be used to effect intrathecal administration of a therapeutic composition. For example, formulations containing desired enzymes may be given using an Ommaya reservoir which is in common use for intrathecally administering drugs for meningeal carcinomatosis (Lancet 2: 983-84, 1963). More specifically, in this method, a ventricular tube is inserted through a hole formed in the anterior horn and is connected to an Ommaya reservoir installed under the scalp, and the reservoir is subcutaneously punctured to intrathecally deliver the particular enzyme being replaced, which is injected into the reservoir. Other devices for intrathecal administration of therapeutic compositions or formulations to an individual are described in U.S. Pat. No. 6,217,552, the entire contents of which, as they relate to these devices, are incorporated herein by reference. Alternatively, the drug may be intrathecally given, for example, by a single injection, or continuous infusion. It should be understood that the dosage treatment may be in the form of a single dose administration or multiple doses.

For injection, formulations of the invention can be formulated in liquid solutions. In addition, the NaGlu enzyme may be formulated in solid form and re-dissolved or suspended immediately prior to use. Lyophilized forms are also included. The injection can be, for example, in the form of a bolus injection or continuous infusion (e.g., using infusion pumps) of the NaGlu enzyme.

In one embodiment of the invention, the NaGlu enzyme is administered by lateral cerebro ventricular injection into the brain of a subject. The injection can be made, for example, through a burr hole made in the subject's skull. In another embodiment, the enzyme and/or other pharmaceutical formulation is administered through a surgically inserted shunt into the cerebral ventricle of a subject. For example, the injection can be made into the lateral ventricles, which are larger. In some embodiments, injection into the third and fourth smaller ventricles can also be made.

In yet another embodiment, the pharmaceutical compositions used in the present invention are administered by injection into the cisterna magna, or lumbar area of a subject.

In another embodiment of the method of the invention, the pharmaceutically acceptable formulation provides sustained delivery, e.g., "slow release" of the enzyme or other pharmaceutical composition used in the present invention, to a subject for at least one, two, three, four weeks or longer periods of time after the pharmaceutically acceptable formulation is administered to the subject.

As used herein, the term "sustained delivery" refers to continual delivery of a pharmaceutical formulation of the invention in vivo over a period of time following administration, preferably at least several days, a week or several weeks. Sustained delivery of the composition can be demonstrated by, for example, the continued therapeutic effect of the enzyme over time (e.g., sustained delivery of the enzyme can be demonstrated by continued reduced amount of storage granules in the subject). Alternatively, sustained delivery of the enzyme may be demonstrated by detecting the presence of the enzyme in vivo over time.

B. Intravenous Delivery

As discussed above, one of the surprising features of the present invention is that the recombinant human NaGlu proteins of the invention are able to effectively and extensively diffuse across the blood brain barrier (BBB) and brain surface and penetrate various layers or regions of the brain, including deep brain regions, when administered intravenously. The methods of the present invention effectively deliver the rhNaGlu proteins to various tissues, neurons or cells of the central nervous system (CNS), which are hard to target by existing CNS delivery methods. Furthermore, the methods of the present invention deliver sufficient amounts of the recombinant human NaGlu proteins to the blood stream and various peripheral organs and tissues.

"Intravenous injection," often medically referred to as IV push or bolus injection, refers to a route of administration in which a syringe is connected to the IV access device and the medication is injected directly, typically rapidly and occasionally up to a period of 15 minutes if it might cause irritation of the vein or a too-rapid effect. Once a medicine has been injected into the fluid stream of the IV tubing, there must be some means of ensuring that it gets from the tubing to the patient. Usually this is accomplished by allowing the fluid stream to flow normally and thereby carry the medicine into the bloodstream. However, in some cases a second fluid injection, sometimes called a "flush," is used following the first injection to facilitate the entering of the medicine into the bloodstream.

"Intravenous infusion" refers to a route of administration in which medication is delivered over an extended period of time. For example, the medication can be delivered to a patient over a period of time between 1 and 8 hours. The medication can also be delivered to a patient over a period of about 1, about 2, about 3, about 4, about 5, about 6, about 7, or about 8 hours. To accomplish an intravenous infusion, an IV gravity drip or an IV pump can be used. IV infusion is typically used when a patient requires medications only at certain times and does not require additional intravenous fluids (e.g., water solutions which can contain sodium, chloride, glucose, or any combination thereof) such as those that restore electrolytes, blood sugar, and water loss.

C. Target Tissues

In some embodiments, the rhNaGlu of the invention is delivered to the central nervous system (CNS) of a subject. In some embodiments, the rhNaGlu of the invention is delivered to one or more of target tissues of brain, spinal cord, and/or peripheral organs. As used herein, the term "target tissue" refers to any tissue that is affected by the NaGlu associated disease to be treated or any tissue in which the deficient NaGlu is normally expressed. In some embodiments, target tissues include those tissues in which there is a detectable or abnormally high amount of enzyme substrate, for example stored in the cellular lysosomes of the tissue, in patients suffering from or susceptible to the NaGlu associated disease. In some embodiments, target tissues include those tissues that display a disease-associated pathology, symptom, or feature. In some embodiments, target tissues include those tissues in which the deficient NaGlu is normally expressed at an elevated level. As used herein, a target tissue may be a brain target tissue, a spinal cord target tissue and/or a peripheral target tissue. Exemplary target tissues are described in detail below.

D. Brain Target Tissues

In general, the brain can be divided into different regions, layers and tissues. For example, meningeal tissue is a system of membranes which envelops the central nervous system, including the brain. The meninges contain three layers, including dura matter, arachnoid matter, and pia matter. In general, the primary function of the meninges and of the cerebrospinal fluid is to protect the central nervous system. In some embodiments, a therapeutic protein in accordance with the present invention is delivered to one or more layers of the meninges.

The brain has three primary subdivisions, including the cerebrum, cerebellum, and brain stem. The cerebral hemispheres, which are situated above most other brain structures and are covered with a cortical layer. Underneath the cerebrum lies the brainstem, which resembles a stalk on which the cerebrum is attached. At the rear of the brain, beneath the cerebrum and behind the brainstem, is the cerebellum.

The diencephalon, which is located near the midline of the brain and above the mesencephalon, contains the thalamus, metathalamus, hypothalamus, epithalamus, prethalamus, and pretectum. The mesencephalon, also called the midbrain, contains the tectum, tegumentum, ventricular mesocoelia, and cerebral peduncels, the red nucleus, and the cranial nerve III nucleus. The mesencephalon is associated with vision, hearing, motor control, sleep/wake, alertness, and temperature regulation.

Regions of tissues of the central nervous system, including the brain, can be characterized based on the depth of the tissues. For example, CNS (e.g., brain) tissues can be characterized as surface or shallow tissues, mid-depth tissues, and/or deep tissues.

According to the present invention, the rhNaGlu of the invention may be delivered to any appropriate brain target tissue(s) associated with a particular disease to be treated in a subject. In some embodiments, the rhNaGlu of the invention is delivered to surface or shallow brain target tissue. In some embodiments, the rhNaGlu of the invention is delivered to mid-depth brain target tissue. In some embodiments, the rhNaGlu of the invention is delivered to deep brain target tissue. In some embodiments, the rhNaGlu of the invention is delivered to a combination of surface or shallow brain target tissue, mid-depth brain target tissue, and/or deep brain target tissue. In some embodiments, the rhNaGlu of the invention is delivered to a deep brain tissue at least 4 mm, 5 mm, 6 mm, 7 mm, 8 mm, 9 mm, 10 mm or more below (or internal to) the external surface of the brain. Ranges and values intermediate to the above recited ranges and values are also contemplated to be part of the invention.

In some embodiments, the rhNaGlu of the invention is delivered to one or more surface or shallow tissues of cerebrum. In some embodiments, the targeted surface or shallow tissues of the cerebrum are located within 4 mm from the surface of the cerebrum. In some embodiments, the targeted surface or shallow tissues of the cerebrum are selected from pia mater tissues, cerebral cortical ribbon tissues, hippocampus, Virchow Robin space, blood vessels within the VR space, the hippocampus, portions of the hypothalamus on the inferior surface of the brain, the optic nerves and tracts, the olfactory bulb and projections, and combinations thereof.

In some embodiments, the rhNaGlu of the invention is delivered to one or more deep tissues of the cerebrum. In some embodiments, the targeted surface or shallow tissues of the cerebrum are located at least 4 mm (e.g., 5 mm, 6 mm, 7 mm, 8 mm, 9 mm, or 10 mm) below (or internal to) the surface of the cerebrum. In some embodiments, targeted deep tissues of the cerebrum include the cerebral cortical ribbon. In some embodiments, targeted deep tissues of the cerebrum include one or more of the diencephalon (e.g., the hypothalamus, thalamus, prethalamus or subthalamus), metencephalon, lentiform nuclei, the basal ganglia, caudate, putamen, amygdala, globus pallidus, and combinations thereof.

In some embodiments, the rhNaGlu of the invention is delivered to one or more tissues of the cerebellum. In certain embodiments, the targeted one or more tissues of the cerebellum are selected from the group consisting of tissues of the molecular layer, tissues of the Purkinje cell layer, tissues of the Granular cell layer, cerebellar peduncles, and combination thereof. In some embodiments, therapeutic agents (e.g., enzymes) are delivered to one or more deep tissues of the cerebellum including, but not limited to, tissues of the Purkinje cell layer, tissues of the Granular cell layer, deep cerebellar white matter tissue (e.g., deep relative to the Granular cell layer), and deep cerebellar nuclei tissue.

In some embodiments, the rhNaGlu of the invention is delivered to one or more tissues of the brainstem. In some embodiments, the targeted one or more tissues of the brainstem include brain stem white matter tissue and/or brain stem nuclei tissue.

In some embodiments, the rhNaGlu of the invention is delivered to various brain tissues including, but not limited to, gray matter, white matter, periventricular areas, pia-arachnoid, meninges, neocortex, cerebellum, deep tissues in cerebral cortex, molecular layer, caudate/putamen region, midbrain, deep regions of the pons or medulla, and combinations thereof.

In some embodiments, the rhNaGlu of the invention is delivered to various cells in the brain including, but not limited to, neurons, glial cells, perivascular cells and/or meningeal cells. In some embodiments, a therapeutic protein is delivered to oligodendrocytes of deep white matter.

E. Spinal Cord Target Tissue In general, regions or tissues of the spinal cord can be characterized based on the depth of the tissues. For example, spinal cord tissues can be characterized as surface or shallow tissues, mid-depth tissues, and/or deep tissues.

In some embodiments, the rhNaGlu of the invention are delivered to one or more surface or shallow tissues of the spinal cord. In some embodiments, a targeted surface or shallow tissue of the spinal cord is located within 4 mm from the surface of the spinal cord. In some embodiments, a targeted surface or shallow tissue of the spinal cord contains pia matter and/or the tracts of white matter.

In some embodiments, the rhNaGlu of the invention are delivered to one or more deep tissues of the spinal cord. In some embodiments, a targeted deep tissue of the spinal cord is located internal to 4 mm from the surface of the spinal cord. In some embodiments, a targeted deep tissue of the spinal cord contains spinal cord grey matter and/or ependymal cells.

In some embodiments, replacement enzymes (e.g., a NaGlu fusion protein) are delivered to neurons of the spinal cord.

F. Peripheral Target Tissues

As used herein, peripheral organs or tissues refer to any organs or tissues that are not part of the central nervous system (CNS). Peripheral target tissues may include, but are not limited to, blood system, liver, kidney, heart, endothelium, bone marrow and bone marrow derived cells, spleen, lung, lymph node, bone, cartilage, ovary and testis. In some embodiments, the rhNaGlu of the invention is delivered to one or more of the peripheral target tissues.

G. Biodistribution and Bioavailability

In various embodiments, once delivered to the target tissue, the rhNaGlu of the invention is localized intracellularly. For example, the rhNaGlu of the invention may be localized to exons, axons, lysosomes, mitochondria or vacuoles of a target cell (e.g., neurons such as Purkinje cells). For example, in some embodiments the rhNaGlu of the invention demonstrates translocation dynamics such that the rhNaGlu moves within the perivascular space (e.g., by pulsation-assisted convective mechanisms). In addition, active axonal transport mechanisms relating to the association of the administered protein or enzyme with neurofilaments may also contribute to or otherwise facilitate the distribution of the rhNaGlu proteins of the invention into the deeper tissues of the central nervous system.

In some embodiments, the rhNaGlu of the invention delivered according to the present invention may achieve therapeutically or clinically effective levels or activities in various targets tissues described herein. As used herein, a therapeutically or clinically effective level or activity is a level or activity sufficient to confer a therapeutic effect in a target tissue. The therapeutic effect may be objective (i.e., measurable by some test or marker) or subjective (i.e., subject gives an indication of or feels an effect). For example, a therapeutically or clinically effective level or activity may be an enzymatic level or activity that is sufficient to ameliorate symptoms associated with the disease in the target tissue (e.g., GAG storage).

In some embodiments, the rhNaGlu of the invention delivered according to the present invention may achieve an enzymatic level or activity that is at least 5%, 10%, 20%, 30%, 40%, 50%, 60%, 70%, 80%, 90%, 91%, 92%, 93%, 94%, 95%, 96%, 97%, 98% or 99% of the normal level or activity of the corresponding NaGlu enzyme in the target tissue. In some embodiments, the rhNaGlu of the invention delivered according to the present invention may achieve an enzymatic level or activity that is increased by at least 1-fold, 2-fold, 3-fold, 4-fold, 5-fold, 6-fold, 7-fold, 8-fold, 9-fold or 10-fold as compared to a control (e.g., endogenous levels or activities without the treatment). In some embodiments, the rhNaGlu delivered according to the present invention may achieve an increased enzymatic level or activity at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg or 600 nmol/hr/mg in a target tissue. Ranges and values intermediate to the above recited ranges and values are also contemplated to be part of the invention.

In some embodiments, inventive methods according to the present invention are particularly useful for targeting the lumbar region. In some embodiments, the rhNaGlu delivered according to the present invention may achieve an increased enzymatic level or activity in the lumbar region of at least approximately 500 nmol/hr/mg, 600 nmol/hr/mg, 700 nmol/hr/mg, 800 nmol/hr/mg, 900 nmol/hr/mg, 1000 nmol/hr/mg, 1500 nmol/hr/mg, 2000 nmol/hr/mg, 3000 nmol/hr/mg, 4000 nmol/hr/mg, 5000 nmol/hr/mg, 6000 nmol/hr/mg, 7000 nmol/hr/mg, 8000 nmol/hr/mg, 9000 nmol/hr/mg, or 10,000 nmol/hr/mg. Ranges and values intermediate to the above recited ranges and values are also contemplated to be part of the invention.

In general, therapeutic agents (e.g., the rhNaGlu) delivered according to the present invention have sufficiently long half time in CSF and target tissues of the brain, spinal cord, and peripheral organs. In some embodiments, the rhNaGlu delivered according to the present invention may have a half-life of at least approximately 30 minutes, 45 minutes, 60 minutes, 90 minutes, 2 hours, 3 hours, 4 hours, 5 hours, 6 hours, 7 hours, 8 hours, 9 hours, 10 hours, 12 hours, 16 hours, 18 hours, 20 hours, 25 hours, 30 hours, 35 hours, 40 hours, up to 3 days, up to 7 days, up to 14 days, up to 21 days or up to a month. In some embodiments, In some embodiments, the rhNaGlu delivered according to the present invention may retain detectable level or activity in CSF or bloodstream after 12 hours, 24 hours, 30 hours, 36 hours, 42 hours, 48 hours, 54 hours, 60 hours, 66 hours, 72 hours, 78 hours, 84 hours, 90 hours, 96 hours, 102 hours, or a week following administration. Detectable level or activity may be determined using various methods known in the art. Ranges and values intermediate to the above recited ranges and values are also contemplated to be part of the invention.

In certain embodiments, the rhNaGlu delivered according to the present invention achieves a concentration of at least 30 µg/mL in the CNS tissues and cells of the subject following administration (e.g., one week, 3 days, 48 hours, 36 hours, 24 hours, 18 hours, 12 hours, 8 hours, 6 hours, 4 hours, 3 hours, 2 hours, 1 hour, 30 minutes, or less, following administration of the pharmaceutical composition to the subject). In certain embodiments, the rhNaGlu delivered according to the present invention achieves a concentration of at least 2 µg/mL, at least 15 µg/mL, at least 1 µg/mL, at least 7 µg/mL, at least 5 µg/mL, at least 2 µg/mL, at least 1 µg/mL or at least 0.5 µg/mL in the targeted tissues or cells of the subject (e.g., brain tissues or neurons) following administration to such subject (e.g., one week, 3 days, 48 hours, 36 hours, 24 hours, 18 hours, 12 hours, 8 hours, 6 hours, 4 hours, 3 hours, 2 hours, 1 hour, 30 minutes, or less following administration of such pharmaceutical compositions to the subject). Ranges and values intermediate to the above recited ranges and values are also contemplated to be part of the invention.

H. Treatment of Sanfilippo Syndrome

Sanfilippo syndrome, or mucopolysaccharidosis III (MPS III), is a rare genetic disorder characterized by the deficiency of enzymes involved in the degradation of glycosaminoglycans (GAG). In the absence of enzyme, partially degraded GAG molecules cannot be cleared from the body and accumulate in lysosomes of various tissues, resulting in progressive widespread somatic dysfunction (Neufeld and Muenzer, 2001).

Four distinct forms of MPS III, designated MPS IIIA, B, C, and D, have been identified. Each represents a deficiency in one of four enzymes involved in the degradation of the GAG heparan sulfate. All forms include varying degrees of the same clinical symptoms, including coarse facial features, hepatosplenomegaly, corneal clouding and skeletal deformities. Most notably, however, is the severe and progressive loss of cognitive ability, which is tied not only to the accumulation of heparan sulfate in neurons, but also the subsequent elevation of the gangliosides GM2, GM3 and GD2 caused by primary GAG accumulation (Walkley 1998).

Mucopolysaccharidosis type IIIB (MPS IIIB; Sanfilippo syndrome B) is an autosomal recessive disorder that is characterized by a deficiency of the enzyme alpha-N-acetyl-glucosaminidase (NaGlu). In the absence of this enzyme, GAG heparan sulfate accumulates in lysosomes of neurons and glial cells, with lesser accumulation outside the brain.

A defining clinical feature of this disorder is central nervous system (CNS) degeneration, which results in loss of, or failure to attain, major developmental milestones. The progressive cognitive decline culminates in dementia and premature mortality. The disease typically manifests itself in young children, and the lifespan of an affected individual generally does not extend beyond late teens to early twenties.

Compositions and methods of the present invention may be used to effectively treat individuals suffering from or susceptible to Sanfilippo syndrome B. The terms, "treat" or "treatment," as used herein, refers to amelioration of one or more symptoms associated with the disease, prevention or delay of the onset of one or more symptoms of the disease, and/or lessening of the severity or frequency of one or more symptoms of the disease.

In some embodiments, treatment refers to partial or complete alleviation, amelioration, relief, inhibition, delaying onset, reducing severity and/or incidence of neurological impairment in a Sanfilippo syndrome B patient. As used herein, the term "neurological impairment" includes various symptoms associated with impairment of the central nervous system (e.g., the brain and spinal cord). Symptoms of neurological impairment may include, for example, developmental delay, progressive cognitive impairment, hearing loss, impaired speech development, deficits in motor skills, hyperactivity, aggressiveness and/or sleep disturbances, among others.

Thus, in some embodiments, treatment refers to decreased lysosomal storage (e.g., of GAG) in various tissues. In some embodiments, treatment refers to decreased lysosomal storage in brain target tissues, spinal cord neurons, and/or peripheral target tissues. In certain embodiments, lysosomal storage is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, lysosomal storage is decreased by at least 1-fold, 2-fold, 3-fold, 4-fold, 5-fold, 6-fold, 7-fold, 8-fold, 9-fold or 10-fold as compared to a control. In some embodiments, lysosomal storage is determined by LAMP-1 staining. Ranges and values intermediate to the above recited ranges and values are also contemplated to be part of the invention.

In some embodiments, treatment refers to reduced vacuolization in neurons (e.g., neurons containing Purkinje cells). In certain embodiments, vacuolization in neurons is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, vacuolization is decreased by at least 1-fold, 2-fold, 3-fold, 4-fold, 5-fold, 6-fold, 7-fold, 8-fold, 9-fold or 10-fold as compared to a control. Ranges and values intermediate to the above recited ranges and values are also contemplated to be part of the invention.

In some embodiments, treatment refers to increased NaGlu enzyme activity in various tissues. In some embodiments, treatment refers to increased NaGlu enzyme activity in brain target tissues, spinal cord neurons and/or peripheral target tissues. In some embodiments, NaGlu enzyme activity is increased by about 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900% 1000% or more as compared to a control. In some embodiments, NaGlu enzyme activity is increased by at least 1-fold, 2-fold, 3-fold, 4-fold, 5-fold, 6-fold, 7-fold, 8-fold, 9-fold or 10-fold as compared to a control. In some embodiments, increased NaGlu enzymatic activity is at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg, 600 nmol/hr/mg or more. In some embodiments, NaGlu enzymatic activity is increased in the lumbar region. In some embodiments, increased NaGlu enzymatic activity in the lumbar region is at least approximately 2000 nmol/hr/mg, 3000 nmol/hr/mg, 4000 nmol/hr/mg, 5000 nmol/hr/mg, 6000 nmol/hr/mg, 7000 nmol/hr/mg, 8000 nmol/hr/mg, 9000 nmol/hr/mg, 10,000 nmol/hr/mg, or more. Ranges and values intermediate to the above recited ranges and values are also contemplated to be part of the invention.

In certain embodiments, treatment according to the present invention results in a reduction (e.g., about a 5%, 10%, 15%, 20%, 25%, 30%, 40%, 50%, 55%, 60%, 65%, 70%, 75%, 80%, 90%, 95%, 97.5%, 99% or more reduction) or a complete elimination of the presence, or alternatively the accumulation, of one or more pathological or biological markers which are associated with the NaGlu associated disease. Such reduction or elimination may be particularly evident in the cells and tissues of the CNS (e.g., neurons and oligodendrocytes). For example, in some embodiments, upon administration to a subject the pharmaceutical compositions of the present invention demonstrate or achieve a reduction in the accumulation of the biomarker lysosomal associated membrane protein 1 (LAMP1) in the CNS cells and tissues of the subject (e.g., in the cerebral cortex, cerebellum, caudate nucleus and putamen, white matter and/or thalamus). LAMP1 is a glycoprotein highly expressed in lysosomal membranes and its presence is elevated many patients with a lysosomal storage disorder (Meikle et al., Clin. Chem. (1997) 43:1325-1335). The presence or absence of LAMP1 in patients (e.g., as determined by LAMP staining) with a lysosomal storage disease therefore may provide a useful indicator of lysosomal activity and a marker for both the diagnosis and monitoring of lysosomal storage diseases.

Accordingly, some embodiments of the present invention relate to methods of reducing or otherwise eliminating the presence or accumulation of one or more pathological or biological markers associated with the NaGlu associated disease. Similarly, some embodiments of the invention relate to methods of increasing the degradation (or the rate of degradation) of one or more pathological or biological markers (e.g., LAMP1) associated with lysosomal storage diseases.

In some embodiments, treatment refers to decreased progression of loss of cognitive ability. In certain embodiments, progression of loss of cognitive ability is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, treatment refers to decreased developmental delay. In certain embodiments, developmental delay is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. Ranges and values intermediate to the above recited ranges and values are also contemplated to be part of the invention.

In some embodiments, treatment refers to increased survival (e.g., survival time). For example, treatment can result in an increased life expectancy of a patient. In some embodiments, treatment according to the present invention results in an increased life expectancy of a patient by more than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200% or more, as compared to the average life expectancy of one or more control individuals with similar disease without treatment. In some embodiments, treatment according to the present invention results in an increased life expectancy of a patient by more than about 6 month, about 7 months, about 8 months, about 9 months, about 10 months, about 11 months, about 12 months, about 2 years, about 3 years, about 4 years, about 5 years, about 6 years, about 7 years, about 8 years, about 9 years, about 10 years or more, as compared to the average life expectancy of one or more control individuals with similar disease without treatment. In some embodiments, treatment according to the present invention results in long term survival of a patient. As used herein, the term "long term survival" refers to a survival time or life expectancy longer than about 40 years, 45 years, 50 years, 55 years, 60 years, or longer. Ranges and values intermediate to the above recited ranges and values are also contemplated to be part of the invention.

The terms, "improve," "increase" or "reduce," as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with Sanfilippo syndrome B, who is about the same age and/or gender as the individual being treated (to ensure that the stages of the disease in the treated individual and the control individual(s) are comparable).

The individual (also referred to as "patient" or "subject") being treated is an individual (fetus, infant, child, adolescent, or adult human) having Sanfilippo syndrome B or having the potential to develop Sanfilippo syndrome B. The individual can have residual endogenous NaGlu expression and/or activity, or no measurable activity. For example, the individual having Sanfilippo Syndrome B may have NaGlu expression levels that are less than about 30-50%, less than about 25-30%, less than about 20-25%, less than about 15-20%, less than about 10-15%, less than about 5-10%, less than about 0.1-5% of normal NaGlu expression levels. Ranges and values intermediate to the above recited ranges and values are also contemplated to be part of the invention.

In some embodiments, the individual is an individual who has been recently diagnosed with the disease. Typically, early treatment (treatment commencing as soon as possible after diagnosis) is important to minimize the effects of the disease and to maximize the benefits of treatment.

I. Combination Therapies

Recombinant human NaGlu proteins, for instance a recombinant human NaGlu protein containing a sufficient amount of oligosaccharides (e.g., mannose and phosphorylated mannose (i.e., M6P)), can be used alone or in combination to treat NaGlu associated diseases (e.g., Sanfilippo Syndrome B). It should be understood that the recombinant human NaGlu proteins of the invention can be used alone or in combination with an additional procedure, e.g., surgical procedure, or agent, e.g., therapeutic agent, the additional procedure or agent being selected by the skilled artisan for its intended purpose. For instance, the additional procedure or agent can be a therapeutic procedure or agent art-recognized as being useful to treat the disease or condition being treated by the recombinant human NaGlu protein of the present invention. The additional procedure or agent also can be an agent that imparts a beneficial attribute to the therapeutic composition, e.g., an agent which affects the viscosity of the composition.

It should also be understood that the combinations which are included within this invention are those combinations useful for their intended purpose. The agents and procedures set forth below are for illustrative purposes and not intended to be limiting to the present invention. The combinations, which are part of this invention, can be the recombinant human NaGlu proteins of the present invention and at least one additional agent or procedure selected from the lists below. The combination can also include more than one additional agent or procedure, e.g., two or three additional agents if the combination is such that the formed composition can perform its intended function.

The combination therapy can include surgical procedures, gene therapy, or enzyme-replacement therapy. Additionally, the recombinant human NaGlu protein can be coformulated with one or more additional therapeutic agents, e.g., other recombinant proteins or antibodies or drugs capable of preventing or reducing the accumulation of undegraded substrates (e.g., substrate reduction therapy).

In one or more embodiments, the combination therapy can include co-administration with immunosuppresants, as discussed in further detail below. Immunosuppresants such as, but not limited to, antihistamines, corticosteroids, sirolimus, voclosporin, ciclosporin, methotrexate, IL-2 receptor directed antibodies, T-cell receptor directed antibodies, TNF-alpha directed antibodies or fusion proteins (e.g., infliximab, etanercept, or adalimumab), CTLA-4-Ig (e.g., abatacept), anti-OX-40 antibodies can also be administered before, during, or after administration of a recombinant human protein, such as a recombinant human NaGlu protein, for example, if an anaphylactic reaction or adverse immune response is expected or experienced by a patient.

J. Immunogenicity

The pharmaceutical compositions of the present invention are characterized by their tolerability. As used herein, the terms "tolerable" and "tolerability" refer to the ability of the pharmaceutical compositions of the present invention to not elicit an adverse reaction in the subject to whom such composition is administered, or alternatively not to elicit a serious adverse reaction in the subject to whom such composition is administered. In some embodiments, the pharmaceutical compositions of the present invention are well tolerated by the subject to whom such compositions is administered.

Generally, administration of a rhNaGlu protein according to the present invention does not result in severe adverse effects in the subject. As used herein, severe adverse effects induce, but are not limited to, substantial immune response, toxicity, or death. As used herein, the term "substantial immune response" refers to severe or serious immune responses, such as adaptive T-cell immune responses.

Thus, in many embodiments, inventive methods according to the present invention do not involve concurrent immunosuppressant therapy (i.e., any immunosuppressant therapy used as pre-treatment/pre-conditioning or in parallel to the method). In some embodiments, inventive methods according to the present invention do not involve an immune tolerance induction in the subject being treated. In some embodiments, inventive methods according to the present invention do not involve a pre-treatment or preconditioning of the subject using T-cell immunosuppressive agent.

However, in some embodiments, a subject mounts an immune response after being administered the rhNaGlu of the invention. Thus, in some embodiments, it may be useful to render the subject receiving the rhNaGlu of the invention tolerant to the enzyme replacement therapy. Immune tolerance may be induced using various methods known in the art. For example, an initial 30-60 day regimen of a T-cell immunosuppressive agent such as cyclosporin A (CsA) and an antiproliferative agent, such as, azathioprine (Aza), combined with weekly intrathecal infusions of low doses of a desired replacement enzyme may be used.

Any immunosuppressant agent known to the skilled artisan may be employed together with a combination therapy of the invention. Such immunosuppressant agents include but are not limited to cyclosporine, FK506, rapamycin, CTLA4-Ig, and anti-TNF agents such as etanercept (see e.g., Moder, 2000, Ann. Allergy Asthma Immunol. 84, 280-284; Nevins, 2000, Curr Opin. Pediatr. 12, 146-150; Kurlberg et al., 2000, Scand. J. Immunol. 51, 224-230; Ideguchi et al., 2000, Neuroscience 95, 217-226; Potter et al., 1999, Ann. N.Y. Acad. Sci. 875, 159-174; Slavik et al., 1999, Immunol. Res. 19, 1-24; Gaziev et al., 1999, Bone Marrow Transplant. 25, 689-696; Henry, 1999, Clin. Transplant. 13, 209-220; Gummert et al., 1999, J. Am. Soc. Nephrol. 10, 1366-1380; Qi et al., 2000, Transplantation 69, 1275-1283). The anti-IL2 receptor (α-subunit) antibody daclizumab (e.g., Zenapax™), which has been demonstrated effective in transplant patients, can also be used as an immunosuppressant agent (see e.g., Wiseman et al., 1999, Drugs 58, 1029-1042; Beniaminovitz et al., 2000, N. Engl J. Med. 342, 613-619; Ponticelli et al., 1999, Drugs R. D. 1, 55-60; Berard et al., 1999, Pharmacotherapy 19, 1 127-1 137; Eckhoff et al., 2000, Transplantation 69, 1867-1872; Ekberg et al., 2000, Transpl. Int. 13, 151-159). Additional immunosuppressant agents include but are not limited to anti-CD2 (Branco et al., 1999, Transplantation 68, 1588-1596; Przepiorka et al., 1998, Blood 92, 4066-4071), anti-CD4 (Marinova-Mutafchieva et al., 2000, Arthritis Rheum. 43, 638-644; Fishwild et al., 1999, Clin. Immunol. 92, 138-152), and anti-CD40 ligand (Hong et al., 2000, Semin. Nephrol. 20, 108-125; Chirmule et al., 2000, J. Virol. 74, 3345-3352; Ito et al., 2000, J. Immunol. 164, 1230-1235).

In other embodiments, the invention includes methods comprising co-administration of the NaGlu proteins of the present invention with agents which decrease or suppress an immune response to the NaGlu protein, e.g., immunosuppresants. Immunosuppresants such as, but not limited to, antihistamines, corticosteroids, sirolimus, voclosporin, ciclosporin, methotrexate, IL-2 receptor directed antibodies, T-cell receptor directed antibodies, TNF-alpha directed antibodies or fusion proteins (e.g., infliximab, etanercept, or adalimumab), CTLA-4-Ig (e.g., abatacept), anti-OX-40 antibodies can also be administered before, during, or after administration of a recombinant human protein, such as a recombinant human NaGlu protein, for example, if an anaphylactic reaction or adverse immune response is expected or experienced by a patient.

In one embodiment, the invention provides for a pretreatment procedure to minimize or prevent any potential anaphylactic reactions that can be incurred by administration of the recombinant protein in accordance with the invention. In one embodiment, to prevent a potential anaphylactic reaction, an H-1 receptor antagonist, also known as an antihistamine (e.g., diphenhydramine) is administered to the patient. In one embodiment, the H-1 receptor antagonist is administered in a dose of about 1 mg to about 10 mg per kilogram of body weight. For example, an antihistamine can be administered in a dose of about 5 mg per kilogram. In one embodiment, the antihistamine is administered in a dose of between about 0.1 mg and about 10 mg per kilogram of body weight. In one embodiment, the antihistamine is administered in a dose between about 1 mg and about 5 mg per kilogram of body weight. For example the dose can be 1 mg, 2 mg, 3 mg, 4 mg, or 5 mg per kilogram of body weight. The antihistamine can be administered by any useful method. In one embodiment, the antihistamine is administered intravenously. In another embodiment, the antihistamine is administered in pharmaceutically acceptable capsules.

Administration of the antihistamine can be prior to the administration of the recombinant NaGlu in accordance with the invention. In one embodiment, the H-1 receptor antagonist is administered about 10 to about 90 minutes, for example, about 30 to about 60 minutes prior to the administration of recombinant NaGlu. The H-1 receptor antagonist can be administered using an ambulatory system connected to a vascular access port. In one embodiment, the antihistamine is administered about 90 minutes prior to the administration of recombinant NaGlu. In one embodiment, the antihistamine is administered between about 10 and about 60 minutes prior to the administration of recombinant NaGlu. In another embodiment, the antihistamine is administered between about 20 and about 40 minutes prior to administering recombinant NaGlu. For example, the antihistamine can be administered 20, 25, 30, 35, or 40 minutes prior to the administration of recombinant NaGlu.

In one embodiment, the antihistamine administered is diphenhydramine. Any useful antihistamine can be used. Such antihistamines include, without limitation, clemastine, doxylamine, loratidine, desloratidine, fexofenadine, pheniramine, cetirizine, ebastine, promethazine, chlorpheniramine, levocetirizine, olopatadine, quetiapine, meclizine, dimenhydrinate, embramine, dimethidene, and dexchloropheniramine.

In another embodiment, with reference to intravenous infusion, the potential for anaphylactic reactions can be reduced by administering the infusions using a ramp-up protocol. In this context, a ramp-up protocol refers to slowly increasing the rate of the infusion over the course of the infusion in order to desensitize the patient to the infusion of the medication.

K. Administration

The methods of the present invention contemplate single as well as multiple administrations of a therapeutically effective amount of the rhNaGlu of the invention described herein. The rhNaGlu of the invention can be administered at regular intervals, depending on the nature, severity and extent of the subject's condition. In some embodiments, a therapeutically effective amount of the rhNaGlu protein of the present invention may be administered intravenously or intrathecally periodically at regular intervals (e.g., once every year, once every six months, once every five months, once every three months, bimonthly (once every two months), monthly (once every month), biweekly (once every two weeks) or weekly).

In some embodiments, intrathecal administration may be used in conjunction with other routes of administration (e.g., intravenous, subcutaneously, intramuscularly, parenterally, trans dermally, or transmucosally (e.g., orally or nasally)). In some embodiments, those other routes of administration (e.g., intravenous administration) may be performed no more frequent than biweekly, monthly, once every two months, once every three months, once every four months, once every five months, once every six months, annually administration.

As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). For example, a therapeutically effective amount may be an amount sufficient to achieve a desired therapeutic and/or prophylactic effect, such as an amount sufficient to modulate lysosomal enzyme receptors or their activity to thereby treat such lysosomal storage disease or the symptoms thereof (e.g., a reduction in or elimination of the presence or incidence of "zebra bodies" or cellular vacuolization following the administration of the compositions of the present invention to a subject). Generally, the amount of a therapeutic agent (e.g., the rhNaGlu of the invention) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

In some embodiments, the therapeutically effective dose ranges from about 0.005 mg/kg body weight to 500 mg/kg body weight, e.g., from about 0.005 mg/kg body weight to 400 mg/kg body weight, from about 0.005 mg/kg body weight to 300 mg/kg body weight, from about 0.005 mg/kg body weight to 200 mg/kg body weight, from about 0.005 mg/kg body weight to 100 mg/kg body weight, from about 0.005 mg/kg body weight to 90 mg/kg body weight, from about 0.005 mg/kg body weight to 80 mg/kg body weight, from about 0.005 mg/kg body weight to 70 mg/kg body weight, from about 0.005 mg/kg body weight to 60 mg/kg body weight, from about 0.005 mg/kg body weight to 50 mg/kg body weight, from about 0.005 mg/kg body weight to 40 mg/kg body weight, from about 0.005 mg/kg body weight to 30 mg/kg body weight, from about 0.005 mg/kg body weight to 25 mg/kg body weight, from about 0.005 mg/kg body weight to 20 mg/kg body weight, from about 0.005 mg/kg body weight to 15 mg/kg body weight, from about 0.005 mg/kg body weight to 10 mg/kg bra body in weight. Ranges and values intermediate to the above recited ranges and values (e.g., 10-50 mg/kg, 1-5 mg/kg, 2-8 mg/kg, 5-10 mg/kg, 0.1-10 mg/kg, 0.3-30 mg/kg, 0.3-50 mg/kg, 0.5-10 mg/kg, 5-30 mg/kg, or 6-27 mg/kg) are also contemplated to be part of the invention.

In some embodiments, the therapeutically effective dose is greater than or at least about 0.1 mg/kg body weight, greater than or at least about 0.2 mg/kg body weight, greater than or at least about 0.3 mg/kg body weight, greater than or at least about 0.4 mg/kg body weight, greater than or at least about 0.5 mg/kg body weight, greater than or at least about 1.0 mg/kg body weight, greater than or at least about 3 mg/kg body weight, greater than or at least about 5 mg/kg body weight, greater than or at least about 6 mg/kg body weight, greater than or at least about 7 mg/kg body weight greater than or at least about 10 mg/kg body weight, greater than or at least about 15 mg/kg body weight, greater than or at least about 20 mg/kg body weight, greater than or at least about 30 mg/kg body weight, greater than or at least about 40 mg/kg body weight, greater than or at least about 50 mg/kg body weight, greater than or at least about 60 mg/kg body weight, greater than or at least about 70 mg/kg body weight, greater than about or at least 80 mg/kg body weight, greater than or at least about 90 mg/kg body weight, greater than or at least about 100 mg/kg body weight. Ranges and values intermediate to the above recited ranges and values are also contemplated to be part of the invention.

In some embodiments, the therapeutically effective dose may also be defined by mg/kg brain weight. As one skilled in the art would appreciate, the brain weights and body weights can be correlated (see, e.g., Dekaban A S. "Changes in brain weights during the span of human life: relation of brain weights to body heights and body weights," Ann Neurol 1978; 4:345-56).

In some embodiments, the therapeutically effective dose may also be defined by mg/15 cc of CSF. As one skilled in the art would appreciate, therapeutically effective doses based on brain weights and body weights can be converted to mg/15 cc of CSF. For example, the volume of CSF in adult humans is approximately 150 mL (Johanson C E, et al. "Multiplicity of cerebrospinal fluid functions: New challenges in health and disease," Cerebrospinal Fluid Res. 2008 May 14; 5: 10). Therefore, single dose injections of 0.1 mg to 50 mg protein to adults would be approximately 0.01 mg/15 cc of CSF (0.1 mg) to 5.0 mg/15 cc of CSF (50 mg) doses in adults.

It is to be further understood that for any particular subject, specific dosage regimens should be adjusted over time according to the individual need and the professional judgment of the person administering or supervising the administration of the enzyme replacement therapy and that dosage ranges set forth herein are exemplary only and are not intended to limit the scope or practice of the claimed invention.

VIII. Kits

The present invention further provides kits or other articles of manufacture which contain the recombinant human NaGlu of the present invention and provide instructions for its reconstitution (if lyophilized) and/or use. Kits or other articles of manufacture may include a container, a catheter and any other articles, devices or equipment useful in intrathecal administration and associated surgery. Suitable containers include, for example, bottles, vials, syringes (e.g., pre-filled syringes), ampules, cartridges, reservoirs, or lyojects. The container may be formed from a variety of materials such as glass or plastic. In some embodiments, a container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, a label on, or associated with, the container may indicate directions for use and/or reconstitution. For example, the label may indicate that the formulation is reconstituted to protein concentrations as described above. The label may further indicate that the formulation is useful or intended for, for example, intravenous or intrathecal administration. In some embodiments, a container may contain a single dose of a stable formulation containing a replacement enzyme (e.g., a recombinant NaGlu protein). In various embodiments, a single dose of the stable formulation is present in a volume of less than about 15 mL, 10 mL, 5.0 mL, 4.0 mL, 3.5 mL, 3.0 mL, 2.5 mL, 2.0 mL, 1.5 mL, 1.0 mL, or 0.5 mL. Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final protein concentration in the reconstituted formulation will generally be at least 1 mg/mL (e.g., at least 5 mg/mL, at least 10 mg/mL, at least 25 mg/mL, at least 50 mg/mL, at least 75 mg/mL, at least 100 mg/mL).

Kits or other articles of manufacture may further include other materials desirable from a commercial and user standpoint, including other buffers, diluents, filters, needles, catheters, syringes, and package inserts with instructions for use. Ranges and values intermediate to the above recited ranges and values are also contemplated to be part of the invention.

EXAMPLES

The following specific examples are intended to illustrate the invention and should not be construed as limiting the scope of the claims. The contents of all figures and all references, patents and published patent applications cited throughout this application, as well as the Figures, are expressly incorporated herein by reference in their entirety.

Example 1

Purification of rhNaGlu rhNaGlu protein was purified by using methods known in the art. Egg white (EW) containing rhNaGlu was solubilized at pH 6 overnight and clarified through centrifugation and/or depth filtration. The EW was adjusted with 1 M NaOAc buffer (pH 4) to pH 6. For the depth filtration process, T2600 filter (Pall™, 40 um) was used as a $1^{st}$ filtration and then PDF1 (Pall™, K200P, 15 um+EKS, 0.22 um) as a $2^{nd}$ filtration step. The filters are single-use membrane with an optimized capacity 60 L EW/m$^2$ for each filter. The hold volume of membrane is 2 L/m$^2$ for T2600 and 4-5 L/m$^2$ for PDF1. In the process, the hold volume was discarded before the filtered EW collected. The buffer (20 mM Phosphate/137 mM NaCl, pH 6) equivalent to the membrane hold volume was used to chase EW left on the filters.

A phenyl-HIC (hydrophobic interaction chromatography) column was applied as a capture step. Since most of egg white proteins are hydrophilic, 99% of egg white proteins passed through the HIC column into flow through. rhNaGlu has a higher hydrophobicity binding to phenyl-HIC.

Egg white containing rhNaGlu was loaded onto the column with a ratio of 30:1. After completion of loading, the column was washed with the equilibration buffer, 5 mM phosphate buffer, pH 6, and 5 mM Tris buffer, pH 7.2. rhNaGlu was eluted with 30% propylene glycol, pH 7.2. After the completion of loading, the column was washed with equilibration buffer and 5 mM phosphate buffer (pH 6). rhNaGlu was eluted with 30% propylene glycol with 5 mM Tris buffer (pH 7.2). The column binding capacity is approximately 4.5 mg/mL. The purity of rhNaGlu through the phenyl-HIC column can be reached to >95% (950 time increase). The recovery is approximately 80% with 30% of propylene glycol elution.

The eluted rhNaGlu fraction was adjusted to pH 5 with 1 M acetic acid and then loaded onto a GigaCap S column (EW: column size=10:1). The column was equilibrated with 50 mM NaOAc buffer (pH 5). After completion of loading, the column was washed with the equilibration buffer. The rhNaGlu was eluted with 50 mM NaOAc/60 mM NaCl (pH 5).

Figure 6:
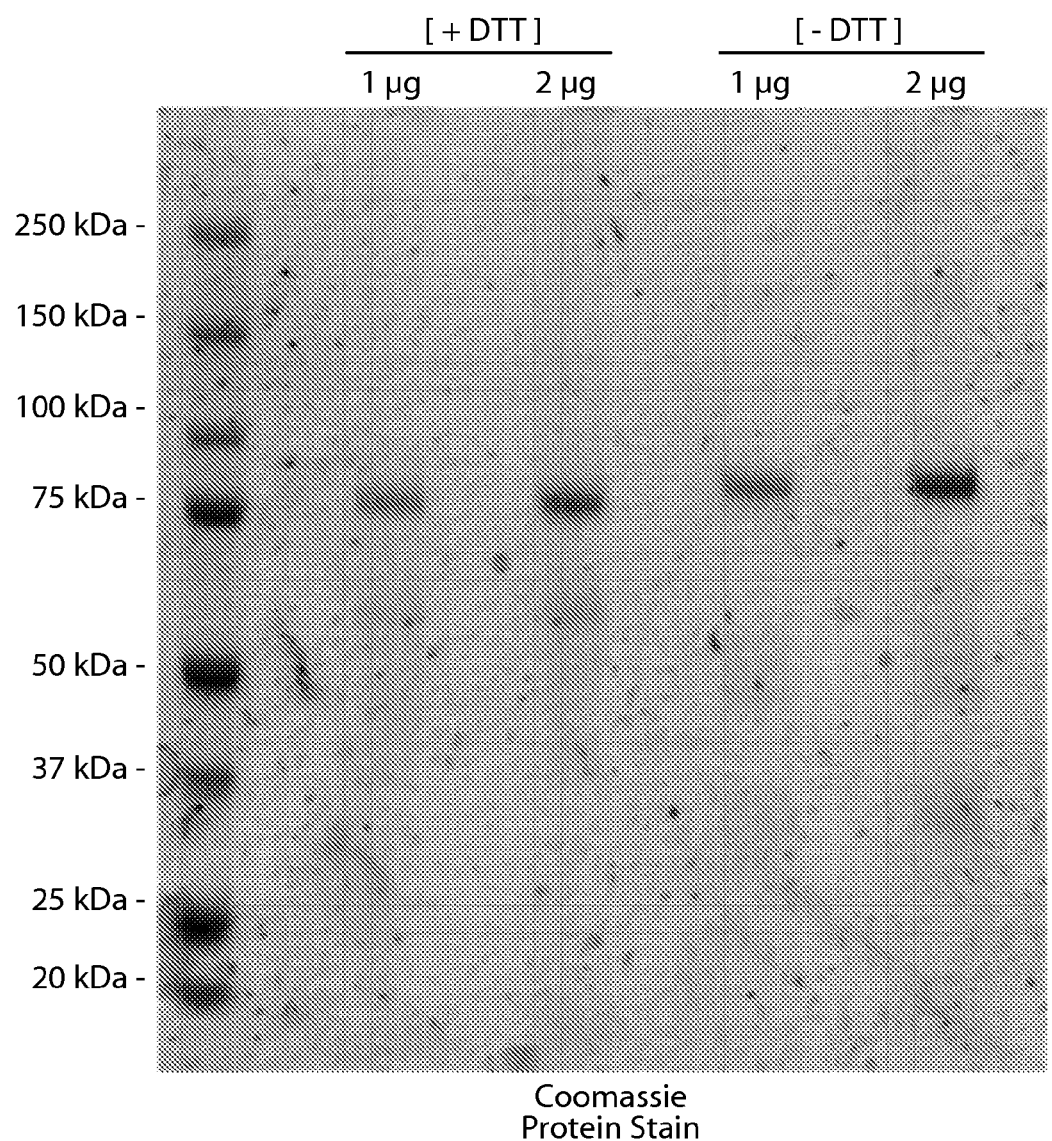
FIG. 6 depicts Western analysis of rhNaGlu isolated and purified from egg white of a transgenic *Gallus*.
Figure 7:
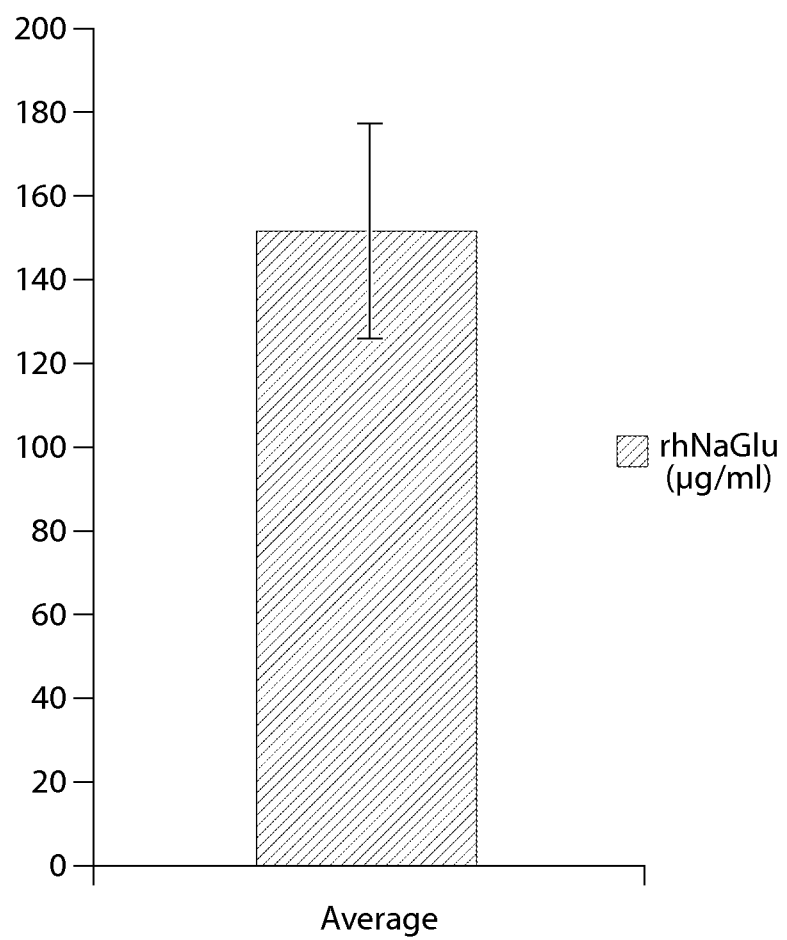
FIG. 7 depicts the average concentration of rhNaGlu deposited in egg white of transgenic *Gallus*.

The protein characterization was performed using purified rhNaGlu. The molecular weight of rhNaGlu (~90 kDa) purified from egg white was analyzed on SDS-PAGE (FIG. 6). The average expression level of rhNaGlu in egg white is shown in FIG. 7. The characteristics of rhNaGlu produced from the transgenic avian are summarized in Table 2.

TABLE 2

|  | rhNaGlu (*Gallus*) |
| --- | --- |
| Apparent Molecular Weight | ~90 kDa |
| pI | 6.1-6.9 |
| pH Stability | pH 5-8 |
| Stability in Egg White | >50 days |

Example 2

Stability of rhNaGlu in Egg White

A single egg was cracked 7 days post-lay and analyzed for activity. Contents were divided in half and each half was subject to standard egg white clarification. Both untreated and clarified egg whites were aliquoted and stored at 4° C. and −20° C. for enzyme activity stability. rhNaGlu in egg white showed stable enzyme activity at least up to 50 days.

Freeze/thaw cycle stability was assessed. The purified rhNaGlu was frozen in liquid nitrogen for 10 seconds and thawed at 37° C. for 2 min. The enzyme activity showed no change for 10 cycles.

The purified rhNaGlu was dialyzed into different pH buffers to measure the stability of pure enzyme. The results showed that pure rhNaGlu was stable between pH 5-8 for 12 days.

Example 3

Oligosaccharide Profiling

Mannose-6-phosphate (M6P) is a terminal monosaccharide of N-linked oligosaccharides that is an important part of the tertiary structure of glycoprotein and, when incorporated in the glycoprotein's final oligosaccharide, is recognized by and bound to the M6P receptors present on the cell surface, subsequently allowing internalization into the lysosomes. Thus, M6P is an effective epitope for the targeting of glycoproteins to the lysosomes.

Analysis of protein glycosylation is an important part of glycoprotein characterization. Oligosaccharides can be linked to a protein through a serine or a threonine as O-lined glycans or through an asparagine as N-linked glycans.

To analyze the structure of oligosaccharides, various chromatographic and spectroscopic techniques were performed. High-performance anion exchange chromatography with pulsed amperometric detection (HPAEC-PAD) was employed. Using this technique, oligosaccharides were quickly separated into general groups based on charge (i.e., neutral, singly charged, or multiply charged) and their structures were determined by comparison to pure standards.

All methods were based on protocols described by Hardy and Townsend (Hardy, M. R., and Townsend, R. R., "High-pH anion-exchange chromatography of glycoprotein-derived carbohydrates", 1994, *Methods Enzymol.* 230: 208-225). Purified samples of transgenic avian derived rhNaGlu were dialyzed using a Tube-O-Dialyzer against nanopure water at 4° C. for about 24 hours to remove salts and other contaminants. Nanopure water was replaced four times during the entire dialysis period. After dialysis, each of the samples was divided into three aliquots. The aliquot intended for neutral and amino sugars analysis was hydrolyzed with 2 N trifluoroacetic acid (TFA) at 100° C. for 4 hours and the aliquot for mannose-6-phosphate analysis was hydrolyzed with 6.75 N TFA at 100° C. for 1.5 hours. The hydrolysates were then dried under $N_2$, re-dissolved with 50 μL $H_2O$, sonicated for 7 min in ice and transferred to an injection vial.

A mix of standards for neutral and amino sugars, and for mannose-6-phosphate with a known number of moles was hydrolyzed in the same manner and at the same time as the sample. Four different concentrations of the neutral and amino sugar standard mix and mannose-6-phosphate were prepared to establish a calibration equation. The number of moles of each sugar in the sample was quantified by linear interpolation from the calibration equation.

The oligossacharide profile and mannose-6-phosphate profile were analyzed separately by HPAEC-PAD. Instrument control and data acquisition were accomplished using Dionex chromeleon software. HPAEC-PAD analysis of hydrolyzed rhNaGlu detected M6P. The mean measured amount of M6P was 3.8 μg (CV 3.7%) per 210 μg of hydrolyzed protein. Converting to moles resulted in 13.4 nmol of M6P per 2.8 nmol of protein which was equivalent to a ratio of 3.2 moles of M6P per mole of protein.

Figure 8:
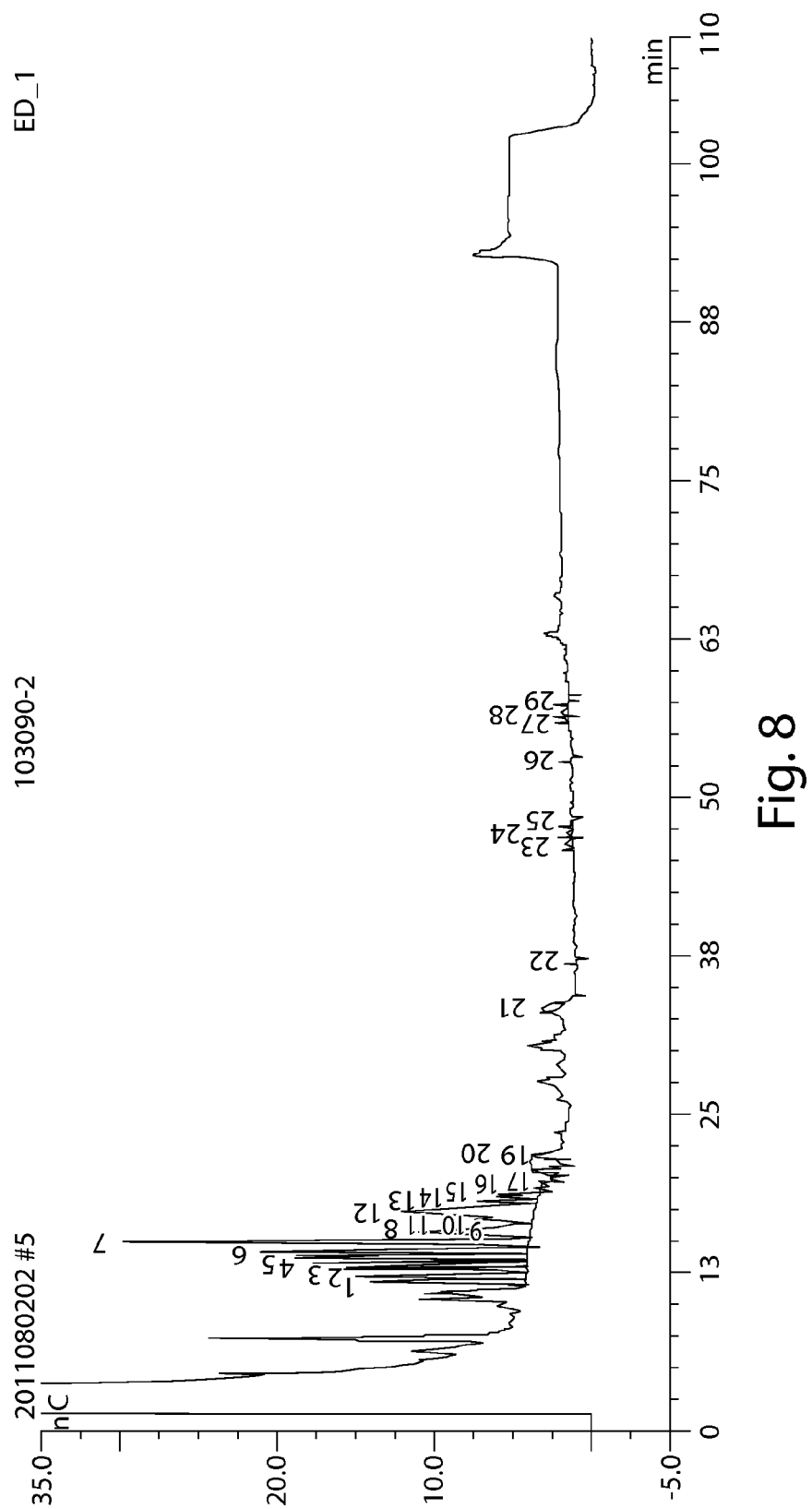
FIG. 8 depicts an oligosaccharide profile of rhNaGlu produced from a transgenic *Gallus* using HPAEC-PAD.

The oligosaccharide profile was also obtained for rhNaGlu (*Gallus*) using HPAEC-PAD (see FIG. 8). The profiles demonstrated good repeatability of the PNGase F reaction on the single sample. Peak clusters were observed in regions corresponding to neutral oligosaccharides (~10 min to ~20 min). A group of significantly smaller peaks eluting between ~25 and ~35 min were also observed, which were possibly attributed to singly charged species.

The monosaccharide composition analysis results obtained from samples of rhNaGlu produced from a transgenic avian (*Gallus*) are summarized in Table 3, which tabulates the average molar ratio of each monosaccharide analyzed for rhNaGlu.

TABLE 3

Monosaccharide Molar Ratios in rhNaGlu (*Gallus*)

| | |
|---|---|
| N-acetylgalactosamine (GalNAc) | 1.1* |
| N-acetylglucosamine (GlcNAc) | 35.6* |
| Galactose (Gal) | 4* |
| Mannose (Man) | 25.5* |
| Mannose-6-phosphate (M6P) | 3.2* |
| Fucose | Not detected |
| Glucose | Not detected |

*mole of monosaccharide per mole of protein

Example 4

Cellular Uptake into Fibroblasts

Wild-type human fibroblasts and mucopolysaccharidosis III B (NaGlu deficient) human fibroblasts were placed in a 24-well plate ($2.5 \times 10^4$ cells per well) and incubated for overnight at 37° C. in 5% $CO_2$. Conditioned media containing fibroblast basal medium and fibroblast growth kit having low serum were used. Various amounts of rhNaGlu (30, 10, 3.0, 1.0, 0.3 and 0 μg/mL) were co-incubated for 24 hours at 37° C. with 5% $CO_2$ to determine levels of cellular uptake by the human fibroblasts (see, FIG. 9). The wells were washed three times with PBS. 100 μL lysis buffer was added per well and the plate was incubated for 10 min at 37° C. Cell lysate was transferred into 1.5 mL centrifuge tube. One cycle of freezing and thawing was performed. The cell lysate was centrifuged at 10,000 rpm for 10 min. 25 μL of supernatants were used for the assay. The assay time was 2 hours. The enzyme activity was measured using the methods known in the art and according to the methods described in Marsh et al., *Clinical Genetics* (1985) 27: 258-262, Chow et al., *Carbohydrate Research* (1981) 96:87-93; Weber et al., *Protein Expression and Purification*, (2001)21:251-259).

Figure 9:
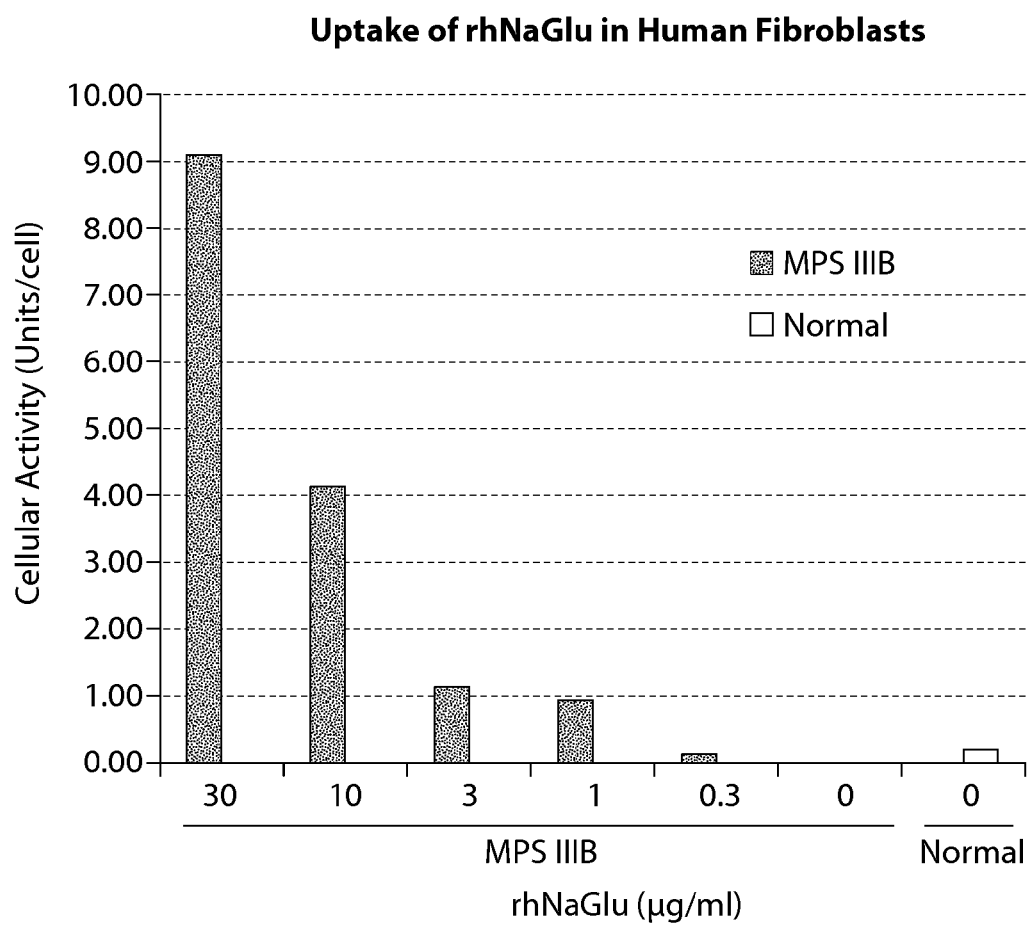
FIG. 9 depicts uptake analysis of rhNaGlu by human skin fibroblasts (MPS IIIB, NaGlu deficient; Normal, wild-type human skin fibroblast; 1U of enzymatic activity=nmol of protein/hr).

As shown in FIG. 9, negative control (i.e., MPS IIIB) did not exhibit any NaGlu activity while positive control (i.e., wild-type human fibroblast) showed NaGlu activity. MPS IIIB cells treated with 0.3 μg/mL of rhNaGlu exhibited approximately 50% of the normal activity level observed in wild-type fibroblast cells. MPS IIIB cells treated with 1 μg/mL of rhNaGlu demonstrated NaGlu activity that was approximately 4-fold higher than that observed in wild-type cells. Surprisingly, MPS IIIB cells treated with 30 μg/mL of rhNaGlu showed NaGlu activity that was at least 40-fold higher than that observed in wild-type cells. This result indicated that rhNaGlu produced from a transgenic avian (*Gallus*) was efficiently internalized into human fibroblasts at a high level.

Figure 10:
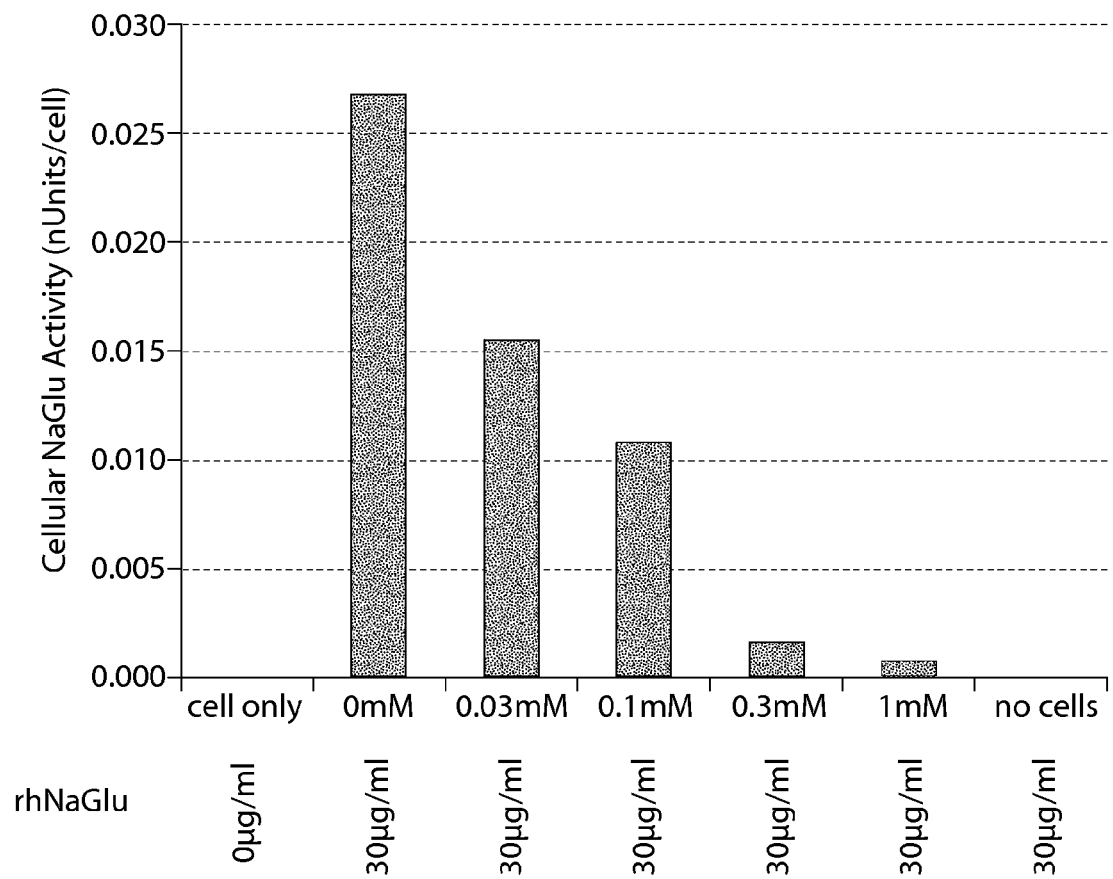
FIG. 10 depicts uptake inhibition analysis of rhNaGlu (*Gallus*) using various concentrations of M6P monosaccharide (1U of enzymatic activity=1 μmol of protein/min).

To determine whether internalization of rhNaGlu is via M6P receptor mediate endocytosis, M6P inhibition assays were performed. For the M6P inhibition assays, various concentrations of free M6P were added to human MPS IIIB fibroblasts treated with 30 μg/mL of rhNaGlu and enzymatic activity was measured as described above. As shown in FIG. 10, human MPS IIIB fibroblasts did not exhibit any NaGlu activity, suggesting effective inhibition of NaGlu uptake by free M6P. In contrast, MPSIII fibroblasts treated with 30 μg/mL of rhNaGlu in the absence of free M6P exhibited a high level of enzymatic activity, suggesting that the protein was efficiently internalized into the NaGlu deficient fibroblasts and retained activity. This enzymatic activity was inhibited by the presence of M6P monosaccharide in the medium at the concentration 0.03 mM and higher. The presence of 1 mM of M6P monosaccharide in conditioned medium inhibited more than 90% of cellular uptake of the protein.

These results indicated that the rhNaGlu produced from a transgenic avian was efficiently internalized into the MPS IIIB fibroblasts via M6P receptor-mediated endocytosis and the rhNaGlu competed with M6P monosaccharides for the receptor recognition. The results were consistent with the glycan analysis that revealed the presence of the M6P structures on the rhNaGlu produced from the transgenic avian.

Example 5

Generation of Active NaGlu Fusion Proteins

Two different rhNaGlu fusion constructs were designed to validate the feasibility of expressing rhNaGlu fusion proteins in the avian expression system.

In one construct, a nucleic acid sequence encoding 8 consecutive aspartic acid residues (DDDDDDDD) was fused to the nucleic sequence encoding NaGlu protein at the 5' end of the full-length NaGlu cDNA sequence (SEQ ID NO:2) using conventional PCR and DNA recombinant technology. In another construct, a nucleic acid sequence encoding TfRL (i.e., THRPPMWSPVWP; SEQ ID NO:5) was fused to the nucleic sequence encoding NaGlu at the 3' end of the full-length NaGlu cDNA sequence. The each construct was inserted into the pTT22 expression vector using EcoRI and HindIII restriction sites. The resulting vectors were each transfected into human embryonic kidney (HEK) 293 cells and stable clones expressing high levels of the fusion NaGlu proteins were obtained. An rhNaGlu protein fused to a stretch of 8 consecutive aspartic acid residues at N-terminus (AAA-NaGlu) and an rhNaGlu protein fused to transferrin receptor ligand (TfRL) at C-terminus (NaGlu-TfRL) were isolated from conditioned media.

The enzymatic activity of AAA-NaGlu and NaGlu-TfRL was measured using the methods known in the art (see, e.g., Marsh et al., *Clinical Genetics* (1985) 27:258-262; Chow et al., *Carbohydrate Research*, (1981) 96:87-93; Weber et al., *Protein Expression and Purification* (2001) 21:251-259; Neufeld et al., *Protein Expression and Purification* (2000) 19:202-211; and Weber et al., *Human Molecular Genetics* (1996) 5:771-777.

Figure 13:
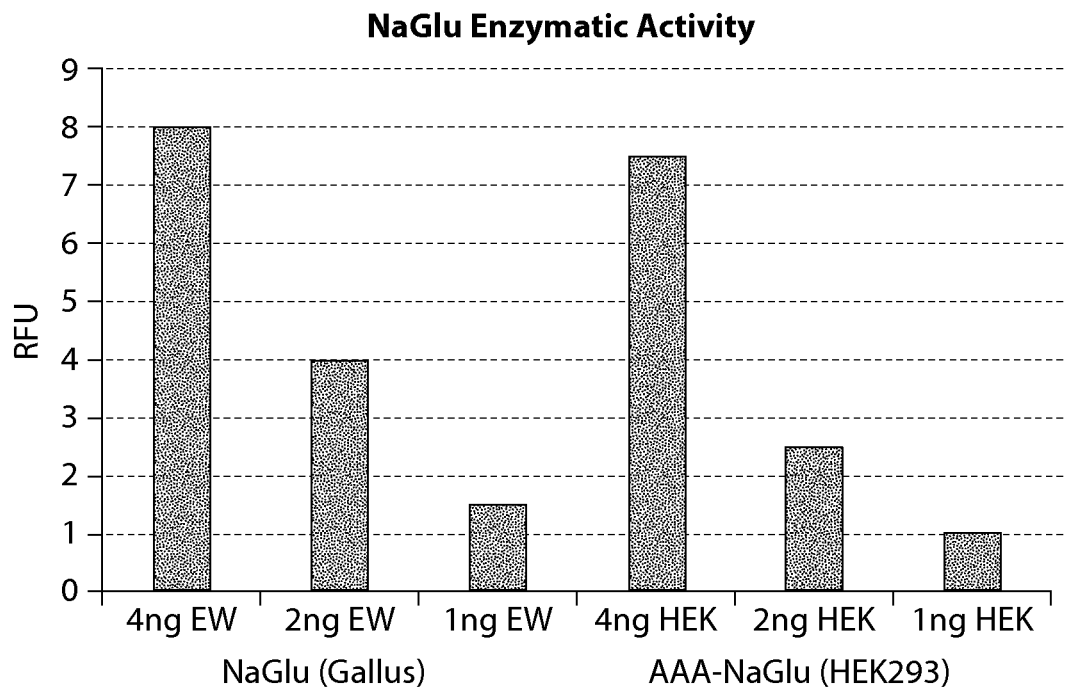
FIG. 13 depicts enzymatic activity of AAA-NaGlu produced from HEK293 as compared to rhNaGlu produced from *Gallus*.
Figure 14:
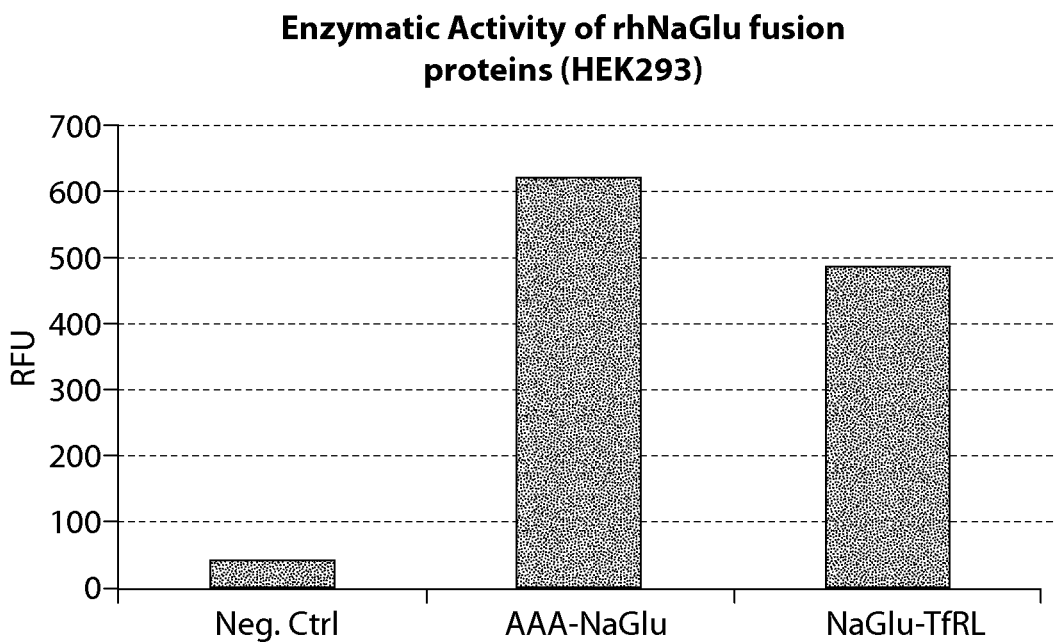
FIG. 14 depicts enzymatic activity of NaGlu-TfRL produced from HEK293 as compared to AAA-NaGlu produced from HEK293.

As shown in FIGS. 13 and 14, AAA-NaGlu and NaGlu-TfRL fusion proteins produced from HEK293 cells showed high levels of enzymatic activity. These results confirmed the possibility that these constructs can be used to produce NaGlu fusion proteins that have increased levels of phosphorylated mannose while retaining enzymatic activity from a transgenic avian expression system.

Example 6

Cellular Uptake into Macrophages

Internalization of rhNaGlu produced from *Gallus* into human macrophage cells was also measured. NR8383 macrophage cells were incubated with 10 μg/mL of rhNaGlu in F12 growth media for 0, 4, 8, 24, 32 and 48 hours at 37° C. with 5% $CO_2$. Samples were recovered and washed with PBS prior to lysis. $2.5 \times 10^5$ cells were lysed in 1 mL of lysis buffer (10 mM of Na Phosphate pH6.0, 0.05% NP40), and lysates transferred into 1.5 mL centrifuge tubes and centrifuged at 10,000 rpm for 10 min. Protein concentration was determined by the Bradford assay and aliquots were frozen for NaGlu enzyme assays.

Enzyme activity was measured using standard methods. 25 mM of substrate (4-methylumbelliferyl 2-Acetamido-2-deoxy-a-D-glucopyranoside) was diluted to 2 mM in nanopure water to form a working substrate stock. Dilutions of samples were prepared in assay buffer (1% bovine serum albumin). 25 μL of 200 mM sodium acetate was distributed to wells of a multi-well plate. 25 μL of standard and 25 μL of samples were added to designated wells. 50 μL of the working substrate stock was added to each well and the plate was gently tapped to mix. The plate was sealed with adhesive film and incubated at 37° C. for 30 minutes. The reaction was then terminated by addition of 50 μL of stop solution (1M Glycine pH 12.5). The plate was placed on a microplate reader using a fluorescence bottom and the intensity was measured at an excitation 360 nm and an emission 460 nm. The level of liberated 4-methylumbelliferone (4-MU) was measured by comparison with standards of 4-MU at 0.25 mM, 0.125 mM, 0.0625 mM, 0.0312 mM, 0.0156 mM, and 0.0078 mM.

Figure 15:
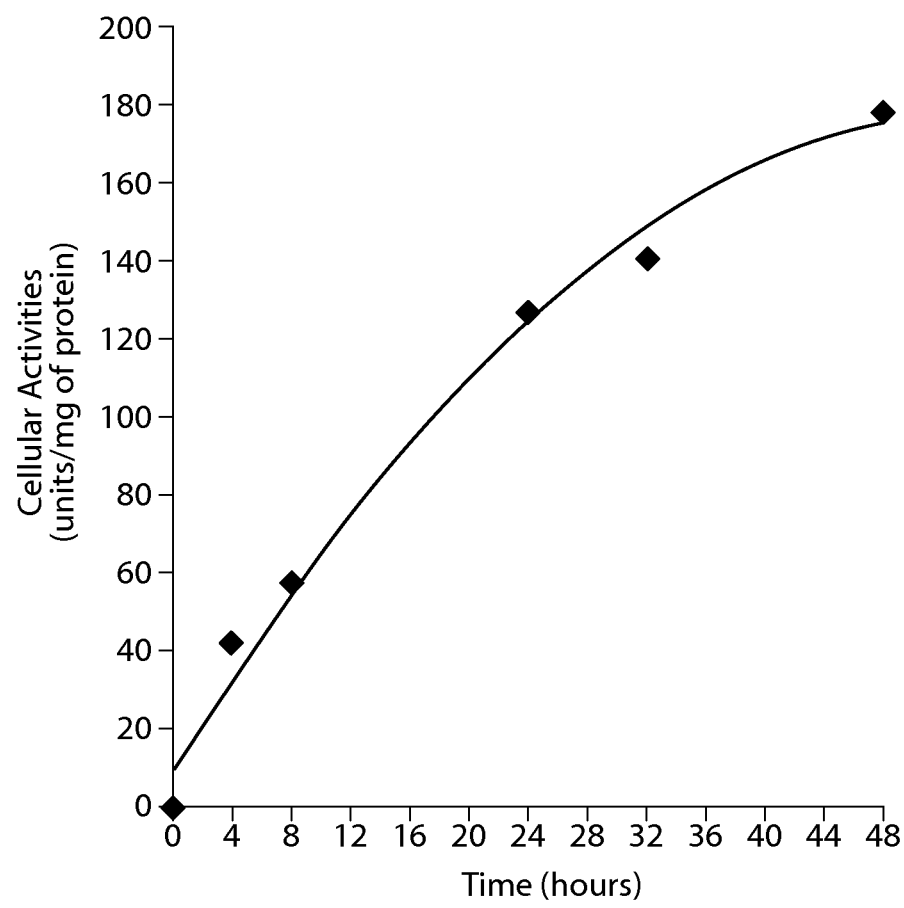
FIG. 15 depicts uptake levels of rhNaGlu (*Gallus*) into a macrophage cell line (NR8383) over time (48 hours). Cellular NaGlu activity was measured in units/mg of protein.

As depicted in FIG. 15, levels of the NaGlu activity in macrophages incubated with 10 μg/mL of rhNaGlu increased almost linearly over a 48 hour period: The rhNaGlu uptake by macrophages was rather slow, but steady throughout the entire time period measured. The relatively slow, extended uptake of NaGlu activity (as compared to other lysosomal enzymes containing M6P and/or mannose in their glycosylation structures) was unexpected and surprising. Equally surprising and unexpected was that a large amount of rhNaGlu proteins was taken up into the macrophages over the extended time period, resulting in intracellular enzymatic activity levels at least 10, 50, 100, 200, 300, 500, or even 1,000-fold higher than the basal levels observed in wild-type macrophages not exposed to rhNaGlu. The results demonstrate that rhNaGlu is extremely stable in extracellular as well as intracellular environments. Further, these results suggest that rhNaGlu may possess physicochemical characteristics that allow for longer serum half-life (e.g., longer circulation) and high serum concentrations in vivo, properties which are ideal for enhanced uptake into the central nervous system (CNS).

TABLE 4

Summary of NaGlu Characteristics

| | Avian (*gallus*) produced rhNaGlu | Natural human NaGlu | CHO produced human NaGlu |
|---|---|---|---|
| Apparent Molecular Mass (kDa) | ~85-~90 | ~86 | ~79-~89 |
| Enzymatic Activity (nmol/min/mg) | >1,000 | ~500 | ~1,057 |
| Mannose-6-phosphate | High | High | None or very Low |

Example 7

Administration of rhNaGlu into NaGlu Deficient Mice

Homozygous null mice were generated from breeding pairs of the strain B6.129S6-NaGlu$^{tm1Efn}$/J. Control wild-type mice were generated in the same manner. Genotyping was performed according to a standard PCR protocol. It is described in the art that at birth, homozygous naglu($^{-/-}$) null mice are viable, normal in size, and do not display any gross physical or behavioral abnormalities, though they exhibited no NaGlu in all tissues (see, Li et al., (1999) *Proc. Natl. Acad. Sci. USA* 96:14505-14510). At one month of age, vacuolated macrophages are found in most tissues. Epithelial cells in kidney and neurons in some parts of the brain are also affected. The vacuolation becomes more prominent with age. At 4-5 months, the mice show abnormal behavior in an open field test. Older animals may have urinary retention and difficulty walking. Typical life span of the homozygous null naglu$^{-/-}$ mice is 8-12 months (see, Li et al., (1999) *Proc. Natl. Acad. Sci. USA* 96:14505-14510).

Intravenous (IV) Administration

The intravenous administration of test article and vehicle by tail vein injection was accomplished as follows. Before injection vasodilation was achieved by gently warming the animal with an incandescent lamp or by soaking the tail in warm water, approximately 43° C. The animal was then placed in restraint device. The surface of the tail was disinfected with 70% isopropanol prior to injection. The lateral veins of the tail are located just under the skin and are identified in the distal part of the tail with the application of tension. A 27 G needle, bevel up, was inserted into the vein for 3-4 mm. The test article or vehicle was then administered as a slow bolus injection over a period of ten seconds as evidenced by the observed clearing of the vein as the administered liquid momentarily occupies the vascular space. After removal of needle, gentle pressure was applied to the puncture site to provide hemostasis. The animal was monitored immediately following procedure to assure normal activity.

Intrathecal (IT) Administration

The intrathecal administration of test article and vehicle by lumbar puncture injection was accomplished as follows. Before injection, animals were anesthetized using isoflurane that was maintained via nose cone throughout the procedure. The site of injection was prepared by shaving the fur, as necessary, prior to each injection. The animal was placed in a prone position on a platform, ensuring the hind limbs were straddling the platform forming a convex curve of the animals back. The surface of the back was swabbed with 70% isopropanol and allowed to dry prior to injection. Spinal column and hip bones were palpated to locate the L4-L5 or L5-L6 margin. A 30 G needle, bevel facing cranially, was inserted into the intervertebral space. Placement was confirmed by the observation of a tail flick. The test article or vehicle was then administered as bolus injection. The animal was allowed to recover from anesthesia and monitored immediately following procedure to assure normal activity and use of limbs.

Results

Twelve-week old naglu$^{-/-}$ mice (B6.129S6-Naglu$^{tm1Efn}$/J) were administered rhNaGlu (*Gallus*) at dose levels of 6.75 or 27 mg/kg via tail vein injection (IV administration), once every other day, for a total of 5 doses (at rhNaGlu concentrations of 1.125, or 4.5 mg/mL, respectively). Similarly, twelve-week old naglu$^{-/-}$ mice were administered with rhNaGlu (*Gallus*) at a dose level of 0.31 mg/kg via lumbar puncture injection (IT administration), once every other day, for a total of 5 doses at NaGlu concentrations of 1.54 mg/mL. Vehicle (10 mM phosphate buffer, 150 mM NaCl and 0.02% Tween80, pH 5.5-5.8) was administered to naglu$^{-/-}$ knock-out mice at the same dose concentration for 5 doses every other day. Untreated wild-type and naglu$^{-/-}$ knock-out mice were also maintained for the duration of the study.

Animals were sacrificed 4 hours after the fifth and final injection. All animals were necropsied and the liver, brain, spleen, heart, lung and kidneys were excised. Each organ was divided sagittally, providing samples for both frozen (−80° C.) and formalin-fixed storage.

Tissue samples were analyzed for: (1) heparan sulfate concentration using an analytical method based on SAX-HPLC analysis of heparan sulfate disaccharides; and (2) α-N-acetylglucosaminidase enzyme activity using a cell-based enzyme activity assay.

Histopathologic evaluation of brain, liver, kidney, spleen, heart and lung tissue was conducted using formalin-fixed tissue samples, embedded in paraffin, sectioned at 4 μm, mounted on glass slides and stained with hematoxylin and eosin (H&E).

Figure 16:
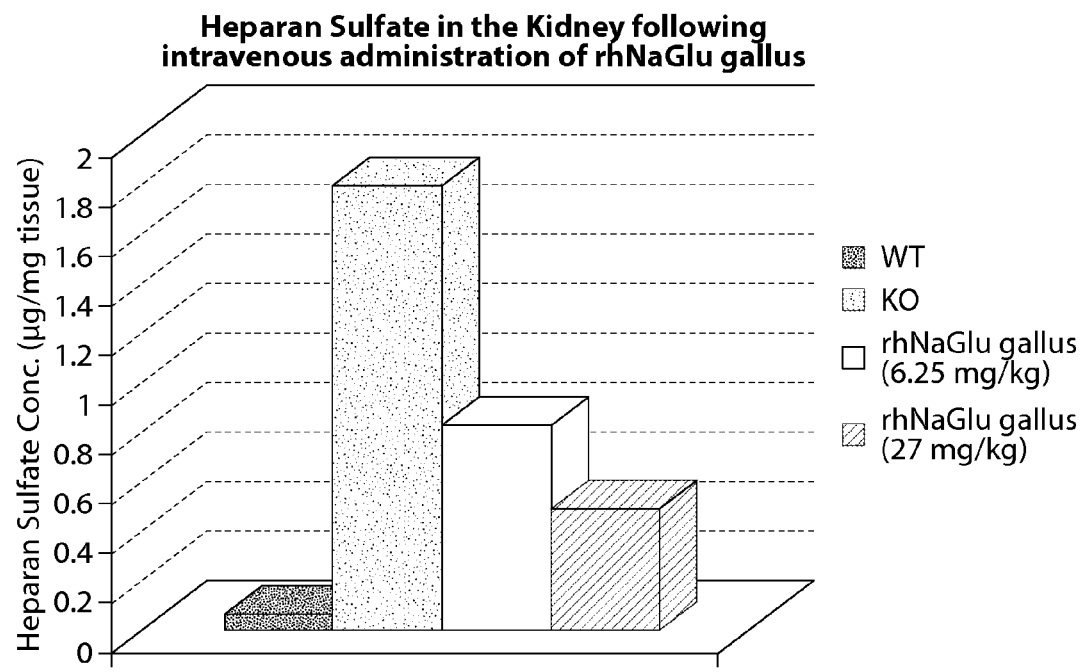
FIG. 16 depicts heparan sulfate substrate levels (μg/mg tissue) in the kidney of naglu ($^{-/-}$) mice following intravenous administration of vehicle (KO); rhNaGlu *gallus* at a dosage concentration of 6.25 mg/kg; or rhNaGlu *gallus* at a dosage concentration of 27 mg/kg. Wild type (WT) mice were untreated.
Figure 17:
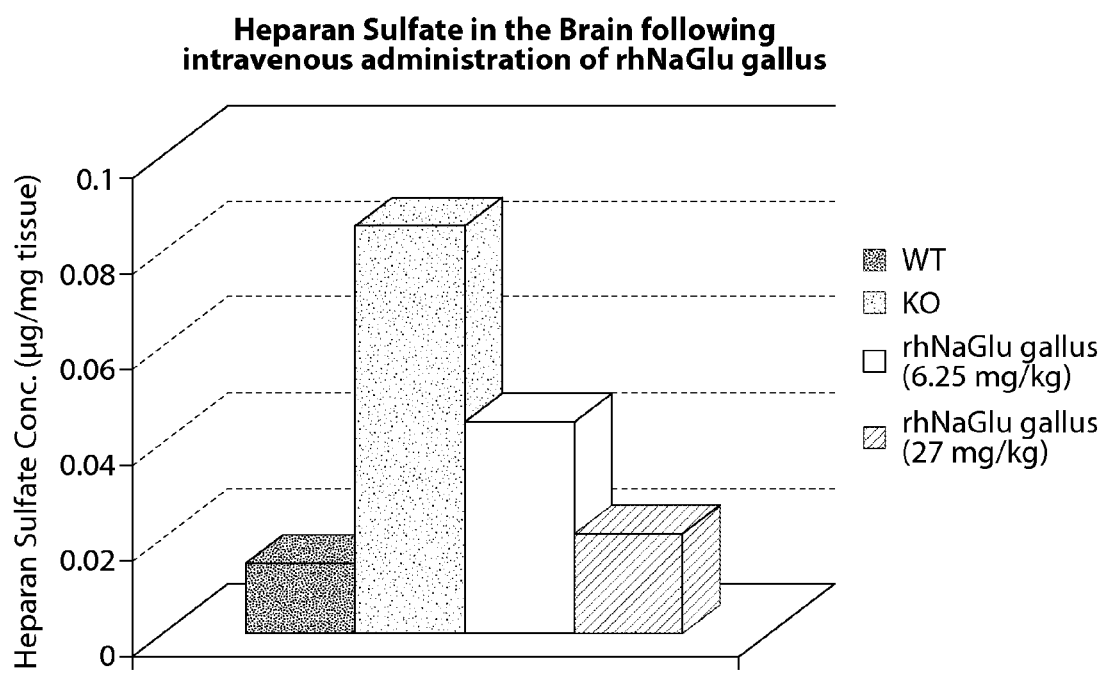
FIG. 17 depicts heparan sulfate substrate levels (μg/mg tissue) in the brain of naglu ($^{-/-}$) mice following intravenous administration of vehicle (KO); rhNaGlu *gallus* at a dosage concentration 6.25 mg/kg; or rhNaGlu *gallus* at a dosage concentration of 27 mg/kg. Wild type (WT) mice were untreated.
Figure 18:
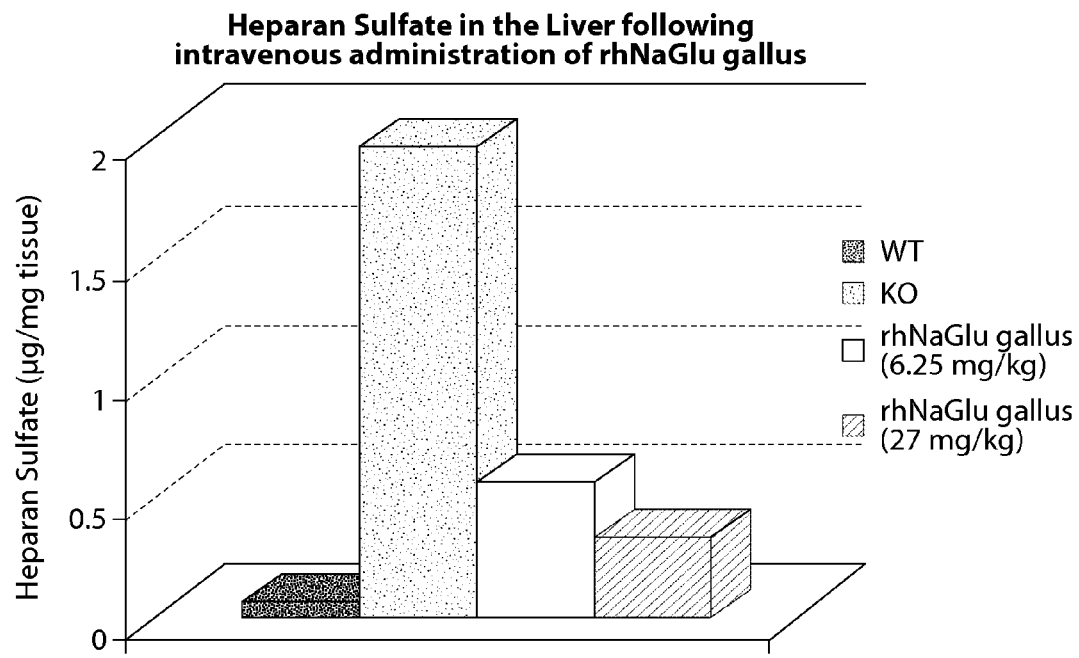
FIG. 18 depicts heparan sulfate substrate levels (μg/mg tissue) in the liver of naglu ($^{-/-}$) mice following intravenous administration of vehicle (KO); rhNaGlu *gallus* at a dosage concentration of 6.25 mg/kg; or rhNaGlu *gallus* at a dosage concentration of 27 mg/kg. Wild type (WT) mice were untreated.

Following the repeated intravenous administration (5 doses over a 10 day period) of rhNaglu (*Gallus*) to naglu$^{-/-}$ mice at dose levels of 6.25 and 27 mg/kg body weight, there was an apparent dose-dependent decrease in the concentration of Heparan Sulfate in the brain, liver and kidney of naglu$^{-/-}$ mice (Table 5; FIGS. 16-18). The relative α-N-acetylglucosaminidase activity was increased in the brain and liver following intravenous administration (Table 6). These results were unexpected and surprising because the NaGlu enzymatic activities and resulting substrate clearance were observed in the brain of the treated naglu$^{-/-}$ mice with the IV administration, suggesting that rhNaGlu (*Gallus*) administered systemically was distributed to the brain of the naglu$^{-/-}$ mice and effective to elicit efficacy even in the present of the blood brain barrier (BBB).

Figure 19:
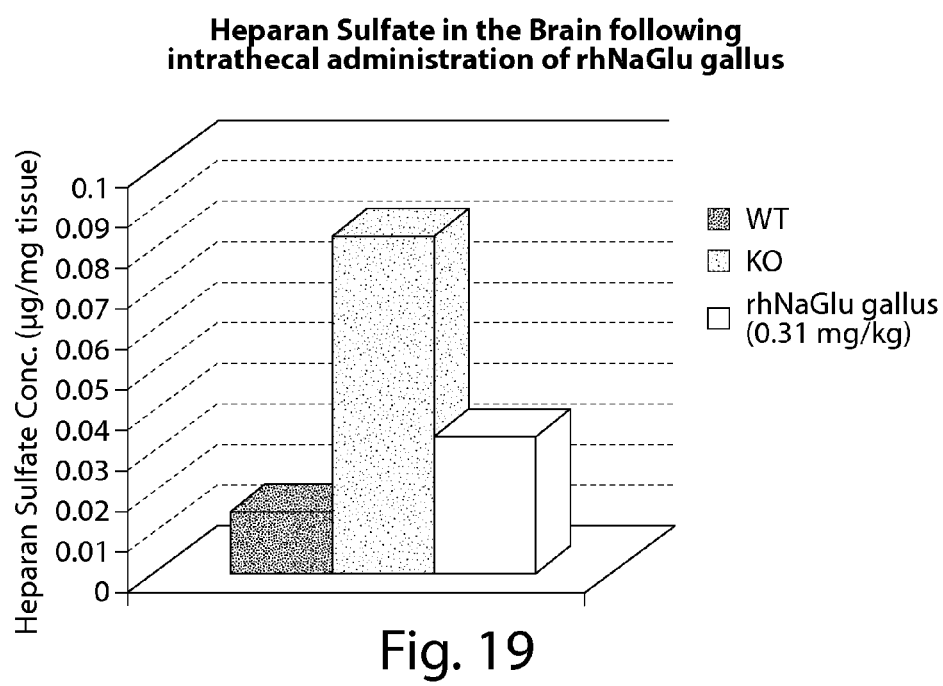
FIG. 19 depicts heparan sulfate substrate levels (μg/mg tissue) in the brain of naglu ($^{-/-}$) mice following intrathecal administration of vehicle (KO) or rhNaGlu *gallus* at a dosage concentration of 0.31 mg/kg. Wild type (WT) mice were untreated.

Following the intrathecal administration (5 doses over a 10 day period) of rhNaGlu (*Gallus*) to naglu$^{-/-}$ mice at a dose level of 0.31 mg/kg, there was a decrease in the concentration of Heparan Sulfate in the brain of naglu$^{-/-}$ mice (Table 5; FIG. 19), suggesting that rhNaGlu (*Gallus*) was targeted to the brain and effective in reducing the accumulated substrate in the brain of naglu$^{-/-}$ mice.

TABLE 5

Tissue Substrate Level (rhNaGlu *Gallus*)

| Tissue | Animal Number | Genotype | Age at sacrifice (wks) | Treatment | Dose (mg/kg) | Route | Heparan Sulfate ug/mg tissue | mean | sd |
|---|---|---|---|---|---|---|---|---|---|
| KIDNEY | 253 | WT | 4 | na | — | — | 0.1 | | |
| | 155 | WT | 12 | na | — | — | 0.045 | 0.0725 | 0.038891 |
| | 178 | KO | 12 | na | — | — | 1.882 | | |
| | 242 | KO | 4 | na | — | — | 1.687 | | |
| | 145 | KO | 13 | na | — | — | 1.904 | | |
| | 474 | KO | 13 | vehicle | 0 | IV | 1.501 | | |
| | 479 | KO | 13 | vehicle | 0 | IV | 1.983 | | |
| | 484 | KO | 13 | vehicle | 0 | IV | 1.839 | 1.799333 | 0.175908 |
| | 487 | KO | 13 | rhNaGlu | 6.25 | IV | 0.928 | | |
| | 492 | KO | 13 | rhNaGlu | 6.25 | IV | 0.737 | 0.8325 | 0.135057 |
| | 481 | KO | 13 | rhNaGlu | 27 | IV | 0.591 | | |
| | 485 | KO | 13 | rhNaGlu | 27 | IV | 0.311 | | |
| | 490 | KO | 13 | rhNaGlu | 27 | IV | 0.585 | 0.495667 | 0.159954 |
| | 86 | KO | 15 | vehicle | 0 | IT | 2.105 | | |
| | 91 | KO | 14 | vehicle | 0 | IT | 1.704 | 1.9045 | 0.28355 |
| | 94 | KO | 14 | rhNaGlu | 0.31 | IT | 1.324 | | |
| | 101 | KO | 14 | rhNaGlu | 0.31 | IT | 2.233 | 1.7785 | 0.64276 |

TABLE 5-continued

Tissue Substrate Level (rhNaGlu *Gallus*)

| Tissue | Animal Number | Genotype | Age at sacrifice (wks) | Treatment | Dose (mg/kg) | Route | Heparan Sulfate ug/mg tissue | mean | sd |
|---|---|---|---|---|---|---|---|---|---|
| LIVER | 253 | WT | 4 | na | — | — | 0.045 | | |
| | 155 | WT | 12 | na | — | — | 0.092 | 0.0685 | 0.033234 |
| | 243 | WT | 4 | na | — | — | 0.045 | | |
| | 178 | KO | 12 | na | — | — | 1.85 | | |
| | 242 | KO | 4 | na | — | — | 2.263 | 2.0565 | 0.292035 |
| | 255 | KO | 4 | na | — | — | 1.85 | | |
| | 474 | KO | 13 | vehicle | 0 | IV | 1.822 | | |
| | 479 | KO | 13 | vehicle | 0 | IV | 1.981 | | |
| | 484 | KO | 13 | vehicle | 0 | IV | 2.004 | 1.961667 | 0.165779 |
| | 487 | KO | 13 | rhNaGlu | 6.25 | IV | 0.748 | | |
| | 492 | KO | 13 | rhNaGlu | 6.25 | IV | 0.444 | | |
| | 504 | KO | 13 | rhNaGlu | 6.25 | IV | 0.494 | 0.562 | 0.163009 |
| | 481 | KO | 13 | rhNaGlu | 27 | IV | 0.491 | | |
| | 485 | KO | 13 | rhNaGlu | 27 | IV | 0.172 | 0.3315 | 0.225567 |
| BRAIN | 253 | WT | 4 | na | — | — | 0.021 | | |
| | 155 | WT | 12 | na | — | — | 0.013 | | |
| | 243 | WT | 4 | na | — | — | 0.014308 | | |
| | 10 | WT | 36 | na | — | — | 0.012649 | 0.015239 | 0.003906 |
| | 239 | KO | 4 | na | — | — | 0.095 | | |
| | 178 | KO | 12 | na | — | — | 0.084 | | |
| | 242 | KO | 4 | na | — | — | 0.099 | | |
| | 255 | KO | 4 | na | — | — | 0.094538 | | |
| | 165 | KO | 24 | na | — | — | 0.084015 | | |
| | 474 | KO | 13 | vehicle | 0 | IV | 0.085447 | | |
| | 479 | KO | 13 | vehicle | 0 | IV | 0.072 | | |
| | 484 | KO | 13 | vehicle | 0 | IV | 0.073 | 0.085875 | 0.009972 |
| | 487 | KO | 13 | rhNaGlu | 6.25 | IV | 0.045 | | |
| | 492 | KO | 13 | rhNaGlu | 6.25 | IV | 0.044119 | | |
| | 504 | KO | 13 | rhNaGlu | 6.25 | IV | 0.044 | 0.044373 | 0.000546 |
| | 481 | KO | 13 | rhNaGlu | 27 | IV | 0.017796 | | |
| | 485 | KO | 13 | rhNaGlu | 27 | IV | 0.016668 | | |
| | 490 | KO | 13 | rhNaGlu | 27 | IV | 0.028 | 0.020821 | 0.006242 |
| | 86 | KO | 15 | vehicle | 0 | IT | 0.094521 | | |
| | 91 | KO | 14 | vehicle | 0 | IT | 0.072623 | 0.083572 | 0.015484 |
| | 94 | KO | 14 | rhNaGlu | 0.31 | IT | 0.038866 | | |
| | 101 | KO | 14 | rhNaGlu | 0.31 | IT | 0.028229 | 0.033548 | 0.007521 | na: Not applicable (mice were untreated).

TABLE 6

Tissue enzymatic activity (rhNaGlu *Gallus*; U/ng protein)

| Tissue | Animal Number | Genotype | Age at sacrifice (wks) | Treatment | Dose (mg/kg) | Route | Enzymatic Activity (U/ug protein) |
|---|---|---|---|---|---|---|---|
| BRAIN | 253 | WT | 4 | na | — | — | 7.7 |
| | 178 | KO | 12 | na | — | — | 0 |
| | 474 | KO | 13 | vehicle | 0 | IV | 0 |
| | 479 | KO | 13 | vehicle | 0 | IV | 0 |
| | 484 | KO | 13 | vehicle | 0 | IV | 0.575 |
| | 487 | KO | 13 | rhNaGlu | 6.25 | IV | 10.58 |
| | 492 | KO | 13 | rhNaGlu | 6.25 | IV | 5.066666667 |
| | 504 | KO | 13 | rhNaGlu | 6.25 | IV | 4.033333333 |
| | 481 | KO | 13 | rhNaglu | 27 | IV | 87.91666667 |
| | 485 | KO | 13 | rhNaGlu | 27 | IV | 90.15 |
| | 490 | KO | 13 | rhNaGlu | 27 | IV | 17.35 |
| LIVER | 253 | WT | 4 | na | — | — | 36.69 |
| | 178 | KO | 12 | na | — | — | 0 |
| | 474 | KO | 13 | vehicle | 0 | IV | 0 |
| | 479 | KO | 13 | vehicle | 0 | IV | 0 |
| | 484 | KO | 13 | vehicle | 0 | IV | 0 |
| | 487 | KO | 13 | rhNaGlu | 6.25 | IV | 512.92 |
| | 492 | KO | 13 | rhNaGlu | 6.25 | IV | 378.805 |
| | 504 | KO | 13 | rhNaGlu | 6.25 | IV | 607.9225 |
| | 481 | KO | 13 | rhNaGlu | 27 | IV | 659.6825 |
| | 485 | KO | 13 | rhNaGlu | 27 | IV | 654.2475 |
| | 490 | KO | 13 | rhNaGlu | 27 | IV | 677.8725 | na: not applicable (mice were untreated).

Each example in the above specification is provided by way of explanation of the invention, not limitation of the invention. In fact, it will be apparent to those skilled in the art that various modifications, combinations, additions, deletions and variations can be made in the present invention without departing from the scope or spirit of the invention. For instance, features illustrated or described as part of one embodiment can be used in another embodiment to yield a still further embodiment. It is intended that the present invention cover such modifications, combinations, additions, deletions, and variations.

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

---

What is claimed is:

1. A method of treating a subject suffering from NaGlu deficiency, the method comprising intravenously administering to the subject a therapeutically effective amount of a composition comprising an isolated recombinant human N-acetyl-alpha-D-glucosaminidase (rhNaGlu) whose amino acid sequence is set forth in 24-743 of SEQ ID NO:1, wherein said rhNaGlu comprises one or more glycan structures having sufficient amount of mannose-6-phosphate (M6P) that allows for internalization of said rhNaGlu into a mammalian cell having NaGlu deficiency via M6P receptor-mediated endocytosis, such that when internalized in vivo into a subject showing a deficiency in NaGlu, said rhNaGlu restores at least 50% of NaGlu activity observed in a cell of the same type in a normal subject, and wherein the rhNaGlu contains at least 1 mole of M6P per mole of the rhNaGlu protein, with the proviso that the rhNaGlu is not administered intrathecally.

2. The method of claim 1, wherein said NaGlu deficiency is Sanfilippo syndrome B.

3. The method of claim 1, wherein said subject is a human.

4. The method of claim 1, wherein said recombinant human NaGlu protein is administered at a dosage of about 1 mg rhNaGlu per kg body weight to about 30 mg rhNaGlu per kg body weight.

5. The method of claim 1, wherein said therapeutically effective amount is an amount effective to reduce heparan sulfate levels in the brain, the kidney, or the liver of the subject.

6. The method of claim 1, wherein said therapeutically effective amount is an amount effective to increase NaGlu activity in the brain or the liver of the subject.

7. The method of claim 1, further comprising administering a second therapeutic agent.

8. The method of claim 7, wherein the second therapeutic agent is an immunosuppressant.

9. A method of delivering recombinant human NaGlu protein to the brain of a subject suffering from NaGlu deficiency, the method comprising intravenously administering recombinant human NaGlu protein (rhNaGLU) whose amino acid sequence is set forth in 24-743 of SEQ ID NO:1 to the subject, wherein the rhNaGlu comprises one or more glycan structures that contain mannose-6-phosphate (M6P) and contains at least 1 mole of M6P per mole of rhNaGlu protein, with the proviso that the rhNaGlu is not administered intrathecally.

10. The method of claim 1, wherein the ratio of M6P to rhNaGlu protein is determined by high-performance anion exchange chromatography with pulsed amperometric detection (HPAEC-PAD).

11. The method of claim 9, wherein the ratio of M6P to rhNaGlu protein is determined by high-performance anion exchange chromatography with pulsed amperometric detection (HPAEC-PAD).

12. A method of treating a subject suffering from Sanfilippo Syndrome B, comprising intravenously administering to the subject a therapeutically effective amount of a composition comprising recombinant human N-acetyl-alpha-D-glucosaminidase (rhNaGlu), wherein the amino acid sequence of said rhNaGlu is amino acids 24-743 of SEQ ID NO:1, the rhNaGlu comprises one or more glycan structures that contain mannose-6-phosphate (M6P) and contains about 1 to 6 moles of M6P per mole of rhNaGlu protein, with the proviso that the rhNaGlu is not administered intrathecally.

13. The method of claim 12, wherein the therapeutically effective amount is about 1 mg rhNaGlu per kg body weight to about 5 mg rhNaGlu per kg body weight.

14. The method of claim 12, wherein the therapeutically effective amount is about 5 mg rhNaGlu per kg body weight to about 30 mg rhNaGlu per kg body weight.

15. The method of claim 12, wherein the therapeutically effective amount is about 5 mg rhNaGlu per kg body weight to about 10 mg rhNaGlu per kg body weight.

16. The method of claim 12, wherein the therapeutically effective amount is about 5 mg rhNaGlu per kg body weight.

17. The method of claim 12, wherein the therapeutically effective amount is about 10 mg rhNaGlu per kg body weight.

18. The method of claim 12, wherein the ratio of M6P to rhNaGlu protein is determined by high-performance anion exchange chromatography with pulsed amperometric detection (HPAEC-PAD).

* * * * *